(12) United States Patent
Jaquith et al.

(10) Patent No.: US 7,129,250 B2
(45) Date of Patent: Oct. 31, 2006

(54) NEUROPROTECTIVE AND ANTI-PROLIFERATIVE COMPOUNDS

(75) Inventors: James B. Jaquith, Pincourt (CA); Alexander Graham Fallis, Ottawa (CA); John W. Gillard, Baie D'Urfe (CA); Alain Laurent, Montreal (CA)

(73) Assignee: Aegera Therapeutics Inc., Verdun (CA)

( * ) Notice: Subject to any disclaimer, the term of this patent is extended or adjusted under 35 U.S.C. 154(b) by 16 days.

(21) Appl. No.: 10/637,599

(22) Filed: Aug. 11, 2003

(65) Prior Publication Data

US 2004/0220202 A1 Nov. 4, 2004

Related U.S. Application Data

(63) Continuation-in-part of application No. 10/276,803, filed as application No. PCT/CA01/00718 on May 18, 2001, now abandoned.

(30) Foreign Application Priority Data

May 19, 2000 (CA) .................... 2308994

(51) Int. Cl.
  *A61K 31/437* (2006.01)
  *A61K 31/404* (2006.01)
  *C07D 471/04* (2006.01)
  *C07D 403/14* (2006.01)

(52) U.S. Cl. ............... 514/300; 546/113; 548/305.1; 548/455; 514/394; 514/415

(58) Field of Classification Search ........... 514/300, 514/415, 394; 546/113; 548/305.1, 455
See application file for complete search history.

(56) References Cited

U.S. PATENT DOCUMENTS

| | | | |
|---|---|---|---|
| 4,877,776 A | 10/1989 | Murakata et al. | |
| 4,923,986 A | 5/1990 | Murakata et al. | |
| 5,057,614 A * | 10/1991 | Davis et al. | 548/466 |
| 5,405,864 A | 4/1995 | Broka | |
| 5,621,101 A | 4/1997 | Lewis et al. | |
| 5,741,808 A | 4/1998 | Lewis et al. | |
| 5,756,494 A | 5/1998 | Lewis et al. | |
| 5,859,261 A | 1/1999 | Faul et al. | |
| 5,883,114 A | 3/1999 | Kleinschroth et al. | |
| 5,919,912 A | 7/1999 | Korneluk et al. | |

(Continued)

FOREIGN PATENT DOCUMENTS

DE    40 05 970    8/1991

(Continued)

OTHER PUBLICATIONS

Kitada, S. et al, "Blood", 2000, 96,393.

(Continued)

*Primary Examiner*—Charanjit S. Aulakh
(74) *Attorney, Agent, or Firm*—Gail C. Silver; Borden Ladner Gervais LLP

(57) ABSTRACT

This invention features ring-substituted pyrrolo-β-carboline derivatives and ring-substitution and structural derivatives of 3-(1H-indol-3-yl)-1H-pyrrole-2,5-dione of formulas I–III, which are useful as neuroprotective and anti-proliferative compounds. Also disclosed are methods for the preparation of these compounds, selected biological profiles and uses of these compounds in the treatment of various neurodegenerative and inflammatory diseases of the human nervous system and in the treatment of various other proliferative disorders characterized by loss of growth or cellular differentiation control including, but not limited to, cancer and inflammation.

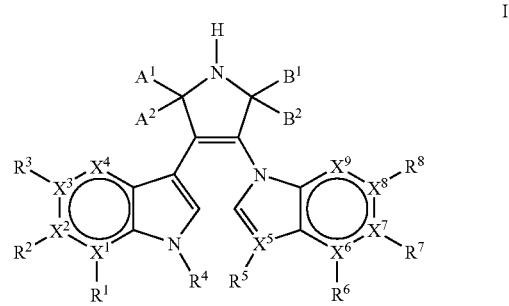

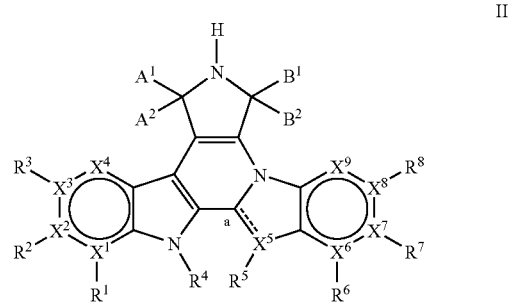

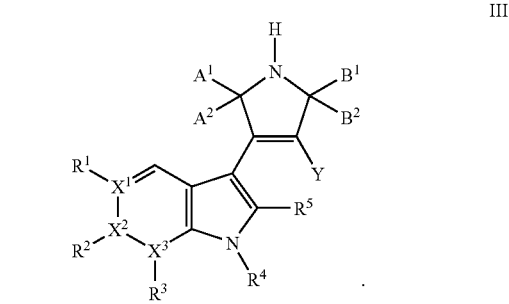

9 Claims, 3 Drawing Sheets

U.S. PATENT DOCUMENTS

| | | |
|---|---|---|
| 5,919,946 A | 7/1999 | Faul et al. |
| 6,013,646 A | 1/2000 | Roder et al. |
| 6,020,127 A | 2/2000 | MacKenzie et al. |
| 6,037,475 A | 3/2000 | Faul et al. |

FOREIGN PATENT DOCUMENTS

| | | |
|---|---|---|
| EP | 0 328 026 | 8/1989 |
| EP | 0 397 060 | 11/1990 |
| EP | 0 540 956 | 5/1993 |
| EP | 0 643 966 | 3/1995 |
| WO | WO 94/02488 | 2/1994 |
| WO | WO 94/27982 | 12/1994 |
| WO | WO 95/07911 | 3/1995 |
| WO | WO 96/31515 | 10/1996 |
| WO | WO 97/34890 | 9/1997 |
| WO | WO 97/46565 | 12/1997 |
| WO | WO 97/49406 | 12/1997 |
| WO | WO 98/04551 | 2/1998 |
| WO | WO 99/42100 | 8/1999 |
| WO | WO 99/47518 | 9/1999 |
| WO | WO 99/47522 | 9/1999 |
| WO | WO 01/87887 | 11/2001 |

OTHER PUBLICATIONS

Iqbal, K. et al., FEBS Lett., 1994, 349, 104.
Garver, T.D. et al., J. Neurosci. Res., 1996, 44, 12.
Kaneko, et al., J. Med. Chem., 1997, 40, 1863.
Maroney, A.C. et al., J. Neurosci. 1998, 18, 104.
Sancelme, et al., J. Antibiotics, 1994, 47, 792.
Hachisu et al., Life Sciences, 1989, 44, 1351.
Bit et al., J. Med. Chem., 1993, 36, 21.
Bergman et al., Tetrahedron Lett., 1987, 28, 4441.
Faul, M.M. et al., Tetrahedron Lett., 1999, 40, 1109.
Bradshaw, D. et al., Agents and Actions, 1993, 38, 137.
Knusel, B. & Hefti, F.J., Neurochem., 1992, 59, 1987.
Xu, D.G. et al., Nature Medicine, 1997, 3, 997.
Uzawa, et al., Cancer Genet Cytogenet, 1998, 11, 125.
Chan, S.L., Mattson, M.P., J. Neurosci. Res., 1999, 58, 167.
Kanfer, J.N. et al., Neurochem Res., 1999, 24, 1621.
Suzuki, A. et al., Exp. Cel. Res., 1997, 233, 41.
Gribble, G. W. et al., Studies in Natural Products Chemistry, 1993, 12, pp. 365-409.
Wood, J. L. et al., J. Am. Chem. Soc., 1997, 119, pp. 9641-9651.
Link et al., J. Am. Chem. Soc., 1996, 118, pp. 2825-2842.
Bergman, J. et al., Tetrahedron, 55, 1999, pp. 2363-2370.
Janosik et al., Tetrahedron, 55, 1999, pp. 2371-2380.
Nakanishi, J. Antibiotics, 1986, 39, pp. 1066-1071.
Toledo and Lydon, Structure, 1997, 5, No. 12, pp. 1551-1556.
Davis, P.D., et al., "Inhibitors of Protein Kinase C.I. 2,3-Bisarylmaleimides", Journal of Medicinal Chemistry, vol. 35, No. 1, Jan. 10, 1992, pp. 177-184, XP002028954.
Davis, P.D., et al., "A Mild Conversion of Maleic Anhydrides into Meleimides" Tetrahedron Letters, vol. 31, No. 36, 1990, pp. 5201-5204, XP001021319.

* cited by examiner

Control          Compound 27 (3 uM)

NEUROPROTECTIVE AND ANTI-PROLIFERATIVE COMPOUNDS

This application is a continuation-in-part of and claims priority to U.S. patent application Ser. No. 10/276,803 (filed Oct. 23, 2003), now abandoned, the entirety of which is herein incorporated by reference. U.S. patent application Ser. No. 10/276,803 is the National Phase application of PCT/CA01/00718 (filed May 18, 2001), the entirety of which is herein incorporated by reference. This application claims priority to Canadian Patent Application Serial No. 2,308,994 (Filed May 19, 2000), the entirety of which is herein incorporated by reference.

FIELD OF THE INVENTION

This invention features pyrrolo-β-carboline derivatives and derivatives of 3-(1H-indol-3-yl)-1H-pyrrole-2,5-dione which are useful in prevention and treatment of degenerative and inflammatory diseases of the central and peripheral nervous systems, by inhibiting axonal degradation and/or neuronal apoptosis, as well as in the treatment and prevention of cancer and inflammation by inducing apoptosis in proliferating cells.

BACKGROUND OF THE INVENTION

The regulation of cellular responses to ischemic, excitotoxic, pathogenic or chemotoxic stresses in the central and peripheral nervous systems (CNS and PNS, repectively), including for example, the brain, the spinal cord, the eye, and the peripheral sensory and motor neurons, is a major frontier of modem medicine. Neurons are non-proliferating cells whose progressive or abrupt loss can result in diseases exemplified by Alzheimer's disease (AD), Parkinson's disease (PD), Huntington's disease (HD), amyotrophic lateral sclerosis ("ALS" or "Lou Gehrig's disease"), and stroke. These diseases and disorders are individually or collectively referred to herein as "central neurodegenerative diseases." Selected symptoms resulting from these diseases include memory loss, loss of cognitive function, loss of gross and fine motor control, and blindness. Peripheral neuronal loss or neurite damage results in sensory loss exemplified by pain or discomfort, sensorimotor defects, and paralysis.

The incidence of central neurodegenerative diseases increases with age. For example, less than 5% of the population under the age of 65 displays signs of AD. An exponential increase is observed over the age of 65, with as much as 47% of the population displaying some form of AD over the age of 85. Many factors (etiological agents) are responsible for the initiation of neurodegenerative conditions, factors as varied as genetic DNA damage or loss in the mitochondria, abnormal amyloid processing, oxidative stress following ischemia and reperfusion, and loss of neurotrophic support for the nerve cells. The mode of action ultimately underlying such irreversible neuronal loss involves programmed cell death, or apoptosis. Preventing neuronal apoptosis and neurite disfunction represents a new, broad-spectrum, approach to the treatment of progressive central neurological disorders Various other neurodegenerative diseases related to the peripheral nervous system, herein referred to as "peripheral neuropathies", are characterized by the loss of feeling, experiencing pain, and even paralysis of or in the extremities. These peripheral neuropathies result from disease states such as ALS, Multiple Sclerosis, AIDS, diabetes, and various neuropathies induced by chemotherapeutic treatments such as cisplatin, vinblastine and taxane (Taxol™ and Taxotere™) treatment for cancer therapy, and D4T for the treatment of HIV (Human Insufficiency Virus). In most of these cases, progressive loss of axonal finction occurs initially, resulting in severe symptoms, followed by the apoptotic loss of the neuron. In these cases, inhibiting neuronal apoptosis and or axonal degradation is a new approach to treating these diseases.

A recently discovered family of genes, known as the IAPs (Inhibitor of Apoptosis Proteins), potently inhibit apoptosis in most mammalian cell lines. Members of the LAP family, specifically NAIP, HIAP1,2 and XLIP, are used as survival factors by both neurons and cancer cells to resist intrinsic apoptosis.

NAIP's (Neuronal Apoptosis Inhibitory Protein) primary finction appears to be the regulation of neuronal apoptosis (Xu, D. G. et al. *Nature Medicine* 1997, 3, 997). NAIP is primarily expressed in neurons where it serves to protect these post-mitotic cells against environmental and metabolic stresses that lead to premature apoptosis of the neuron. Indeed, deletions in the NAIP gene were found to be causally related to the severity of the childhood genetic neuromuscular disease, Spinal Muscular Atrophy (SMA).

Enhancement of NAIP expression in the brain was achieved through the systemic in vivo administration of a neuroprotective alkaloid, K252a (for the isolation and identification of K252a see Sezaki, M. *J Antibiot*. 1986, 39, 1066, U.S. Pat. No. 6,020,127). In vivo studies demonstrated increased expression of NAIP in hippocampal neurons after K252a administration to rats. These results correlate well with increased protection to ischemic insults provided by this compound (see Xu, D. G. et al. *Nature Medicine* 1997, 3, 997). Knock-out mice lacking the expression of NAIP displayed dramatic neuronal sensitivity to such ischemic insults.

The exact mechanism by which K252a upregulates NAIP gene expression is not known. However, it is known that K252a inhibits several classes of protein kinases. The X-ray crystal structure of a closely related natural product alkaloid, staurosporine, when bound to the protein kinases CDK2 and cAPK confirmed that staurosporine acts as a competitive inhibitor for the conserved binding site of adenosine triphosphate (ATP), which is found in all known protein kinases enzymes (for a review see Toledo and Lydon *Structure* 1997, 5, 1551). Several groups have suggested that K252a and its structural analogues, the indolocarbazoles, also bind to the ATP binding site of various protein kinases. A large number of natural products related to the K252a structure (indolocarbazoles) also inhibit various serine-threonine protein kinases. Most of these compounds have undesirable neuronal cytotoxic effects due to their lack of kinase specificity. Non-specific kinase inhibitory compounds can interrupt the neuronal survival signaling pathways for example, by inhibiting PKB or PKC. In fact, protein kinase deregulation has been implicated as a contributing factor to various neurodegenerative disorders (Bradshaw, D. et al. *Agents and Actions* 1993,38, 137; Knusel B. & Hefti F. J. *Neurochem*. 1992, 59, 1987). This class of compounds is typified by the following compounds:

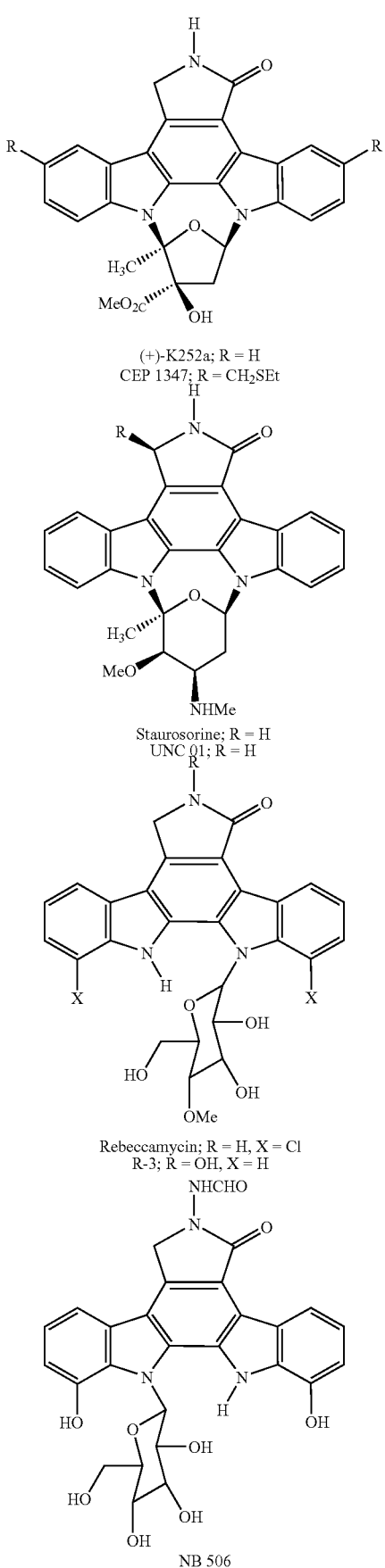

K252a displays significant neuronal cytotoxicity at moderate doses in vitro which preclude the measurement of upregulation of NAIP gene expression as a true indication of its neuroprotective mechanism in either cultured neuroblastoma cells or cerebellar granule neurons (CGN). These findings suggest that highly specific compounds will be required in order to have pharmaceutical potential in regulating pro-apoptotic action in various diseases.

Various cancers and cell lines, including colon, lung, and breast, display elevated levels of other IAPs, including HIAP1,2 and XIAP, as either mRNA and/or protein (U.S. Pat. No. 5,919,912). Scientist at Aegera Therapeutics Inc. have shown that the down-regulation of the ILAPs in cancer cells can effectively shift the chemotherapeutic dose response required to kill such cancer cells, in the case of HAIP1, or to kill cancer cells outright, in the case of XIAP (US pat application. Compounds that down-regulate the expression of these genes would therefore be useful in treating cancers. In several cases, the cytotoxic properties of the indolocarbazoles have been exploited to affect a therapeutic use in cancer eg. Staurosporine, UNC 01, Rebeccamycin and NB 506 amongst others. Specifically, UNC 01 down regulates XIAP expression in B-cell chronic lymphocytic leukemia cell lines, inducing apoptosis (Kitada, S. et al *Blood* 2000, 96, 393).

Indolocarbazole Alkaloids Staurosporine and K252a

Various derivatives of the natural products Staurosporine and K252a have been described for the treatment of neurodegenerative disorders. U.S. Pat. No. 6,013,646 to Roderet al. (issued Jan. 11, 2000) discloses K252a derivatives incorporating a carbon at the tetrahydrofuran oxygen position of the K252a sugar moiety prevents tau hyperphosphorylation by the direct inhibition of the ERK family of protein kinases, also known as the MAP kinases. Tau hyperphosphorylation results in the destabilization of regular microtubular organization and the formation of neurofibular tangles (Iqbal, K. et al. FEBS Lett., 1994, 349, 104; Garver, T. D. et al., *J. Neurosci. Res.*, 1996, 44, 12). Neurofibulary tangles are associated with neurodegenerative diseases such as AD and PD. A report by Murakata, C. et al. (*J. Med Chem.* 1997, 40, 1863) established that the semisynthetic K252a analogue, CEP 1347, is a selective neurotrophic agent in which the undesirable TrkA and PKC inhibitory activities have been reduced, as demonstrated in a ChAt assay. Additionally, this class of compounds appears to inhibit the production of TNF-α (tumour necrosis factor), which is intimately involved in the initiation of neuronal apoptosis. At the same time CEP 1347 and related compounds upregulated the production of IL-1β (Mallamo et al, WO96/31515; Hudkins et al, WO 97/46565; Engber et al, WO97/49406). Maroney, A. C. et al. showed that CEP 1347 inhibited JNK1 activation (*J. Neurosci.*, 1998, 18, 104).

Other indolocarbazole derivatives are disclosed by Glicksman, M. A. et aL (WO 95 07911), Lewis, M. E. (WO 94 02488), Lewis, M. E. et al. (U.S. Pat. No. 5,756,494, No. 5,741,808, and No. 5,621,101). Indolocarbazole derivatives have also been reported for use in treatment of cancer (EP 0 323 171, EP 0 643 966, U.S. Pat. No. 4,923,986, U.S. Pat. No. 4,877,776, WO 94 27982), as antimicrobial agents (Prudhomme et al, *J. Antibiotics*, 1994, 47, 792) and in the treatment of hypertension (Hachisu et al. *Life Sciences* 1989, 44, 1351).

A variety of synthetic procedures have been reported in the literature for the preparation of bis(indolyl)pyrrole-2,5-diones and indolocarbazoles. See, for example, Bit et al., *J. Med. Chem.*, 1993, 63, 21; Bergman et al., *Tetrahedron Lett.*, 1987, 28, 4441; Davis et al., *Tetrahedron Lett.*, 1990, 31, 2353, 5201; Faul, M. M. et al., *Tetrahedron Lett*, 1999, 40, 1109; Faul M M. et al. U.S. Pat. Nos. 5,859,261, 5,919,946, and 6,037,475. For a general review of the chemistry and properties of these alkaloids see Gribble, G. W.; Berthel, S. J. "Studies in Natural Products Chemistry", 1993, 12, 365. For synthetic studies see Wood, J. L. et al. *J. Am. Chem. Soc.* 1997, 119, 9641; and Danishefsky, S. et al *J. Am. Chem. Soc.* 1996, 118, 2825.

A class of indolocarbazoles having fused imidazolyl ring systems are known as the granulatimides. Iso-granulatimide has been shown to be an effective G2 check point inhibitor in p53 deficient cancer cell lines, suggesting its potential in cancer chemotherapy (PCT WO99/47522, Sep. 23 1999). Some members of this class are illustrated below.

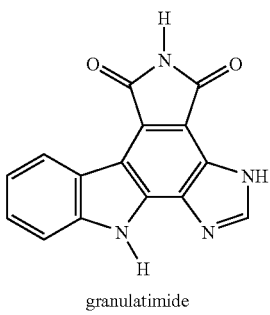

granulatimide

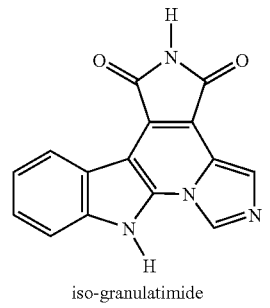

iso-granulatimide

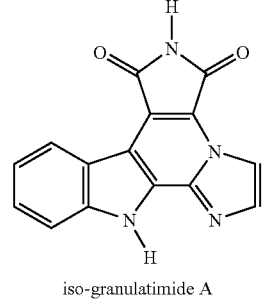

iso-granulatimide A

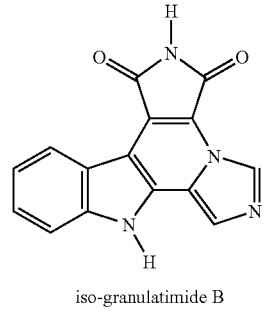

iso-granulatimide B

-continued

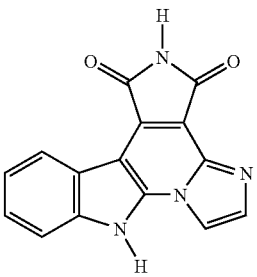

iso-granulatimide C

Pyrrolo-β-Carbazole Derivatives.

Compound "a", below, represents a typical intermediate in the synthesis of certain disclosed pyrrolo-β-carboline compounds, and was reported by Davis et al. (*J. Med. Chem.*, 1992, 35, 177) as an inhibitor of PKC. This compound was prepared using a different chemistry than that of the instant invention, and has not been further elaborated or cyclized.

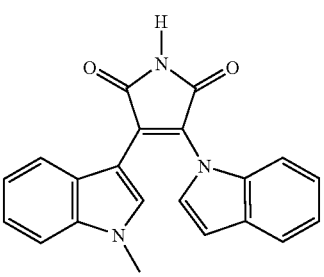

a

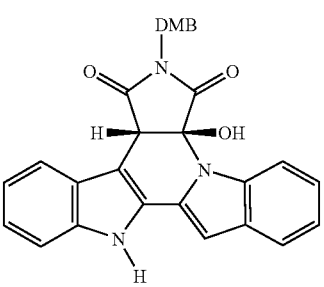

b

Compound "b", above, has been proposed as an undesirable, unstable intermediate in the synthesis of staurosporine aglycone. The compound was not isolated or further elaborated (Wood, J. L. et al., *J. Am. Chem. Soc.*, 1997, 119, 9641).

A variety of synthetic procedures have been reported in the literature for the preparation of 3-(1H-indol-3-yl)-1H-pyrrole-2,5-diones involving the condensation of indole with maleimide (Bergman, J. et al. *Tetrahedron*, 1999, 55). Most of these synthetic procedures have distinct limitations with regards to the use of harsh reaction conditions, thereby limiting the functional groups tolerated during the coupling reactions, the need for protection of the pyrrole-2,5-dione nitrogen, and the total number of synthetic steps required for the preparation of the desired indolocarbazole nuclei.

SUMMARY OF THE INVENTION

The present invention provides novel pyrrolo-β-carboline derivatives and ring-substitution and structural derivatives of 3-(1H-indol-3-yl)-1H-pyrrole-2,5-diones. Compounds disclosed herein are useful for the treatment of neurodegenerative diseases, facilitating regulation of the IAPs, inhibition of various serine-threonine protein kinases, inhibiting the degradation, dysfunction, or loss of neurons of the CNS and PNS, or enhancing the phenotype of neuronal cells and neuronal progress and development, either in the CNS or in the PNS.

Compounds disclosed herein are also useful in the prevention and treatment of other disorders and physiological conditions characterized by loss of growth and cellular differentiation control, as exemplified in cancer and inflammation, and various human and viral signal transduction processes. This utility arises from the inhibition of various protein kinases or by the down regulation of the IAPs including, but not limited to HIAP1, HIAP2, and XIAP. Downregulation of anti-apoptotic genes in cancer cell lines, causing cell death, is useful in cancer chemotherapy.

The invention also relates to a general synthetic route, permitting preparation of pyrrolo-β-carboline derivatives (Structure II) which are distinct from the indolocarbazole class of compounds and their synthetic precursors, which represent 3-(indol-3-yl)-4-(1-aza-heterosubstituted)-1H-pyrrole-2,5-diones (Structure I). Various substituted 3-(indol-3-yl)-1H-pyrrole-2,5-diones can be prepared using a related, one-pot, chemical procedure. Selected compounds of this class display potent biological activity. For example, these compounds display in vitro neuroprotection against multiple apoptotic stresses. These anti-apoptotic compounds are usefull in the treatment of acute and chronic neurodegeneration, which has been further exemplified in animal models of PD.

Also included are inventive methods for the preparation of the compounds disclosed herein.

The ring-substitution pyrrolo-β-carboline derivatives and precursors of the present invention are compounds of formula I and II:

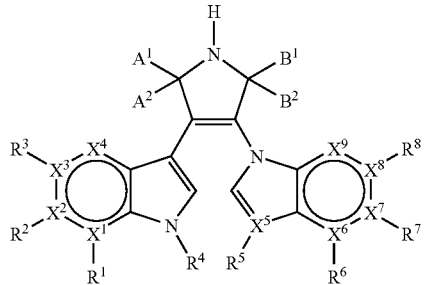

I

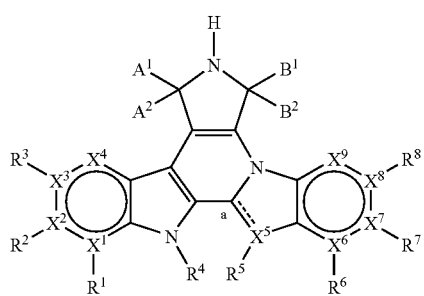

II

Formulas I and II have functional groups designated as $A^1$, $A^2$, $B^1$, $B^2$, $X^1$–$X^9$ and $R^1$–$R^8$ as defined further herein. The difference between formula I and formula II resides in the bonds made with the carbon atom shown above as "a" in formula II. The dashed line in formula II indicates that the bond between carbon "a" and $X^5$ may be either single or double bond. The definitions of functional groups having the same designations are the same for compounds of formula I and II, but may differ from functional groups having the same designation in formula III (below).

The 3-(indol-3-yl)-1H-pyrrole-2,5-diones analogues of the present invention are compounds of formula III:

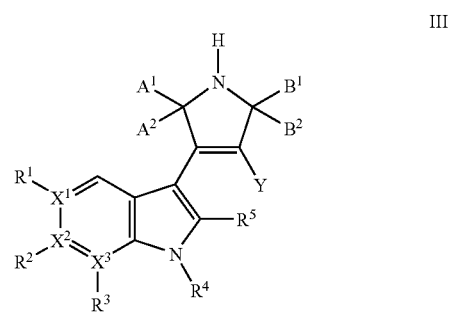

III

Formula III has functional groups designated as $A^1$, $A^2$, $B^1$, $B^2$, $X^1$–$X^3$, $R^1$–$R^5$, and Y as defined further herein. The definitions of functional groups for compounds of formula III may differ from the definitions of functional groups having the same designation with respect to formula I and II.

BRIEF DESCRIPTION OF THE DRAWINGS

The invention is now described with reference to the accompanying drawings described below.

DETAILED DESCRIPTION

Figure 1:
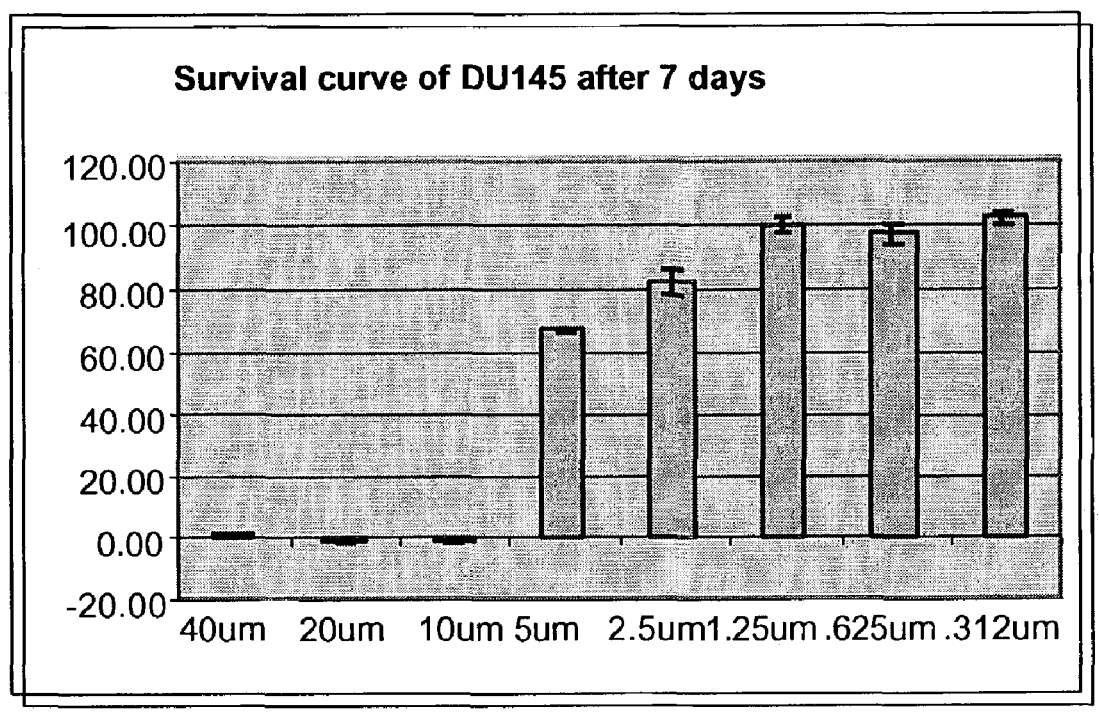
FIG. 1 depicts the killing of DU145 prostate cancer cells with compound 136 (described in Example 136). A survival curve is shown for DU145 after seven days of treatment with the compound at varying concentrations.

Ring-Substitution and Structural Derivatives of Pyrrolo-β-Carboline Derivatives

Disclosed herein are pharmaceutically active ring-substitution and structural derivatives of pyrrolo-β-carboline derivatives, represented by formulas I and II:

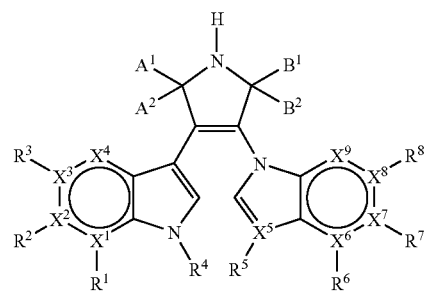

I

-continued

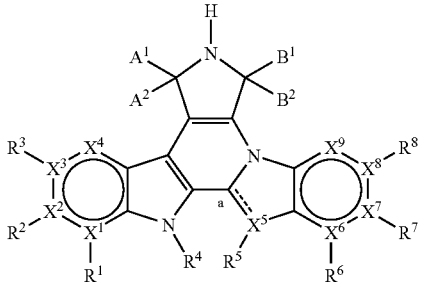

II and pharmaceutically acceptable salts thereof wherein:

formula I represents the non-cyclized form of formula II, and formula II is defined as either having a single or double bond between carbon "a" and $X^5$;

$A^1$ is H or lower alkyl, $A^2$ is H, $OR^{20}$, or $SR^{20}$, having S or R stereochemistry, wherein $R^{20}$ represents H, lower alkyl, aryl, substituted aryl, heteroaryl, or substituted heteroaryl; or $A^1$ and $A^2$ are combined to represent oxygen;

$B^1$ is H or lower alkyl, and $B^2$ is H, $OR^{20}$, or $SR^{20}$, having S or R stereochemistry; or $B^1$ and $B^2$ are combined to represent oxygen;

$X^1$–$X^3$ are independently C or N;

$X^4$ is CH or N, wherein not more than two of $X^1$–$X^4$ is N;

$X^5$ represents N or C when bound to carbon "a" with a double bond, and $X^5$ represents CH or N when bound to carbon "a" with a single bond;

$X^6$–$X^8$ are independently C or N;

$X^9$ is CH or N, wherein not more than two of $X^6$–$X^9$ is N;

$R^1$–$R^3$ and $R^6$–$R^8$ represent a lone pair or O when each respective $X^1$–$X^3$ and $X^6$–$X^8$ is N; and when $X^1$–$X^3$ or $X^6$–$X^8$ is C, each respective $R^1$–$R^3$ and $R^6$–$R^8$ is independently selected from the group consisting of:

a) H, lower alkyl, lower substituted alkyl, higher alkyl, halogen, azido, cyano, nitro, or $NR^{21}R^{22}$, wherein $R^{21}$ represents H or lower alkyl, and $R^{22}$ represents H, lower alkyl, acyl, formyl, lower alkylcarbonyl, substituted lower alkylcarbonyl, carbonyl, arylcarbonyl, substituted arylcarbonyl, heterocycle, heteroarylcarbonyl, substituted heteroarylcarbonyl, lower alkylaminocarbonyl, arylaminocarbonyl, or substituted arylaminocarbonyl;

b) $OR^{23}$, wherein $R^{23}$ is H, acyl, carbonyl, lower alkylcarbonyl, substituted lower alkylcarbonyl, arylcarbonyl, or substituted arylcarbonyl;

c) $SR^{23}$;

d) $O(CH_2)_j$—$R^{24}$, $O(CH_2)_j$—O—$R^{24}$, or $O(CH_2)_j$—S—$R^{24}$, wherein j is an integer from 1 to 8, and $R^{24}$ is selected from the group consisting of H, lower alkyl, substituted lower alkyl, aryl, substituted aryl, heteroaryl, or substituted heteroaryl;

e) $S(CH_2)_j R^{24}$, $S(CH_2)_j$—O—$R^{24}$, or $S(CH_2)_j$—S—$R^{24}$;

f) C≡C—$R^{25}$, C≡C—$OR^{25}$, or C≡C—$CO_2R^{25}$, wherein $R^{25}$ is H, lower alkyl, substituted alkyl, aryl, substituted aryl, heteroaryl, or substituted heteroaryl;

g) CH═CH—$R^{25}$, CH═CH—$OR^{25}$, or CH═CH—$CO_2R^{25}$, having a stereochemistry of E or Z;

h) C≡C—$NR^{25}R^{26}$ or C≡CCONR$^{25}R^{26}$, wherein $R^{26}$ is defined as $R^{25}$, and $R^{25}$ and $R^{26}$ are selected independently;

i) CH═CH—$NR^{25}R^{26}$ or CH═CHCONR$^{25}R^{26}$, having a stereochemistry of E or Z, wherein $R^{25}$ and $R^{26}$ are defined as in h);

j) $(CH_2)_k R^{25}$, $(CH_2)_k$—$COOR^{25}$, or $(CH_2)_k$—$OR^{25}$, wherein k is an integer from 2 to 6;

k) $(CH_2)_k NR^{25}R^{26}$, $(CH_2)_k CONR^{25}R^{26}$, wherein $R^{25}$ and $R^{26}$ are selected independently; and l) $CH_2XR^{27}$, wherein X is O or S and $R^{27}$ is H, lowed alkyl or substituted lower alkyl, aryl, substituted aryl, heteroaryl, substituted heteroaryl;

$R^4$ is selected from the group consisting of:

m) H, lower alkyl, substituted lower alkyl, carbonyl, lower alkylcarbonyl, substituted lower alkylcarbonyl, arylcarbonyl, substituted arylcarbonyl, heterocycle, heteroarylcarbonyl, or substituted heteroarylcarbonyl;

n) $(CH_2)_k R^{28}$, $(CH_2)_k$—$COOR^{28}$, wherein k is an integer from 1 to 6, and $R^{28}$ is defined as H, lower alkyl, aryl, substituted aryl, heteroaryl, or substituted heteroaryl;

o) $(CH_2)_m XR^{29}$ wherein m is an integer from 1 to 8, X is either O or S, and $R^{29}$ is H, lower alkyl, substituted lower alkyl, acyl, carbonyl, lower alkylcarbonyl, arylcarbonyl, substituted arylcarbonyl, aryl, substituted aryl, $CH_2$-substituted aryl, heteroaryl, heterocycle, $CH_2$-substituted heterocycle, or an α- or β-antipoid sugar moiety;

p) $(CH_2)_m NR^{30}R^{31}$ wherein m is an integer from 1 to 8, and $R^{30}$ and $R^{31}$ are independently defined as $R^{29}$ above, or wherein $R^{30}$ and $R^{31}$ together are part of a heteroalkyl, substituted heteroalkyl, heteroaryl, or substituted heteroaryl ring system;

q) $(CH_2)_m XCONHR^{32}$ wherein m is an integer from 1 to 8, X is either O, S, or NH, and $R^{32}$ is defined as $R^{29}$;

r) $CH_2CH(OR^{33})CH_2OR^{34}$, wherein each $R^{33}$ and $R^{34}$ are independently defined as H, lower alkyl, substituted lower alkyl, acyl, lower alkylaminocarbonyl, arylaminocarbonyl, substituted arylaminocarbonyl, aryl, $CH_2$-substituted aryl, heterocycle, or $CH_2$-substituted heterocycle;

s) $CO(CH_2)_n R^{35}$, wherein n is an integer from 1 to 8, and $R^{35}$ is selected from the group consisting of H, halogen, aryl, substituted aryl, heterocycle, unsubstituted heterocycle, $COR^{36}$, wherein $R^{36}$ is selected from the group consisting of H, lower alkyl, substituted lower alkyl, acyl, carbamoyl, lower alkylaminocarbonyl, arylaminocarbonyl, substituted arylaminocarbonyl, aryl, $CH_2$-substituted aryl, heterocycle, and $CH_2$-substituted heterocycle, and $CONR^{37}R^{38}$, wherein $R^{37}$ and $R^{38}$ are independently selected from $R^{29}$, or $R^{37}$ and $R^{38}$ together comprise a heteroalkyl, substituted heteroalkyl, heteroaryl, or substituted heteroaryl ring system;

t) $CO(CH_2)_n^{39}$, where n is an integer of 1–8, X is selected from O and S, and $R^{39}$ is defined as $R^{36}$;

u) CONH—$R^{100}$, wherein $R^{100}$ is alkyl, substituted alkyl, aryl, substituted aryl, heteroaryl, or substituted heteroaryl;

v) $COCR^{40}R^{41}R^{42}$, wherein $R^{40}$ is H or lower alkyl, and where $R^{41}$ and $R^{42}$ together comprise a substituted alkyl or substituted heteroalkyl ring system;

w) $SO_2R^{43}$, wherein $R^{43}$ is selected from the group consisting of hydroxyl, aryl, substituted aryl, heteroaryl, substituted heteroaryl, $(CH_2)_p H$, $(CH_2)_p OH$, and $(CH_2)_p R^{44}$, wherein p is an integer from 1 to 8, and $R^{44}$ is either $OR^{45}$, wherein $R^{45}$, is defined as $R^{29}$, or $NR^{46}R^{47}$, wherein $R^{46}$ and $R^{47}$ are independently defined as $R^{29}$;

x) a sugar comprising from 1 to 5 α- or β-antipoid sugar moieties, or a combination of substituted α- or β-antipoid sugar moieties;

y) a polypeptide chain of between 1 and 10 amino acids, comprising protected or unprotected D- or L-amino acids, being attached to carbazole nitrogen at the carboxy terminus of the polypeptide chain; and yy)

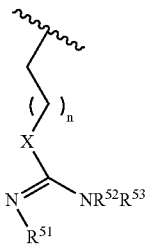

wherein X=O, S, or NH, and $R^{51}$ is H, $R^{52}$ and $R^{53}$ are independently chosen from the group consisting of H, alkyl, substituted alkyl, arly, substituted aryl, heteroaryl, substituter heteroaryl, or $R^{51}$ and $R^{52}$ are combined to form a heteroalky, substituted heteroalkyl, heteroaryl, or substituted heteroaryl ring system;

$R^5$ is selected from the group consisting of z), aa) and bb):
z) a lone pair when $X^5$ is S or N;
aa) when $X^5$ is C, a substitution pattern according to any one of a) through y); and
bb)

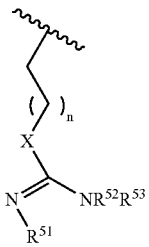

wherein X=O, S, or NH, and $R^{51}$ is H, $R^{52}$ and $R^{53}$ are independently chosen from the group consisting of H, alkyl, substituted alkyl, arly, substituted aryl, heteroaryl, substituter heteroaryl, or $R^{51}$ and $R^{52}$ are combined to form a heteroalky, substituted heteroalkyl, heteroaryl, or substituted heteroaryl ring system; or $R^4$ and $R^5$ together are part of a substituted or unsubstituted alkyl, alkenyl, heteroalkyl or heteroalkenyl ring system, said ring system having from 5 to 7 ring members in formula II and 7-9 ring members in formula I, a beteroatom of said ring system being selected from N, O or S; substitution patterns of said ring system being selected from the group consisting of a) through y), wherein at least one carbon of said ring system is unsubstituted; and wherein in formula I, when $A^1$ and $A^2$, and $B^1$ and $B^2$, respectively combine to form oxygen, $R^1$–$R^3$ and $R^5$–$R^8$ are H, and $R^4$ is H or $CH_3$, at least one of $X^1$–$X^9$ represents a ring member other than carbon.

Notably, within the structure of formula I or II, up to two of the outer ring members of either indole benzene rings, at positions $X^1$ to $X^4$ and $X^6$ to $X^9$ may be N. Thus, each of the two indole/indoline benzene rings may have zero, one or two N present at any of the outer four positions.

Ring Substitution and Derivatives of 3-(1H-Indol-3-yl)-1H-Pyrrole-2,5-Dione

Disclosed herein are pharmaceutically active ring-substitution and structural derivatives of 3-(indol-3-yl)-1H-pyrrole-2,5-diones represented by formula III:

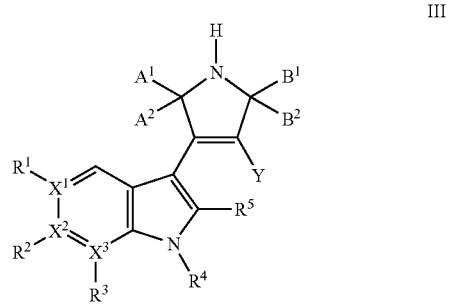

III or a pharmaceutically acceptable salt thereof wherein:
$A^1$ is H of lower alkyl, $A^2$ is H, $OR^{20}$, or $SR^{20}$, having S or R stereochemistry, wherein $R^{20}$ represents H, lower alkyl, aryl, substituted aryl, heteroaryl, or substituted heteroaryl; or $A^1$ and $A^2$ are combined to represent oxygen;

$B^1$ is H or lower alkyl, and $B^2$ is H, $OR^{20}$, or $SR^{20}$, having S or R stereochemistry; or $B^1$ and $B^2$ are combined to represent oxygen or sulfur;

$X^1$–$X^3$ are independently C or N; wherein not more than two of $X^1$, $X^2$ and $X^3$ is N;

Y is hydrogen, halogen, hydroxide, or lower alkyl;

$R^1$, $R^2$, and $R^3$ represent a lone pair or O when $X^1$, $X^2$ and $X^3$, respectively, is N;

$R^1$, $R^2$, $R^3$ (when $X^1$, $X^2$ and $X^3$, are C, respectively) and $R^5$ are independently selected from the group consisting of:
a) H, lower alkyl, lower substituted alkyl, higher alkyl, halogen, azido, cyano, nitro, or $NR^{21}R^{22}$, wherein $R^{21}$ represents H or lower alkyl, and $R^{22}$ represents H, lower alkyl, acyl, formyl, lower alkylcarbonyl, substituted lower alkylcarbonyl, carbonyl, arylcarbonyl, substituted arylcarbonyl, heterocycle, heteroarylcarbonyl, substituted heteroarylcarbonyl, lower alkylaminocarbonyl, arylaminocarbonyl, or substituted arylaminocarbonyl;
b) $OR^{23}$, wherein $R^{23}$ is H, acyl, carbonyl, lower alkylcarbonyl, substituted lower alkylcarbonyl, arylcarbonyl, or substituted arylcarbonyl;
c) $SR^{23}$;
d) $O(CH_2)_j$—$R^{24}$, $O(CH_2)_j$—O—$R^{24}$, or $O(CH_2)_j$—S—$R^{24}$, wherein j is an integer from 1 to 8, and $R^{24}$ is selected from the group consisting of H, lower alkyl, substituted lower alkyl, aryl, substituted aryl, heteroaryl, or substituted heteroaryl;
e) $S(CH_2)_jR^{24}$, $S(CH_2)_j$—O—$R^{24}$, or $S(CH_2)_j$—S—$R^{24}$;
f) C≡C—$R^{25}$, C≡C—$OR^{25}$, or C≡C—$CO_2R^{25}$, wherein $R^{25}$ is H, lower alkyl, substituted alkyl, aryl, substituted aryl, heteroaryl, or substituted heteroaryl;
g) CH=CH—$R^{25}$, CH=CH—$OR^{25}$, or CH=CH—$CO_2R^{25}$, having a stereochemistry of E or Z;
h) C≡C—$NR^{25}R^{26}$ or C≡CCONR$^{25}R^{26}$, wherein $R^{26}$ is defined as $R^{25}$, and $R^{25}$ and $R^{26}$ are selected independently;
i) CH=CH—$NR^{25}R^{26}$ or CH=CHCONR$^{25}R^{26}$, having a stereochemistry of E or Z, wherein $R^{25}$ and $R^{26}$ are defined as in h);
j) $(CH_2)_kR^{25}$, $(CH_2)_k$—COOR$^{25}$, or $(CH_2)_k$—OR$^{25}$, wherein k is an integer from 2 to 6;

k) $(CH_2)_kNR^{25}R^{26}$, $(CH_2)_kCONR^{25}R^{26}$, wherein $R^{25}$ and $R^{26}$ are selected independently; and l) $CH_2XR^{27}$, wherein X is O or S, and $R^{27}$ is H, lowed alkyl or substituted lower alkyl, aryl, substituted aryl, heteroaryl, substituted heteroaryl;

$R^4$ is selected from the group consisting of:

m) H, lower alkyl, substituted lower alkyl, carbonyl, lower alkylcarbonyl, substituted lower alkylcarbonyl, arylcarbonyl, substituted arylcarbonyl, heterocycle, heteroarylcarbonyl, or substituted heteroarylcarbonyl;

n) $(CH_2)_kR^{28}$, $(CH_2)_k$—$COOR^{28}$, wherein k is an integer from 1 to 6, and $R^{28}$ is defined as H, lower alkyl, aryl, substituted aryl, heteroaryl, or substituted heteroaryl;

o) $(CH_2)_mXR^{29}$ wherein m is an integer from 1 to 8, X is either O or S, and $R^{29}$ is H, lower alkyl, substituted lower alkyl, acyl, carbonyl, lower alkylcarbonyl, arylcarbonyl, substituted arylcarbonyl, aryl, substituted aryl, $CH_2$-substituted aryl, heteroaryl, heterocycle, $CH_2$-substituted heterocycle, or an α- or β-antipoid sugar moiety;

p) $(CH_2)_mNR^{30}R^{31}$ wherein m is an integer from 1 to 8, and $R^{30}$ and $R^{31}$ are independently defined as $R^{29}$ above, or wherein $R^{30}$ and $R^{31}$ together are part of a heteroalkyl, substituted heteroalkyl, heteroaryl, or substituted heteroaryl ring system;

q) $(CH_2)_mXCONHR^{32}$ wherein m is an integer from 1 to 8, X is either O, S, or NH, and $R^{32}$ is defined as $R^{29}$;

r) $CH_2CH(OR^{33})CH_2OR^{34}$, wherein each $R^{33}$ and $R^{34}$ are independently defined as H, lower alkyl, substituted lower alkyl, acyl, lower alkylaminocarbonyl, arylaminocarbonyl, substituted arylaminocarbonyl, aryl, $CH_2$-substituted aryl, heterocycle, or $CH_2$-substituted heterocycle;

s) $CO(CH_2)_nR^{35}$, wherein n is an integer from 1 to 8, and $R^{35}$ is selected from the group consisting of H, halogen, aryl, substituted aryl, heterocycle, unsubstituted heterocycle, $COR^{36}$, wherein $R^{36}$ is selected from the group consisting of H, lower alkyl, substituted lower alkyl, acyl, carbamoyl, lower alkylaminocarbonyl, arylaminocarbonyl, substituted arylaminocarbonyl, aryl, $CH_2$-substituted aryl, heterocycle, and $CH_2$-substituted heterocycle, and $CONR^{37}R^{38}$, wherein $R^{37}$ and $R^{38}$ are independently selected from $R^{29}$, or $R^{37}$ and $R^{38}$ together comprise a heteroalkyl, substituted heteroalkyl, heteroaryl, or substituted heteroaryl ring system;

t) $CO(CH_2)_nXR^{39}$, where n is an integer of 1-8, X is selected from O and S, and $R^{39}$ is defined as $R^{36}$;

u) $CONH$-$R^{100}$, wherein $R^{100}$ is alkyl, substituted alkyl, aryl, substituted aryl, heteroaryl, or substituted heteroaryl;

v) $COCR^{40}R^{41}R^{42}$, wherein $R^{40}$ is H or lower alkyl, and where $R^{41}$ and $R^{42}$ together comprise a substituted alkyl or substituted heteroalkyl ring system;

w) $SO_2R^{43}$, wherein $R^{43}$ is selected from the group consisting of hydroxyl, aryl, substituted aryl, heteroaryl, substituted heteroaryl, $(CH_2)_pH$, $(CH_2)_pOH$, and $(CH_2)_pR^{44}$, wherein p is an integer from 1 to 8, and $R^{44}$ is either $OR^{45}$, wherein $R^{45}$, is defined as $R^{29}$, or $NR^{46}R^{47}$ wherein $R^{46}$ and $R^{47}$ are independently defined as $R^{29}$;

x) a sugar comprising from 1 to 5 α- or β-antipoid sugar moieties, or a combination of substituted α- or β-antipoid sugar moieties;

y) a polypeptide chain of between 1 to 10 amino acids, comprising protected or unprotected D- or L-amino acids, attached to carbazole nitrogen at the carboxy terminus of the polypeptide chain; and yy)

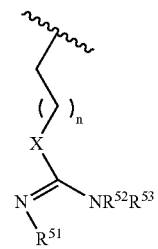

wherein X=O, S, or NH, and $R^{51}$ is H, $R^{52}$ and $R^{53}$ are independently chosen from the group consisting of H, alkyl, substituted alkyl, arly, substituted aryl, heteroaryl, substituter heteroaryl, or $R^{51}$ and $R^{52}$ are combined to form a heteroalky, substituted heteroalkyl, heteroaryl, or substituted heteroaryl ring system.

Notably, within the structure of formula III, any of the outer three positions of the indole benzene (denoted as $X^1$ to $X^3$) may be C or N. Thus, the indole benzene may have zero, one or two N present at any of these three positions. The compounds represented by formula I, II, or III are hereinafter interchangeably referred to as Compound I, II or m, respectively.

Pharmaceutically Acceptable Salts

Pharmaceutically acceptable salts of formula I, II, and III may be any salt such as an acid salt, a basic salt or a neutral salt. For example, a salt may be prepared by the direct protonation of a nitrogen found at any of positions $X^1$–$X^9$ in formulas I and II, or $X^1$–$X^3$ in formula II with a pharmaceutically acceptable acid; or by the protonation of a basic nitrogen found at any of positions $R^1$–$R^9$ of formula I and II, or $R^1$–$R^5$ or Y of formula III, with a pharmaceutically acceptable acid. These basic nitrogens are exemplified by primary, secondary, or tertiary amines, and heteroaryl moieties containing nitrogen, exemplified by pyridyl and quinolinyl ring systems.

Pharmaceutically acceptable salts of formula I, II, and III may be prepared by the treatment of an acidic moiety found in a position such as $R^1$–$R^9$ of formula I and II, or $R^1$–$R^5$ or Y of formula III, with a pharmaceutically acceptable base. These acidic moieties are exemplified by carboxylic, sulfonic, and boronic acids.

Pharmaceutically acceptable acid and basic salts are exemplified herein.

Substituent Definitions

In the definitions of the functional groups of formula I, II, and III, lower alkyl means a straight-chain or branched alkyl group having 1 to 8 carbon atoms, such as methyl, ethyl, propyl, iso-propyl, n-butyl, iso-butyl, sec-butyl, tert-butyl, pentyl, iso-amyl, neopentyl, 1-ethylpropyl, hexyl, and octyl. The lower alkyl moiety of lower alkoxy, lower alkylsulfonyl, lower alkoxylcarbonyl, lower alkylaminocarbonyl has the same meaning as lower alkyl defined above. The acyl moiety of the acyl and the acyloxy group means a straight-chain or branched alkanoyl group having 1 to 6 carbon atoms, such as formyl, acetyl, propanoyl, butyryl, valeryl, pivaloyl and hexanoyl, and arylcarbonyl group described below, or a heteroarylcarbonyl group described below. The aryl moiety of the aryl, the arylcarbonyl and arylaminocarbonyl groups means a group having 6 to 12 carbon atoms such as phenyl, biphenyl, or naphthyl. The heteroaryl moiety of the heteroarylcarbonyl groups contain at least one hetero atom selected from O, N, and S, and includes pyridyl, pyrimidyl, pyrroleyl, furyl, thienyl, imidazolyl, triazolyl, quinolyl, iso-quinolyl, benzoimidazolyl, thiazolyl, and benzothiazolyl. The aralkyl moiety of the aralkyl and the aralkyloxy groups having 7 to 15 carbon atoms, such as benzyl, pheriethyl, benzhydryl, and naphthylmethyl. The substituted lower alkyl group has 1 to 3 independently selected substitutuents, such as hydroxyl, lower alkyloxy, carboxyl, lower alkylcarbonyl, nitro, amino, mono- or di-lower alkylamino, dioxolane, dioxane, dithiolane, and dithione. The lower alkyl moiety of the substituted lower alkyl, and the lower alkyl moeity of the lower alkoxy, the lower alkoxycarbonyl, and the mono- and di-lower alkylamino in the substituents of the substituted lower alkyl group have the same meaning as lower alkyl defined above. By $CH_2$-substituted, it is meant that the substituent is present on a $CH_2$ carbon.

As used herein, the following terms denote functional groups: Me=methyl, Bn=benzyl, Ph=phenyl, $^t$Bu=t-butyl, Ac=acetyl, Ts=tosyl, pyr=pyruvate, Phth=phthalate, Et=ethyl, Boc=tert-butoxycarbonyl, Th=thiazyl, dansyl=1-(5-(dimethylamino)napthyl), cat=catalytic amount, DMAP=dimethylaminoaminopyridine, Piv=pivavoyl, Pf=pentafluorophenyl, and DIC=diisopropylcarbodiimide.

The substituted aryl, the substituted heteroaryl and the substituted araLkyl groups each may have from 1 to 3 independently-selected substitutents, such as lower alkyl, hydroxy, lower alkoxy, carboxy, lower alkoxycarbonyl, nitro, amino, mono or di-lower alkylamino, and halogen. The lower alkyl moiety of the lower alkyl, the lower alkoxy, the lower alkylamino, and the mono- and di-lower alkylamino groups among the susbtituents has the same meaning as lower alkyl defined above. The heterocyclic group formed with a nitrogen atom includes pyrroleyl, piperidinyl, piperidino, morpholinyl, morpholino, thiomorpholino, N-methylpiperazinyl, indolyl, and isoindolyl. The cycloalkyl moeity means a cycloalkyl group of the indicated number of carbon atoms, containing one or more rings anywhere in the structure, such as cycloalkyl groups include cyclopropyl, cyclopropylmethyl, cyclobutyl, cyclopentyl, cyclohexyl, 2-norbornyl, and 1-damantyl. The lower fluoroalkyl moiety means a lower fluoroalkyl group in which one or more hydrogens of the corresponding lower alkyl group, as defined above, is replaced by a fluorine atom, such as $CH_2F$, $CHF_2$, $CF_3$, $CH_2CF_3$. The α-amino acids include alanine, aminobutyric acid, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, as well as other amino acids which may occur naturally, or which can be derived from naturally occurring amino acids. The amino acids may be in the L-form, or the D-form, or in the form of racemates. The polypeptide groups include any linear combination of the above α-amino acids. Halogen includes fluorine, chlorine, bromine, and iodine.

Some of the compounds described herein contain one or more chiral centres and may thus give rise to diastereomers and optical isomers. The present invention is meant to comprehend such diastereomers as well as their racemic, resolved and enantiomerically pure forms, and pharmaceutically acceptable salts thereof.

Some of the compounds described herein contain olefmic double bonds, and unless specified otherwise, are meant to include both E and Z isomers.

Neuroprotective Profile of Compounds According to Formulas I, II, and III

The following section summarizes the biological profiles of the compounds defined as formula I through III, in cultured CNS-derived cerebral granule neurons (CGN), neuroblastoma cell lines SHSY-5Y and LAN5, and cortical cell lines, treated with various pro-apoptotic triggers.

The compounds defined by formula I through III protect CGNs against several pro-apoptotic triggers, including high/low potassium (HK/LK), β-amyloid (Aβ) fibril formation, ceramide, glutamate, and cisplatin. Additionally, these compounds down regulate the dramatic increase in caspase induction observed during HK/LK treatments, suggesting they prevent cell death by interfering in the apoptotic cascade at a point upstream of the caspases, ie. the inhibition of one or several of the serine/threonine protein kinases directly upstream of the caspases, typified by MEKK1, MKL, JNK, and $P_{53}$.

Cultured CGNs which are maintained in a medium containing 26 mM potassium (high $K^+$ or HK) undergo cell death when the medium is changed to one containing 5 mM potassium (low $K^+$ or LK). HK maintains the cells in a highly polarized state, duplicating that of fully innervated neurons. The switch to LK (5 mM is more representative of physiological conditions) results in depolarization of the cells, mimicking the loss of neuronal conductivity. Cell death under these conditions displays typical features of apoptotic cell death, both in morphology and in the upregulation of various killer genes including c-jun and caspases 1 and 3 (Ikeuchi, T. *Hum. Cell*, 1998, 11, 125). As these killer genes are turned on by various types of neuronal insult as observed in AD, PD, and stroke, HK/LK is a general in vitro model for neuronal degradation, blanketing a wide range of neurodegenerative diseases. Compounds that protect against HK/LK in CGNs would therefore be efficacious in treatment and/or prevention of various neurodegenerative disease states.

The inventive compounds inhibit HK/LK apoptotic cell death in CGNs with selected compounds protecting upwards of 100% of the neurons at 10 μm drug concentrations with $IC_{50}$ values in the range of 1–10 μM (see Example 112). K252a and CEP 1347 displayed $IC_{50}$ values of 0.3 and 1 μM, respectively. These compounds, however, were toxic at higher doses, while the compounds listed in Example 112 displayed little or no toxicity in untreated controls.

Caspase 3 expression is potently induced during in vitro HK/LK killing of CGNs. At concentrations of 10 μM (which corresponds to 75–100% protection of CGN neurons), compounds 42 and 64 significantly inhibited caspase 3 induction by 50% and 33%, respectively. Caspase 3 induction ultimately leads to cell death and is observed in any number of neurodegenerative diseases. Compounds which inhibit caspase 3 induction represent potent therapies for various neurodegenerative diseases.

Extracellular Aβ fibril formation has been found to be toxic to neurons, and represents one trigger for apoptotic death in AD. Various mechanisms have been put forward in order to account for the neurotoxicity related to extracellular Aβ fibril formation. Some of these include altered enzyme activity and disrupted calcium homeostasis leading to calpain and caspase activation (Chan, S. L, Mattson, M. P. *J. Neurosci. Res.*, 1999, 58, 167), increased free radical formation, and more recently, Aβ has been shown to interact with various receptor sites and to physically insert into the cell membrane (Kanfer, J. N. et al. *Neurochem Res.*, 1999, 24, 1621). Regardless of the mode of action, extracellular Aβ fibril formation acts as an effective apoptotic trigger for neuronal cells and serves as an in vitro model for various neurodegenerative diseases characterized by extracellular protein fibril formation, typified by diseases such as AD and PD.

Linear Aβ rapidly aggregates in CGN cultures, leading to the apoptotic cell death of approximately 50% of the neurons after 5 days. Addition of selected compounds of the formula I through III saves upwards of 100% of these cells at drug concentrations of 10 µM with $IC_{50}$ values of 1–10 µM (Example 113). These compounds may be added to the CGN culture 24 hours prior to linear Aβ addition or at the time of linear Aβ addition. Similar saves were observed under these two scenarios. The most active compounds displayed limited toxicity, less than 5%, in their respective in vitro controls. As observed in the HKILK assays, CEP 1347 displayed limited protection (>10% at concentrations below 300 nM) and severe toxicity at concentrations greater than 300 nM.

Ceramide is a native protein found in most mammalian and human cells. The upregulation of endogenous ceramide has been linked to caspase 1 (ICE) induced apoptosis (Suzuki, A. et al. Exp. Cel. Res., 1997, 233, 41). In a similar fashion, the addition of ceramide to cultured CGNs results in caspase induced apoptosis, and is therefore considered an effective in vitro model for the various neurodegenerative diseases described above, which are characterized by caspase induced apoptosis, as observed in stroke models. Addition of selected compounds of the formula I through III, 24 hours prior to the addition of ceramide, to cultured CGNs provided protection against apoptosis, with 10 to 20% of the cells being saved at 1–10 µM drug concentrations (see Example 114).

Glutaminergic neurons secrete the neurotransmitter glutamate as a part of normal cell signaling processes. Intracellular glutamate levels are regulated by glial cell uptake and conversion to glutamine. Under conditions of oxidative stress, as observed in various neurodegenerative diseases such as stroke, ALS, PD, and HD, glutaminergic neurons release massive amounts of glutamate into the intracellular fluid, overwhelming the surrounding cells. Stimulation of both NMDA and non NMDA-type glutamate excitory receptors leads to sustained depolarization of postsynaptic dendrosomal membranes, increased membrane permeability, and impaired ion homeostasis, all leading to either apoptotic or necrotic cell death.

Addition of selected compounds of the formula I through III, either at the time of glutamate addition or 24 hours prior to the addition of ceramide, to cultured CGNs provided protection against neuronal cell death, with up to 20% of the cells being saved at 1–10 µM drug concentrations (Example 115).

Cisplatin has been used extensively in the treatment of various cancers. One dosblimiting side effect of this chemotherapeutic agent is related to hearing loss as a result of its toxicity to auditory neurons and loss of feeling in the extremities. Cisplatin induces apoptosis to both cultured CGN and cortical neurons. Melatonin has been shown to protect auditory neurons during cisplatin treatments in vivo, and this combination therapy is currently in clinical trial. We have shown that at high doses melatonin will also protect CGNs, suggesting that protection of CGNs may serve as an in vitro model for cisplatin induced neuropathies.

Addition of selected compounds of the formula I through III, 24 hours prior to the addition of cisplatin (25 µg/mL), to cultured CGNs protected against neuronal apoptosis (see Example 116). Compounds 35 and 36 displayed $IC_{50}$ of 100 nM (80% survival at 300 nM) against cisplatin induced apoptosis in CGNs. Several other compounds of the formula I through III displayed $IC_{50}$ values in the range of 3–10 µM, with upwards of 80% neuronal survival. In contrast CEP 1347 displayed limited protection (>30%) at 1 µM.

Cisplatin also induces apoptosis in primary cortical neurons. Compounds 51 and 52 protected 20 and 40%, respectively, of the cultured cortical neurons at concentrations of 10 µM. Compounds 35 and 36 protected 10% of neurons. CEP 1347 protected 35% of these neurons at 0.3 µM. These compounds represent novel therapies for the prevention of neuronal damage caused by DNA damaging chemotherapeutic agents (see Example 117).

Cultured Superiour Cervical Ganglion (SCG) neurons of the PNS which have been sustained in media containing Neuron Growth Factor (NGF) undergo apoptotic cell death upon removal of the NGF from the cellular medium. Loss of neuronal trofin support has been implicated in various neurodegenerative disease states in the PNS, such as diabetic neuropathy and neuropahies related to chemotherapeutic and anti-HIV drug treatment.

Compounds of the formula I through III protect SCG neurons against NGF withdrawal when applied at concentration of 10–20 µM (see Example 118). The disclosed compounds are therefore useful in the treatment of various periferal neuropathies.

Anti-Cancer Profile of Compounds Defined by Formulas I, II, and III

Regardless of its neuroprotective capability, if a compound interferes with chemotherapy by protecting cancer cells from an apoptotic stimuli then the compound is of less value as an anti-cancer therapeutic. Compound 36 according to the invention displayed good protection of CGNs to cisplatin induced apoptosis ($IC_{50}$=100 nM). Additionally, this compound did not protect cisplatin sensitive OV 2008 ovarian cancer cells from cisplatin (20 µg/mL) induced apoptosis.

Etoposide is a well known chemotherapeutic which is toxic to several neuronal cell lines, including CGNs. Etoposide is a topoisomerase I inhibitor which induces cellular apoptosis by the inhibition of regular cell cycle progression and DNA fragmentation. As discussed above, compounds disclosed herein are neuroprotective to various apoptotic insults. Ideally, these compounds will not interfere with chemotherapeutic treatments by protect cancer cells from the same insult.

SHSY-5Y cells are members of a neuroblastoma cell line. When SHSY-5Ys were pretreated for 24 hours with selected compounds of the formula I through III, followed by etoposide, little or no protection was observed (see Example 119). This is a very positive result as etoposide, like cisplatin, is a widely used chemotherapeutic agent, and protection against etoposide kills in cancer cells would be detrimental to chemotherapy. As various topoisomerase I inhibitors are currently in clinical trial as anti-cancer agents, it is clear that concurrent administration of selected compounds of the formula I through III with specific topoisomerase I inhibitors will not interfere with the topoisomerase I induced cell death in cancer cells.

HAIP 1 and 2 are members of the IAPs which we have shown to be involved in apoptotic regulation in various cancer cell lines. Down-regulation of these proteins, both at the translational and protein levels, presents a novel means of inducing apoptosis in cancer cells.

Selected compounds of the formula I to II down-regulate the endogenous levels of HIAP1 mRNA found in the neuroblastomal cell line LAN5. mRNA levels were observed to drop by as much as 80% after 24 hours treatments of the respective cell lines with selected compounds of the formula I to III, as compared to control. These compounds represent new chemotherapeutics for treatment of cancer.

The term "subject" or "patient" as used herein refers to any mammal including humans, primates, horses, cows, pigs, sheep, goats, dogs, cats and rodents.

The pharmaceutical compositions of the invention are administered to subjects so as to deliver the compound of formula I to II in an effective amount. An effective amount means that amount necessary to delay the onset of, inhibit the progression of, halt altogether the onset or progression of, or diagnose the particular condition or symptoms of the particular condition being treated. In general, an effective amount for treating a neurological disorder is that amount necessary to affect any symptom or indicator of the condition. In general, an effective amount for treating cancer will be that amount necessary to favorably affect mammalian cancer cell proliferation in situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. Advantageously, a maximum dose is used, that is, the highest safe dose according to sound medical judgment.

A variety of administration routes are available. The particular mode selected will depend, of course, upon the particular condition being treated, the particular compound selected, the severity of the condition being treated, and the dosage required for therapeutic efficacy. The methods of this invention, generally speaking, may be practiced using any mode of administration that is medically acceptable, meaning any mode that produces effective levels of the compounds of any of formulas I to III without causing clinically unacceptable adverse effects. Such modes of administration include oral, rectal, sublingual, topical, nasal, transdermal, intradermal or parenteral routes. The term "parenteral" includes subcutaneous, intravenous, intramuscular, or infusion. Oral routes are advantageous because of the ease with which a subject can ingest an oral dosage form.

Dosage levels may be adjusted appropriately to achieve desired levels of a compound of formula I to III, either locally or systemically. Generally, a daily oral dose of a compound of formula I to III will be from about 0.01 mg/kg per day to 1000 mg/kg per day. Three doses per day, each in the range of about 1 to 1000 mg/m$^2$ per day would be effective. In the event that the response in a subject is insufficient at such doses, even higher doses (or effective higher doses by a different, more localized delivery route) may be employed to the extent that a subject's tolerance permits.

The compositions containing compounds according to the invention may conveniently be presented in unit dosage form and may be prepared by any of the methods well known in the art of pharmacy. All methods include the step of bringing the compounds of the invention into association with a carrier that constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the compound of formula I to III. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the compounds of formula I to III, thereby increasing convenience to the subject and the physician. Many types of release delivery systems are available and known to those of ordinary skill in the art. They include polymer based systems such as polylactic and polyglycolic acid, polyanhydrides and polycaproiactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

When administered, the compositions according to the invention may contain other pharmaceutically acceptable components. Such compositions may contain salts, buffering agents, preservatives, compatible carriers, and optionally other therapeutic ingredients. When used in medicine the salts should be pharmaceutically acceptable, but non-pharmaceutically acceptable salts may be used in synthetic reactions to prepare pharmaceutically acceptable salts therefrom, and are not excluded from the scope of the invention. Such salts include, but are not limited to, those prepared from the following acids: hydrochloric, hydrobromic, sulphuric, nitric, phosphoric, maleic, acetic, salicylic, p-toluenesulfonic, tartaric, citric, methane sulfonic, formic, malonic, succinic, naphthalene2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and salts thereof (1–2% W/V); citric acid and salts thereof (1–3% W/V); and phosphoric acid and salts thereof (0.8–2% W/V), as well as others known in the art. Suitable preservatives include benzalkonium chloride (0.003–0.03% W/V); chlorobutanol (0.3–0.9% W/V); parabens (0.01–0.25% W/V) and thimerosal (0.004–0.02% W/V), as well as others known in the art. Suitable carriers are pharmaceutically acceptable carriers. The term pharmaceutically acceptable carrier means one or more compatible solid or liquid filler, dilutents or encapsulating substances that are suitable for administration to a human or other mammal. The term "carrier" denotes an organic or inorganic ingredient, natural or synthetic, with which the active ingredient is combined to facilitate the application. The components of the pharmaceutically acceptable carrier are capable of being commingled with the molecules of the compounds of formula I to III of the present invention, and with each other, in a manner such that there is no interaction which would substantially impair the desired pharmaceutical efficacy. Carrier formulations suitable for oral, subcutaneous, intravenous, and intramuscular administration etc., are those known in the art.

The compounds of the invention may be delivered with other therapeutic agents. The invention additionally includes co-administration of any of the compounds of formula I to III with other compounds known to be useful in treating neurodegenerative diseases, typified by but not limited to, acetylcholinesterase inhibitors for treatind AD such as tacrine, doneprizil, and rivastigmin, and L-dopa for treating PD.

Compounds of formulas I to III have been shown to protect CGNs and cortical neurons to cisplatin induced apoptosis. This protection extends to the protection of other CNS and peripheral neurons to various neurotoxins and chemotherapeutic agents which induce CNS and/or peripheral neurotoxicity.

In the case of peripheral neuropathy induced by a toxic agent, the compounds I through III are delivered separately before, simultaneously with (ie. in the form of anti-cancer coctails, as described in further detail below), or after exposure to the toxic agent. Optionally, compounds of formula I through III and the neurotoxic or chemotherapeutic agent are each administered at effective time intervals, during an overlapping period of treatment in order to prevent or restore at least a portion of the neurofunction destroyed by the neurotoxic or chemotherapeutic agent. The chemotherapetic agent can be any causing neurotoxicity, such as dideoxyinosine, cisplatin, etoposide, vincristine, or taxol.

By "toxic agent" or "neurotoxic agent" is meant a substance that through its chemical action injures, impairs, or inhibits the activity of a component of the nervous system. The list of neurotoxic agents that cause neuropathies is lengthy (see a list of neurotoxic agents provided in Table 1). Such neurotoxic agents include, but are not limited to, neoplastic agents such as vincristine, vinblastine, cisplatin, taxol, or dideoxy-compounds, eg., dideoxyinosine; alcohol; metals; industrial toxins involved in occupational or environmental exposure; contaminants in food or medicinals; or over doses of vitamines or therapeutic drugs, eg. Antibiotics such as penicillin or chloramphenicol, or mega-doses of vitamins A, D, or B6.

TABLE 1

| Neurotoxic Agents | |
| --- | --- |
| AGENT | ACTIVITY |
| actazolimide | Diuretic |
| acrylamide | flocculant, grouting agent |
| adriamycin | Antineoplastic |
| alcohol (ie. ethanol) | solvent, recreational drug |
| almitine | respiratory stimulant |
| amiodarone | Antiarrthymic |
| amphotericin | Antimicrobial |
| arsenic | herbicide, insecticide |
| aurothioglucose | Antirheumatic |
| barbiturates | anticonvulsive, sedative |
| buckthorn | toxic berry |
| carbimates | Insecticide |
| carbon disulfide | industrial applications |
| chloramphenicol | Antibacterial |
| chloroquine | Antimalarial |
| chlorestyramine | Antihyperlipoproteinemic |
| cisplatin | Antineoplastic |
| clioquinol | amebicide, antibacterial |
| colestipol | Antihyperlipoproteinemic |
| colchicine | gout suppressant |
| colistin | Antimicrobial |
| cycloserine | Antibacterial |
| cytarabine | Antineoplastic |
| dapsone | dermatological ie- leprosy |
| dideoxycytidine | Anatineoplastic |
| dideoxyinosine | Antineoplastic |
| dideoxythymidine | Antiviral |
| disulfiram | Antialcohol |
| doxorubicin | Antineoplastic |
| ethambutol | Antibacterial |
| ethionamide | Antibacterial |
| glutethimide | sedative, hypnotic |
| gold | Antirheumatic |
| hexacarbons | Solvents |
| hormonal contraceptives | |
| hexamethylolmelamine | fireprooing, crease proofing |
| hydralazine | Antihypertensive |
| hydroxychloroquine | Antirheumatic |
| imipramine | antidepressant |
| indolmethacin | anti-inflammatory |
| inorganic lead | toxic metal in paint, etc. |
| iso-niazid | antituberculousis |
| lithium | antidepressant |
| methylmercury | industrial waste |
| metformin | antidiabetic |
| methylhydrazine | synthetic intermediate |
| metronidazole | antiprotozoal |
| misonidazole | radiosensitizer |

TABLE 1-continued

| Neurotoxic Agents | |
| --- | --- |
| AGENT | ACTIVITY |
| nitrofurantoin | urinary antiseptic |
| nitrogen mustard | antineoplastic, nerve gas |
| nitous oxide | anesthetic |
| organophosphates | insecticides |
| ospolot | anticonvulsant |
| penicillin | antibacterial |
| perhexiline | antiarrhythmic |
| perhexiline maleate | antiarrythmic |
| phenytoin | anticonvulsant |
| platnim | drug component |
| primidone | anticonvulsant |
| procarbazine | antineoplastic |
| pyridoxine | vitamin B6 |
| sodium cyanate | antisickling |
| streptomycin | antimicrobial |
| sulphonamides | antimicrobial |
| suramin | anteneoplastic |
| tamoxifen | antineoplastic |
| taxol | antineoplastic |
| thalidomide | antileprous |
| thallium | rat poison |
| triamterene | diuretic |
| trimethyltin | toxic metal |
| L-trypophan | health food additive |
| vincristine | Antineoplastic |
| vinblastine | Antineoplastic |
| vindesine | Antineoplastic |
| vitamine A or D | mega doses |

In the case of cancer, the compounds would be delivered separately or in the form of anti-cancer cocktails. An anti-cancer cocktail is a mixture of any one of the compounds having formula I to III with another anti-cancer agent such as an anti-cancer drug, a cytokine, and/or supplementary potentiating agent(s). The use of cocktails in the treatment of cancer is routine. In this embodiment, a common administration vehicle (e.g., pill, tablet, implant, injectable solution, etc.) could contain both a compound of formula I to III and the anti-cancer drug and/or supplementary potentiating agent.

Thus, cocktails comprising of formula I through III compounds as well as other compounds are within the scope of the invention. Compounds having anti-neoplastic properties include, but are not limited to: Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanin; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emiteftir; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormiaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based inmmune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating agents include: tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca$^{2+}$ antagonists (e.g., yerapamil, nifedipine, nitrendipine and caroverine); calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

The compounds of the invention also can be administered with cytokines such as granulocyte colony stimulating factor or anti-sense oligonucleotides targeting survival proteins such as, but not limited to, Bcl-2, HIAP1, HIAP2, XIAP or surviving.

The conjugates of the invention also are useful, in general, for treating mammalian cell, proliferative disorders other than cancer, including psoriasis, actinic keratosis, etc.

The use of any of the compounds having the structure of formula I-III for treatrnent and/or prevention of neuological disorders, cancer, inflammation, or symptoms related thereto is also encompassed by the invention.

EXAMPLES

Examples of compounds according to formula I are provided in Table 2, based on the compound of formula IV (a subset of formula I), provided below. The compound numbering used in Table 2 to identify exemplary compounds is made reference to consistently herein for all subsequent examples. For the structures in which $X^5$ is noted as meaning CH, this is consistent with formula I $X^5$—$R^5$, wherein $X^5$ is C and $R^5$ is H.

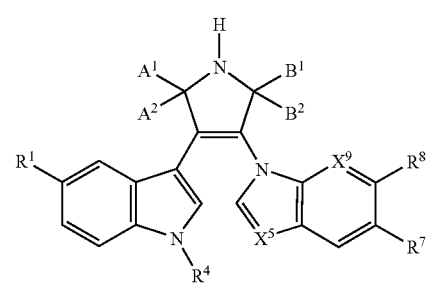

IV

TABLE 2

Exemplary Structures of Formula VI, a Subset of Formula I

| Compound | A$^1$/A$^2$ | B$^1$/B$^2$ | R$^1$ | R$^4$ | R$^7$ | R$^8$ | X$^5$ | X$^9$ |
|---|---|---|---|---|---|---|---|---|
| 1 | O | O | H | H | H | H | CH | CH |
| 2 | O | O | MeO | H | H | H | CH | CH |
| 3 | O | O | H | H | MeO | H | CH | CH |
| 4 | O | O | MeO | H | MeO | H | CH | CH |
| 5 | O | O | BnO | H | H | H | CH | CH |
| 6 | O | O | BnO | CH$_2$CH$_2$OH | H | H | CH | CH |
| 7 | O | O | BnO | CH$_2$CH$_2$OH | MeO | H | CH | CH |
| 8 | O | O | BnO | CH$_2$CH$_2$OH | H | MeO | CH | CH |
| 9 | O | O | BnO | H | H | MeO | CH | CH |
| 10 | O | O | H | CH$_2$CH$_2$OH | H | H | CH | CH |
| 11 | O | O | BnO | H | BnO | H | CH | CH |
| 12 | O | O | H | H | BnO | H | CH | CH |
| 13 | O | O | Br | H | H | H | CH | CH |
| 14 | O | O | I | H | H | H | CH | CH |
| 15 | O | O | PhC≡C | H | H | H | CH | CH |
| 16 | O | O | PhCH$_2$CH$_2$ | H | H | H | CH | CH |
| 17 | O | O | H | H | H | H | N | CH |
| 18 | O | O | H | CO$_2^t$Bu | H | H | N | CH |
| 19 | O | O | H | COCH$_3$ | H | H | N | CH |
| 20 | O | O | H | CON(H)Ph | H | H | N | CH |
| 21 | O | O | BnO | H | H | H | N | CH |
| 22 | O | O | H | H | H | H | CH | N |
| 23 | O | O | H | CO$_2^t$Bu | H | H | CH | N |

Examples of compounds according to formula II, having a single bond between carbon "a" and $X^5$ are provided in Table 3, based on the compound of formula V (a subset of Formula II), provided below. The compound numbering used in Table 3 to identify exemplary compounds is made reference to consistently herein for all subsequent examples. $X^5$ is noted as meaning $CH_2$ within this structure, which is consistent with formula II as $X^5$—$R^5$, wherein $X^5$ is CH and $R^5$ is H.

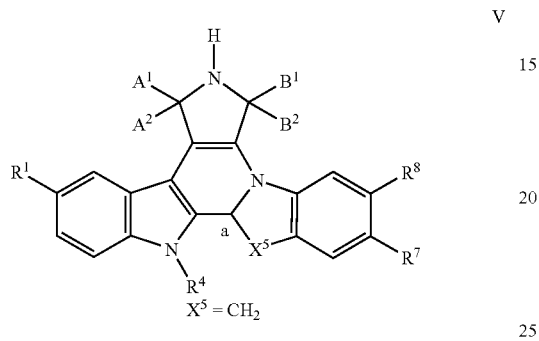

V $X^5 = CH_2$

TABLE 3

Exemplary Structures of Formula V, a Subset of Formula II

| Compound | $A^1/A^2$ | $B^1/B^2$ | $R^1$ | $R^4$ | $R^7$ | $R^8$ |
|---|---|---|---|---|---|---|
| 24 | O | O | H | H | H | H |
| 25 | rac-H/OH | O | H | H | H | H |
| 26 | O | rac-H/OH | H | H | H | H |
| 27 | H/H | O | H | H | H | H |
| 28 | O | H/H | H | H | H | H |
| 29 | O | O | H | $CO_2^tBu$ | H | H |
| 30 | rac-H/OH | O | H | $CO_2^tBu$ | H | H |
| 31 | O | rac-H/OH | H | $CO_2^tBu$ | H | H |
| 32 | H/H | O | H | $CO_2^tBu$ | H | H |
| 33 | O | H/H | H | $CO_2^tBu$ | H | H |
| 34 | O | O | H | H | MeO | H |
| 35 | O | O | BnO | H | H | H |
| 36 | O | O | BnO | $CH_2CH_2OH$ | H | H |
| 37 | O | O | BnO | $CH_2CH_2OC(O)CH_2OAc$ | H | H |
| 38 | O | O | BnO | $CH_2CH_2OH$ | MeO | H |
| 39 | O | O | BnO | $CH_2CH_2OH$ | H | MeO |
| 40 | O | O | H | $CH_2CH_2OH$ | H | H |
| 41 | O | O | H | H | BnO | H |

Examples of compounds according to formula II, having a double bond between carbon "a" and $X^5$ are provided in Table 4, based on the compound of formula VI (a subset of Formula II), provided below. The compound numbering used in Table 4 to identify exemplary compounds is made reference to consistently herein for all subsequent examples. $X^5$ is noted as meaning CH within this structure, which is consistent with formula II as $X^5$—$R^5$, wherein $X^5$ is C and $R^5$ is H.

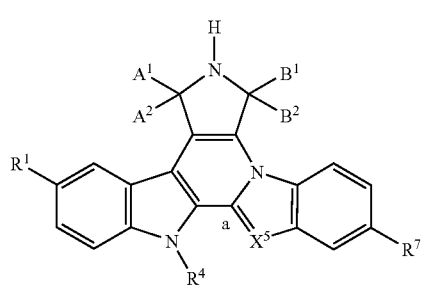

VI

TABLE 4

Exemplary Structures of Formula VI, a subset of Formula II

| Compound | $A^1/A^2$ | $B^1/B^2$ | $R^1$ | $R^4$ | $R^7$ | $X^5$ |
|---|---|---|---|---|---|---|
| 42 | O | O | H | H | H | CH |
| 43 | O | rac-H/OH | H | H | H | CH |
| 44 | rac-H/OH | O | H | H | H | CH |
| 45 | O | H/H | H | H | H | CH |
| 46 | H/H | O | H | H | H | CH |
| 47 | O | O | MeO | H | H | CH |
| 48 | O | O | H | H | MeO | CH |
| 49 | O | O | MeO | H | MeO | CH |
| 50 | O | O | MeO | $COCH_2N(H)CO_2{}^tBu$ | H | CH |
| 51 | O | O | MeO | $COCH_2OC(O)CH_3$ | H | CH |
| 52 | O | O | BnO | H | H | CH |
| 53 | O | O | H | H | H | N |
| 54 | O | O | H | $COCH_3$ | H | N |
| 55 | O | O | H | $CO_2{}^tBu$ | H | N |

Examples of compounds according to formula III are provided in Table 5, based on the compound of formula VII (a subset of Formula III), provided below. The compound numbering used in Table 5 to identify exemplary compounds is made reference to consistently herein for all subsequent examples. Relative to formula III, the structures according to formula VII have ring members $X^1$, $X^2$ and $X^3$ represented by C (ring member $X^3$ of formula III is shown as "X" in formula VII). $R^5$ is H for all exemplified compound in Table 5.

Examples of formula III are:

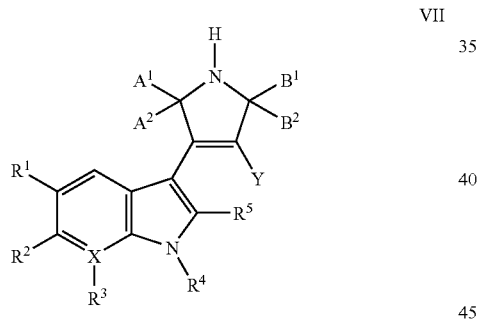

VII

TABLE 5

Exemplary Structures of Formula VII, a Subset of Formula III

| Compound | $A^1/A^2$ | $B^1/B^2$ | $R^1$ | $R^2$ | $R^3$ | $R^4$ | X | Y |
|---|---|---|---|---|---|---|---|---|
| 56 | O | O | Br | H | H | H | C | H |
| 57 | O | O | Br | H | H | —$COCH_3$ | C | H |
| 58 | O | O | Br | H | H | —$CONMe_2$ | C | H |
| 59 | O | O | Br | H | H | —COPh | C | H |
| 60 | O | O | Br | H | H | Ts | C | H |
| 61 | O | O | Br | H | H | —$SO_2(1-C_{10}H_7)$ | C | H |
| 62 | O | O | Br | H | H | —$SO_2(2-C_{10}H_7)$ | C | H |
| 63 | O | O | Br | H | H | dansyl | C | H |
| 64 | O | O | BnO | H | H | H | C | H |
| 65 | O | O | BnO | H | H | —$COCH_3$ | C | H |
| 66 | O | O | BnO | H | H | —COPh | C | H |
| 67 | O | O | BnO | H | H | —$CO(2,4-(MeO)_2Ph)$ | C | H |
| 68 | O | O | BnO | H | H | —$CO(3,4-(MeO)_2Ph)$ | C | H |
| 69 | O | O | BnO | H | H | —$COCH_2N(H)Boc$ | C | H |
| 70 | O | O | BnO | H | H | Ts | C | H |
| 71 | O | O | BnO | H | H | —$SO_2(4-(NO_2)Ph)$ | C | H |

TABLE 5-continued

Exemplary Structures of Formula VII, a Subset of Formula III

| Compound | A¹/A² | B¹/B² | R¹ | R² | R³ | R⁴ | X | Y |
|---|---|---|---|---|---|---|---|---|
| 72 | O | O | BnO | H | H | —SO₂(3-(NO₂)Ph) | C | H |
| 73 | O | O | BnO | H | H | —CH₂Ph | C | H |
| 74 | O | O | BnO | H | H | —CH₂(4-pyr) | C | H |
| 75 | O | O | BnO | H | H | —CH₂(3,5-(MeO)₂Ph) | C | H |
| 76 | O | O | BnO | H | H | 3-F(Ph)CH₂— | C | H |
| 77 | O | O | BnO | H | H | 4-F(Ph)CH₂— | C | H |
| 78 | O | O | BnO | H | H | —CH₂Phth | C | H |
| 79 | O | O | BnO | H | H | —CH₂(2-C₁₀H₇) | C | H |
| 80 | O | O | BnO | H | H | —CH₂(C₆H₁₁) | C | H |
| 81 | O | O | BnO | H | H | —CH₂(CH₂)₆CH₃ | C | H |
| 82 | O | O | BnO | H | H | —CH₂CH₂OH | C | H |
| 83 | O | O | BnO | H | H | —CH₂CH₂OAc | C | H |
| 84 | O | O | BnO | H | H | —CH₂CH₂O—CO(3,4-(MeO)₂Ph) | C | H |
| 85 | O | O | BnO | H | H | —CH₂CH₂OC(O)NHPh | C | H |
| 86 | O | O | MeO | H | H | H | C | H |
| 87 | O | O | MeO | H | H | Ts | C | H |
| 88 | O | O | MeO | H | H | —SO₂(4-(NO₂)Ph) | C | H |
| 89 | O | O | MeO | H | H | allyl | C | H |
| 90 | O | O | HO | H | H | allyl | C | H |
| 91 | O | O | HO | H | H | Ts | C | H |
| 92 | O | O | H | H | H | H | C | H |
| 93 | O | O | H | H | H | Ts | C | H |
| 94 | O | O | H | H | H | —SO₂(4-(AcNH)Ph) | C | H |
| 95 | O | O | H | H | H | —SO₂(2-(NO₂)Ph) | C | H |
| 96 | O | O | H | H | H | —SO₂(4-(NO₂)Ph) | C | H |
| 97 | O | O | H | H | H | —SO₂Th | C | H |
| 98 | O | O | H | H | H | —SO₂Bu | C | H |
| 99 | O | O | Cl | H | H | H | C | H |
| 100 | O | O | H | Cl | H | H | C | H |
| 101 | O | O | H | H | Cl | H | C | H |
| 102 | O | O | F | H | H | H | C | H |
| 103 | O | O | H | F | H | H | C | H |
| 104 | O | O | NO₂ | H | H | H | C | H |
| 105 | O | S | BnO | H | H | H | C | H |
| 106 | O | O | H | H | H | H | C | OMe |
| 107 | O | O | H | H | H | H | C | OH |
| 108 | O | O | H | H | H | Me | C | OH |

The compounds illustrated below as 109, 110 and 111 also fall within the structure of formula III. Notably, for compound 109, the group representing R⁵ is CH₂(CH₃)₂CCO₂Me.

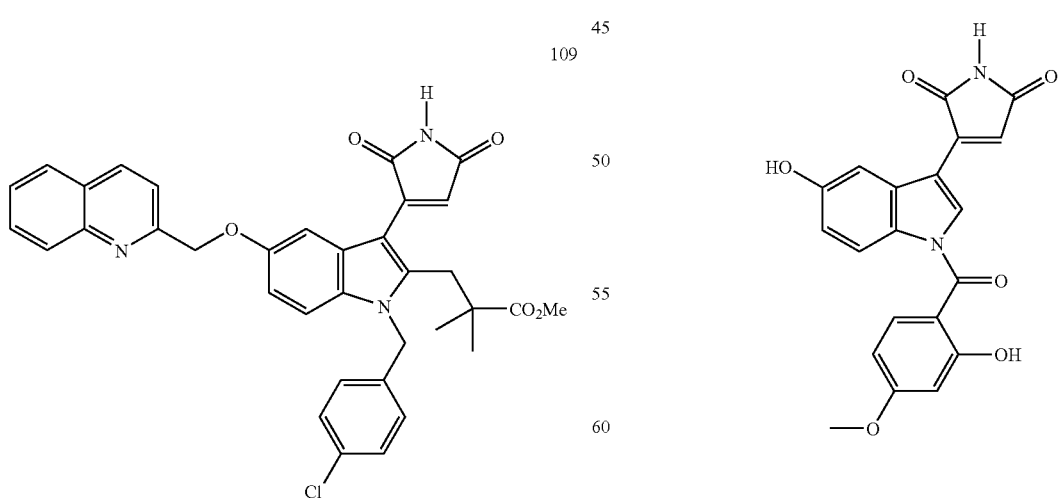

-continued

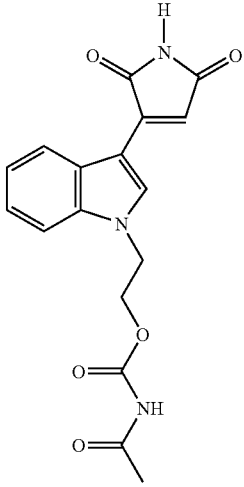
111

GENERAL PREPARATIVE METHODS

The compounds of the invention may be prepared by use of known chemical reactions and procedures. Nevertheless, the following general preparative methods are presented to aid the reader in synthesizing compounds of formula I to III. Substitution patters have been minimized for convenience except where clarification is required. However, all combinations of substitution are implicit in the methodologies outlined below.

The invention encompasses intermediates for manufacturing the compounds of formula I to III, as described herein. Mixtures including isomeric mixtures also may result depending upon the symmetry of the starting molecule. Such mixtures are within the scope of the invention.

To prepare the full range of compounds of the invention, only the chemistry described below, together with chemistry known to those of skilled in the art is required. In particular, modifications of the core structures can be accomplished using routine chemistry such as described herein.

Method A: Synthesis of 3-(indol-3-yl)-4-(1N-indolyl)-1H-pyrrole-2,5-diones

Indole, intermediate A1, is treated with oxalyl chloride, in a solvent such as THF or diethyl ether, to provide the 3-indolylglyoxalyl chloride hydrochloride salt, which is further treated with NaOMe in MeOH, to yield the methyl 3-indolylglyoxylate, intermediate B1. A second indole, A1, is converted to the acetamide intermediate C1, by stirring A1 with NaH in DMF, followed by the addition of iodoacetamide. Intermediates B1 and C1 are suspended in THF and treated with 3 to 4 equivalents of a base such as KO$^t$Bu, to provide compound 1, which falls under the general class of 3-(indol-3-yl)-4-(1N-indolyl)-1H-pyrrole-2,5-diones.

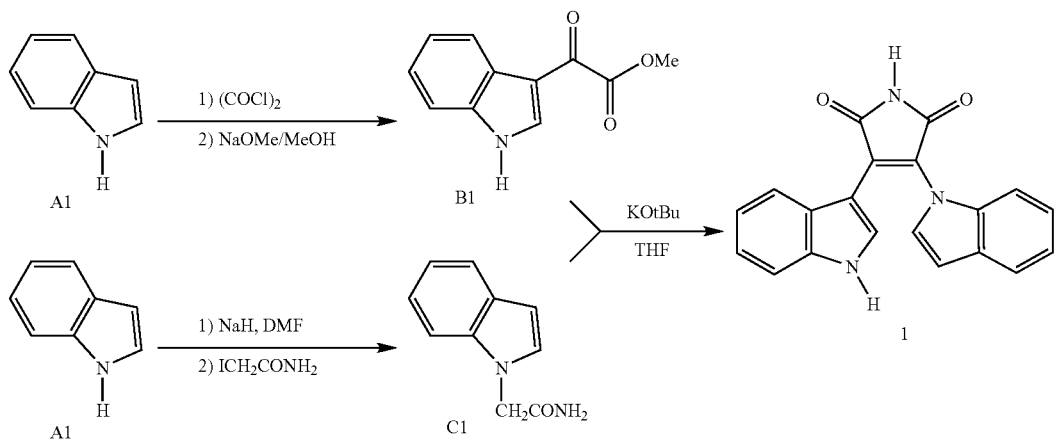

The synthesis according to Method A can be generally described by the above reactions. The invention relates to the above-noted method for preparation of 3-(indol-3-yl)-4-(1N-indolyl)-1H-pyrrole-2,5-dione compounds, said method comprising the following steps: (a) reacting indole with oxalyl choride in a solvent to form a hydrochloride salt; (b) treating said hydrochloride salt with NaOMe in alcohol to form a methyl 3-indolglyoxylate; (c) reacting indole with a strong base in a polar solvent; (d) reacting the product of step (c) with haloacetamide to form an acetamide intermediate; and (e) treating the products of steps (b) and (d) with excess base to form a 3-(indol-3-yl)-4-(1N-indolyl)-1H-pyrrole-2,5-dione. It is implicit in this method that the reactants may be substituted in such a way that the resulting compound is a 3-(indol-3-yl)-4-(1N-indolyl)-1H-pyrrole-2,5-dione, which may for example fall within the structure of formula I. Further, the product of step (e) may be further reacted to add such substituents as those noted within the structure of formula I.

Method B: Synthesis of 3-(indol-3-yl)-4-(1N-indolyl)-1H-pyrrole-2,5-diones

Intermediate A1 is treated with oxalyl chloride in a solvent such as diethyl ether or THF. The resulting 3-indolylglyoxalyl chloride hydrochloride salt is treated with aqueous ammonium carbonate to provide the acetamide intermediate D1. A second appropriately substituted indole, A1, is treated with a KO$^t$Bu, followed by ethyl bromoacetate to yield intermediate E1 (in situ). To this solution of E1 is added 1 equiv of solid D1. The resulting suspension is treated with 5 equiv of KO$^t$Bu and stirried over night. After quenching with conc $H_2SO_4$, aqueous workup and purification by silica gel chromatography, compound 1 is isolated in low yield.

($R^1$=H). When $R^1$ is MeO, compound 2, cyclization is followed by autooxidation to provide compound 47.

When $R^1$ is BnO, compound 5, $BF_3OEt_2$ is added to a TIF solution of 5, and the reaction is not stirred for more than 6 hours, to provide compound 35.

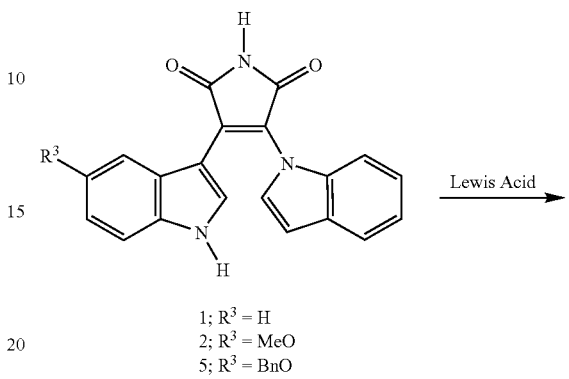

1; $R^3$ = H
2; $R^3$ = MeO
5; $R^3$ = BnO

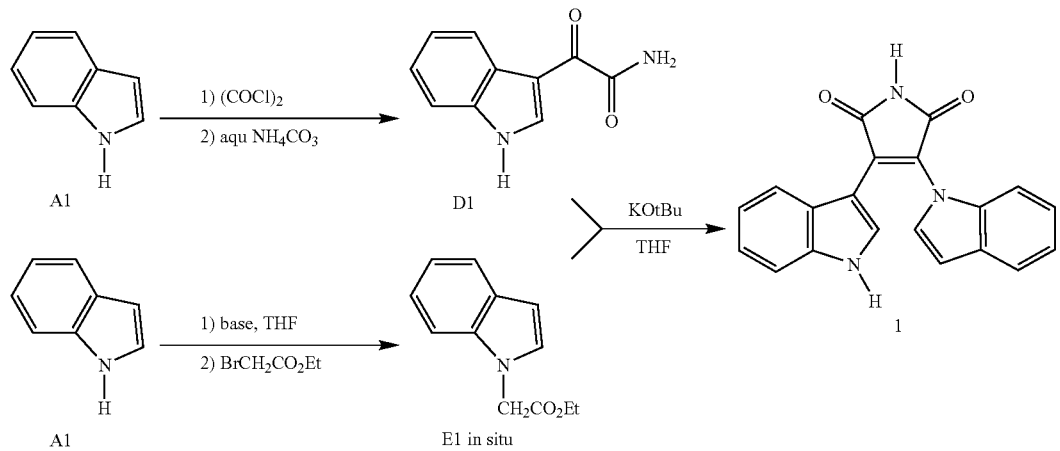

The synthesis according to Method B can be generally described by the above reactions. The invention relates to the above-noted method for preparation of 3-(indol-3-yl)-4-(1N-indolyl)-1H-pyrrole-2,5-dione compounds, said method comprising the following steps: (a) reacting indole with oxalyl choride in a solvent to form a hydrochloride salt; (b) treating said hydrochloride salt with aqueous ammonia to form an acetamide intermediate; (c) reacting indole with a base; (d) reacting the product of step (c) with haloacetate; and (e) adding an equivalent of the product of step (b) to the product of step (d) and treating with excess base to form a 3-(indol-3yl)4-(1N-indolyl)-1H-pyrrole-2,5-dione. It is implicit in this method that the reactants may be substituted in such a way that the resulting compound is a 3-(indol-3-yl)-4-(1N-indolyl)-1H-pyrrole-2,5-dione, which may for example fall within the structure of formula I. Further, the product of step (e) may be further reacted to add such substituents as those noted within the structure of formula I.

Method C: Cyclization of 3-(indol-3yl)4-(1N-indolyl)-1H-pyrrole-2,5-diones

Compound 1 ($R^1$=H) was suspended in a solvent such as methlyene chloride and treated with 1.2 equiv of TMSOTf. After stirring 0 to 24 hours the solvent is removed to provide, after silica gel chromatography, compound 24

-continued

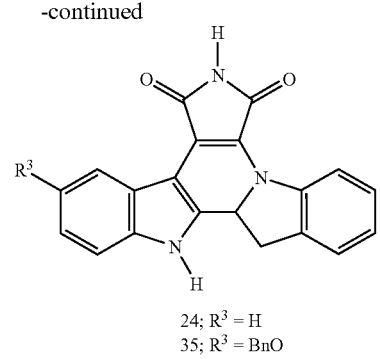

24; $R^3$ = H
35; $R^3$ = BnO

The synthesis according to Method C can be generally described by the above reactions. The invention relates to the above-noted method for cyclization of a 3-(indol-3-yl)-4-(1N-indolyl)-1H-pyrrole-2,5-dione compound, said method comprising the step of reacting a 3-(indol-3-yl)4-(1N-indolyl)-1H-pyrrole-2,5-dione with a Lewis acid to form a pyrrolo-α-hydro-β-carboline. The product of this method may fall within the structure of formula II. Further, the product of the method may be further reacted to add such substituents as those noted within the structure of formula II.

Method D: DDQ Oxidation of Dihydro-pyrrolo-β-carbolines

Compound 24 is dissolved in a solvent such as 1,4-dioxane and treated with a dioxane solution of an oxidizing agent, in this case 2,3-dichloro-5,6-dicyano-1,4-benzoquinone (DDQ) (2.2 equiv). Filtration through celite and purification by silica gel chromatography provides compound 42.

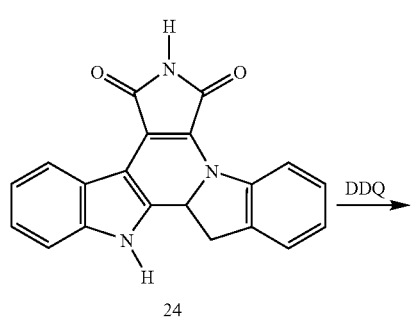

The synthesis according to Method D can be generally described by the above reaction. The invention relates to the above-noted method for oxidation of a dihydro-pyrrolo-β-carbolines, said method comprising the step of reacting a pyrrolo-α-hydro-β-carboline of formula II, having a single bond at carbon (a) with an oxidizing agent. The product of this method may fall within the structure of formula II, having a double bond at carbon (a). Further, the product of the method may be further reacted to add such substituents as those noted within the structure of formula II.

Method E: Preparation of N-Ethylhydroxy Derivatives

Intermediate A1 was converted to its N-indolyl acetic acid derivative, intermediate F1, using phase transfer catalysis. Subsequent LAH reduction to the corresponding acid, intermediate G1, and acylation provided intermediate H1. Conversion of H1 to its methyl glyoxylate, intermediate B11, followed as described above in Method A.

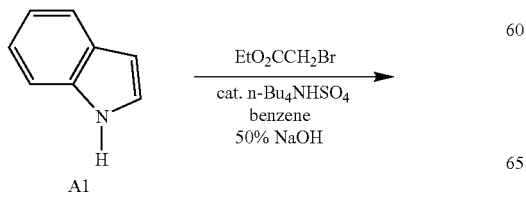

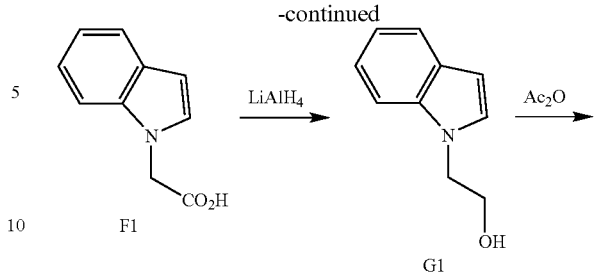

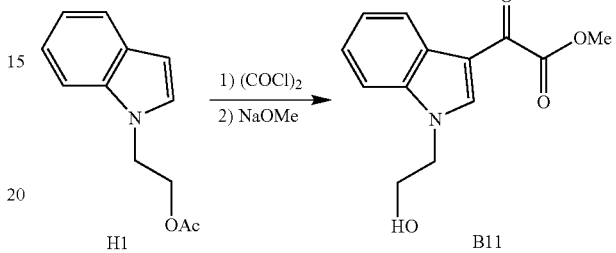

Coupling of C1 with B11, as described in method A, yielded compound 10. Cyclization of 10 using BF$_3$OEt$_2$ at −78° C., provided the desired di-hydro-β-carboline, compound 40.

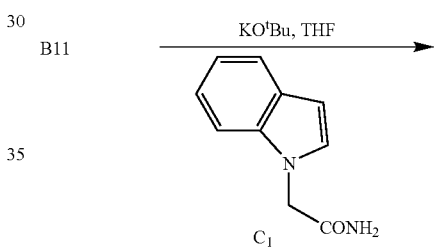

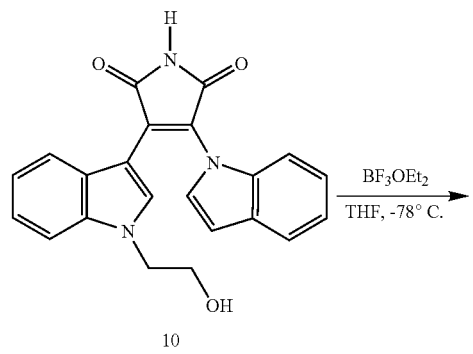

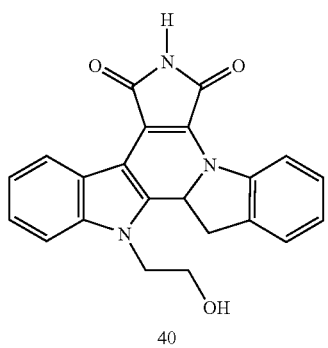

Method F: Carbonyl Reduction and Sulfonylation Reactions

Compounds 24 and 29 are readily reduced to a mixture of alcohols. Compound 24 ($R^4$=H) provides a 1:1 mixture of 25 and 26, while compound 29 (R=$CO_2^tBu$) provides a 3:1 mixture of 30 and 31. These compounds were separable by silica gel chromatography.

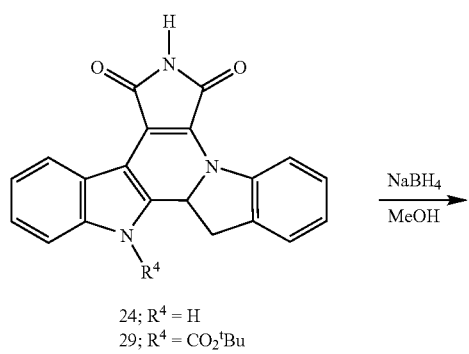

24; $R^4$ = H
29; $R^4$ = $CO_2^tBu$

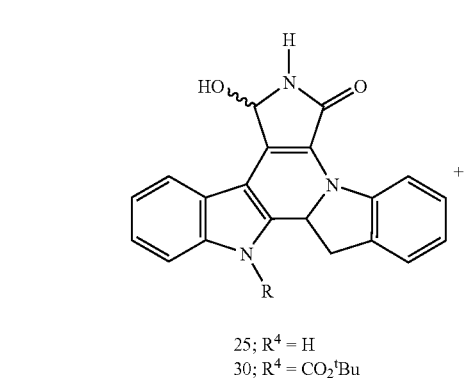

25; $R^4$ = H
30; $R^4$ = $CO_2^tBu$

26; $R^4$ = H
31; $R^4$ = $CO_2^tBu$

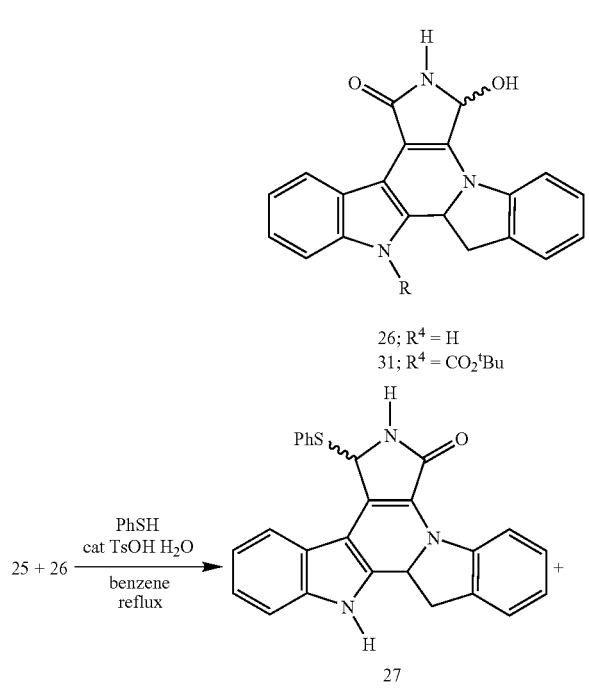

27

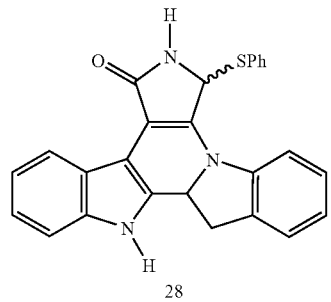

28

Treatment of either the mixture of compounds 25 and 26, or each independently, with PhSH and catalytic TsOH yields compound 27 and 28, respectively. This chemistry is also applicable to the fully oxidized β-carbolines such as compound 42.

Treatment of either the mixture of 30 and 31, or each independently, with 2 equiv of PhSeH and a catalytic amount of TsOH yields compound 32 and 33, respectively.

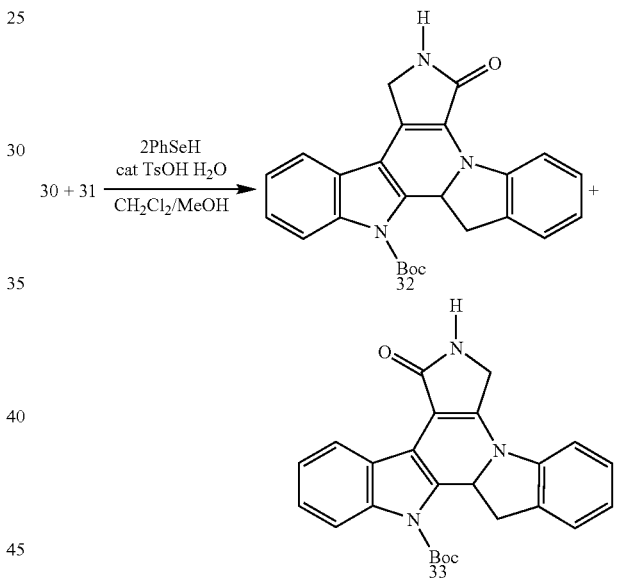

32

33

Method G: Palladium Catalyzed Indole Functionalization and Glyoxylate Formation

Intermediate A7 was prepared by the treatment of 5-iodoindole, A6, with $(Boc)_2O$. Palladium catalyzed coupling of A7 with phenylacetylene proceeded in good yields to provide intermediate A8, which was readily deprotected by photolysis in a solvent such as acetonitrile, with a 250 W light bulb, to provide intermediate A9. Conversion of A9 was to the methyl glyoxylate intermediate B9, followed as described in Method A.

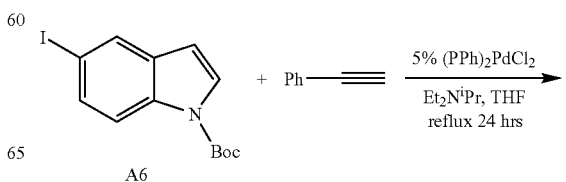

A6

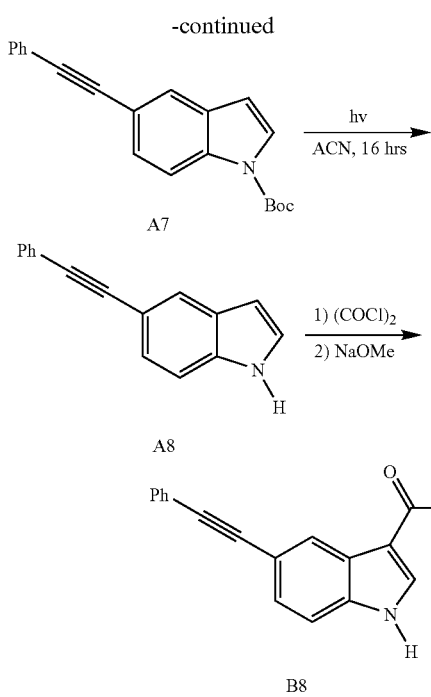

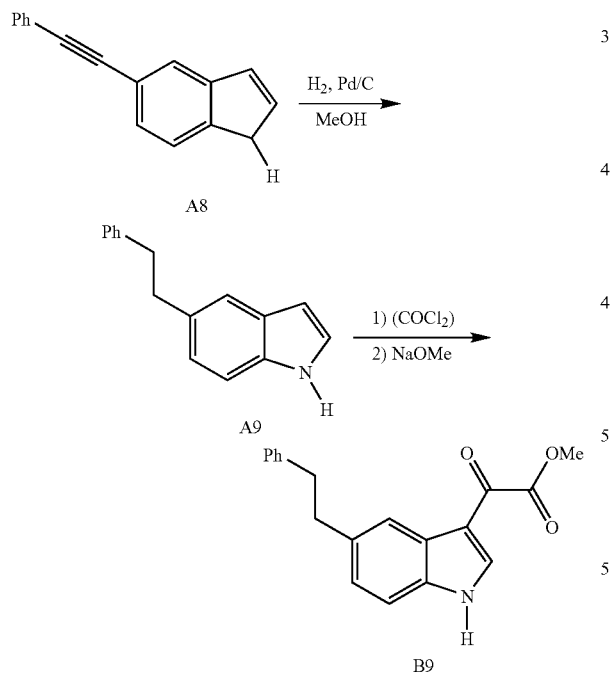

Intermediate A8 was reduced using tosylhydrazine and sodium acetate to yield intermediates A9, which was then converted to the methyl glyoxalate intermediate B9, as described in Method A.

The synthesis according to Method G can be generally described by the above reactions. The invention relates to the above-noted method for preparation of a fumctionalized methyl glyoxolate indole, the method comprising the following steps: (a) reacting N-Boc-iodoindole with an acetylene in the presence of a palladium catalyst under coupling conditions; (b) deprotecting the product of step (a) by photolysis in solvent; (c) reacting the product of step (b) with oxalyl choride to form a hydrochloride salt; and (d) forming a methyl 3-(acetyleno)indolglyoxylate by treating said hydrochloride salt with NaOMe.

The product of this reaction may be used to form functionalized compounds according to the invention, for example as an intermediate in synthetic routes described in Methods A and B, above.

Method H: Acylation of pyrrolo-β-Carboline Derivatives with α-Amino Acids

A THF solution of compound 47, Boc-Gly-OH, DIC, Et₃N, DMAP (cat) is refluxed for 24 hours. This reaction mixture is subjected to standard aqueous work up and purification by silica gel chromatography, to yield the acylated product, compound 50.

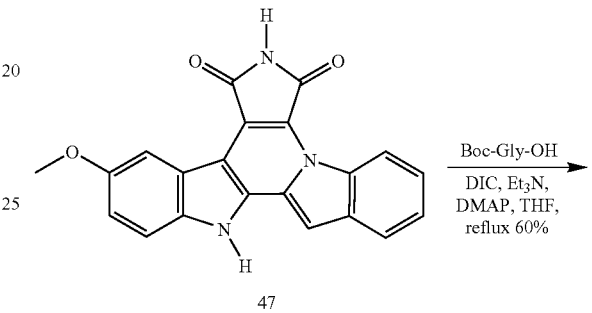

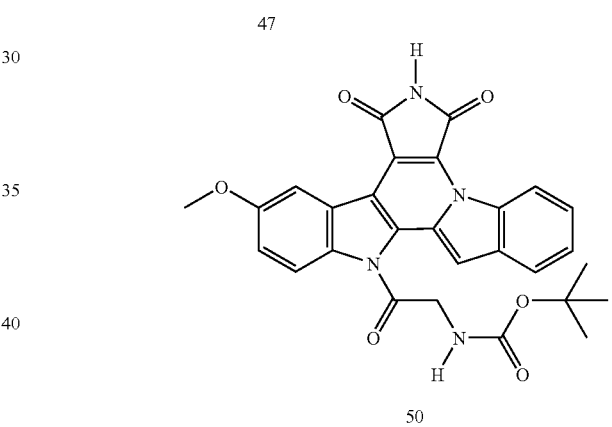

Method I: Acylation of β-Carboline Derivatives with Acid Chlorides

A THF solution of compound 47, acetoxyacetyl chloride, Et₃N, DMAP (cat) is stirred at room temperature for 24 hours. This reaction mixture is subjected to standard aqueous work up and purification by silica gel chromatography, to yield the acylated product, compound 51.

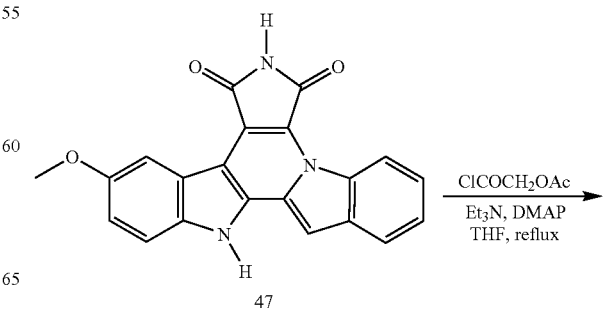

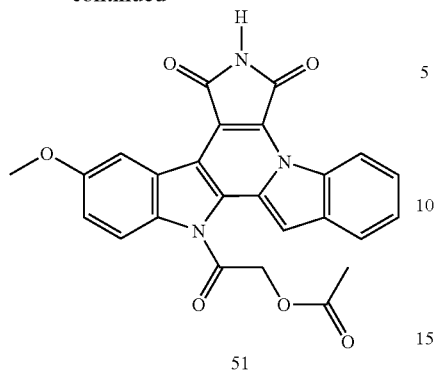

51

Method J: Synthesis of 3-(indol-3-yl)-4-(1N-benzyimidazolyl)-1H-pyrrole-2,5-diones Benzimidazole (2 equiv) was stirred overnight, in a solvent such as THF, with iodoacetamide (1 equiv) to yield acetamide I1. Acetamide I1, glyoxylate B1, $K_2CO_3$, and CETAB are susbended in benzene and refluxed for 5 days, while removing water with a Dean Stark trap. Aqueous work up and purification by silica gel chromatography yields two products, compound 17 and its methyl ester J1.

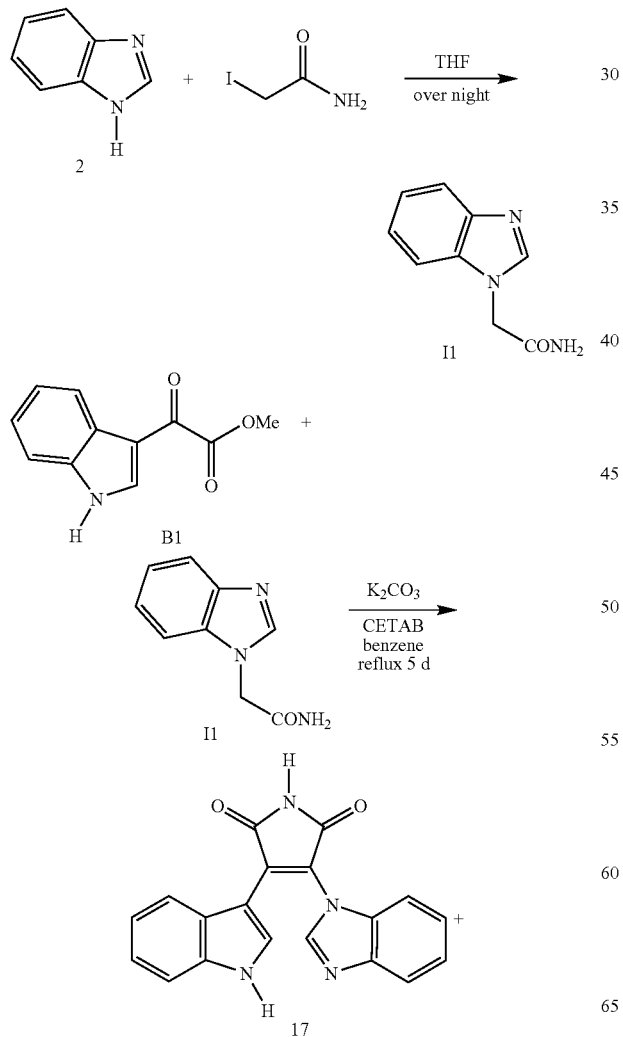

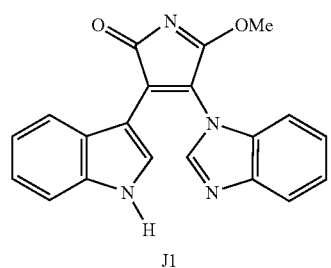

J1

Alternatively, compounds B1 and I1 may be combined in THF and treated with a THF solution of KO$^t$Bu (3 equiv). The reaction is stirred for 1 hour before aqueous workup and purification by silica gel chromatography provides 17 and variable quantities of 106.

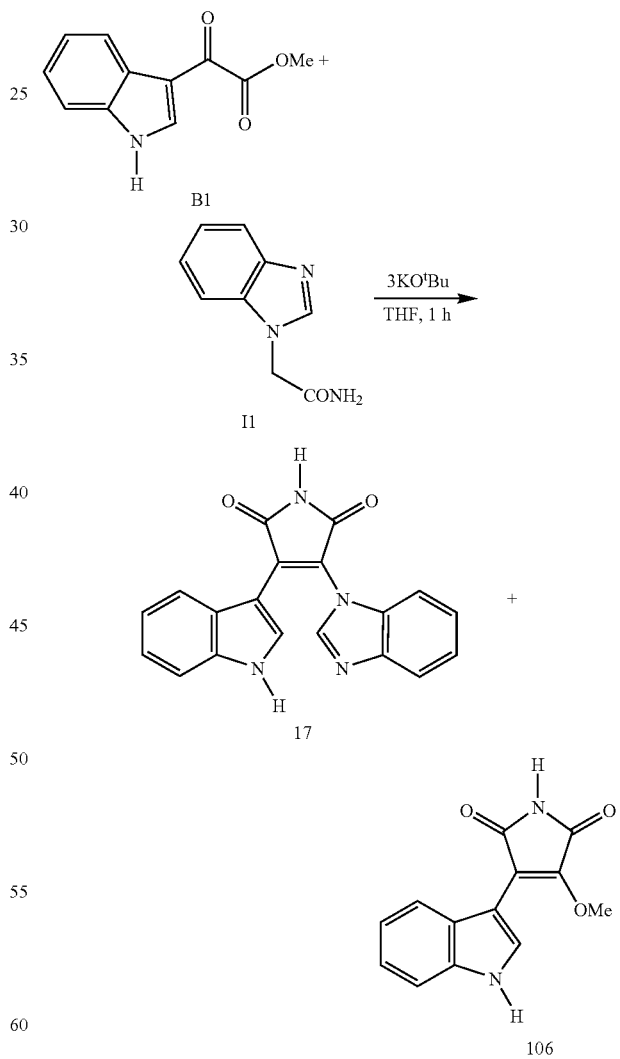

The synthesis according to Method J can be generally described by the above reactions. The invention relates to the above-noted method for preparation of 3-(indol-3-yl)-4-(1N-benzyimidazolyl)-1H-pyrrole-2,5-diones compounds, said method comprising the following steps: (a) reacting indole with oxalyl choride in a solvent to form a hydrochloride salt; (b) treating said hydrochloride salt with NaOMe in alcohol to form a methyl 3-indolglyoxylate; (c) reacting benzoimidazole with a strong base in a polar solvent; (d) reacting the product of step (c) with haloacetamide to form an acetamide intermediate; and (e) treating the products of steps (b) and (d) with excess base to form a 3-(indol-3-yl)-4-(1N-benzyimidazolyl)-1H-pyrrole-2,5-dione.

Method K: Acylation and Cyclization of 3-(indol-3-yl)-4-(1N-benzyimidazolyl)-1H-pyrrole-2,5-diones Compound 17 is readily acylated with acid chlorides, anhydrides, and isocyanates, to yield compounds 18, 19, and 20, respectively. Photolysis of compounds 18 and 19 (300 watt bulb, 48 hrs, acetonitrile) provides compounds 54 and 55, respectively. Photolysis of compound 20, as above, yields the cyclized and de-carbonylated compound 53.

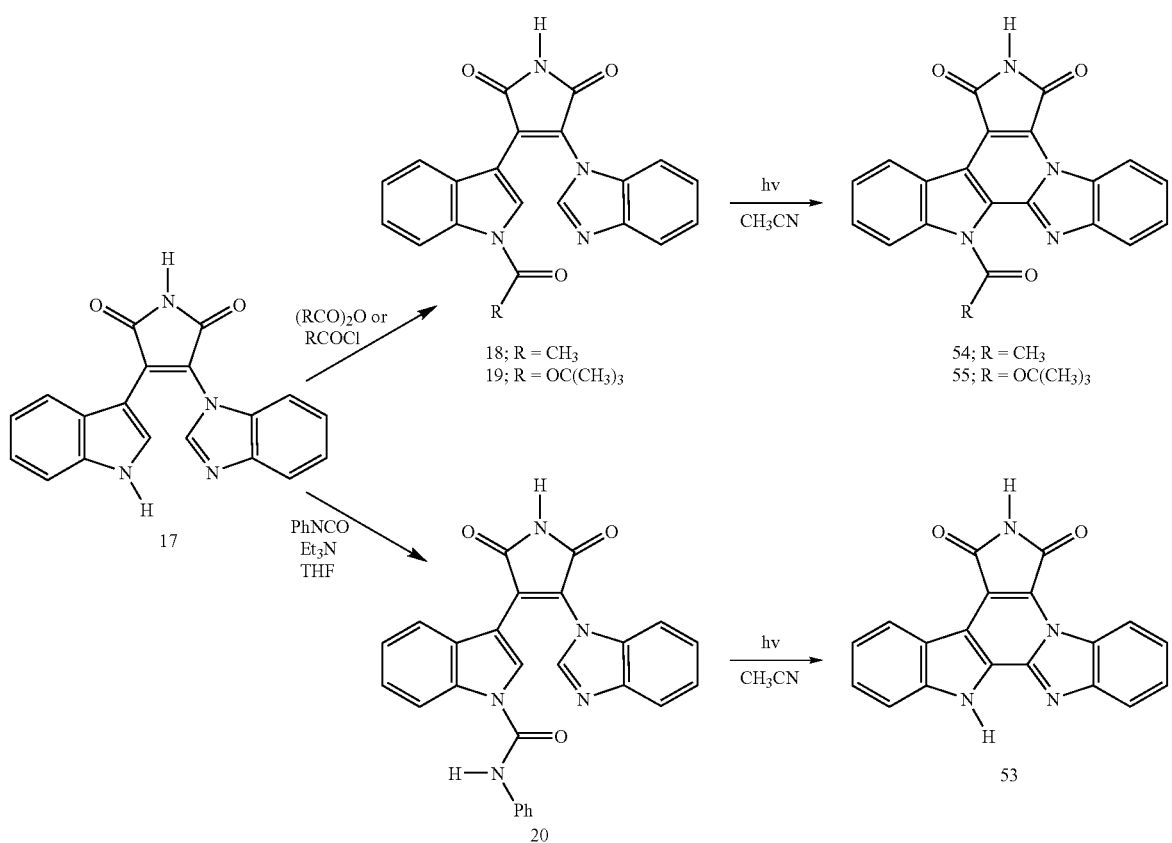

The synthesis according to Method K comprises the following methodological steps: (a) reacting 3-(indol-3-yl)-4-(1N-benzyimidazolyl)-1H-pyrrole-2,5-dione with an acylating agent selected from the group consisting of anhydride, acid chloride and isocyanate to provide 3-(N-acylindol-3-yl)-4-(1N-benzyimidazolyl)-1H-pyrrole-2,5-dione; and (b) photolysis of the product of step (a) in a solvent to form cyclization of 3-(indol-3-yl)-4-(1N-benzyimidazolyl)-1H-pyrrole-2,5-diones.

Method L: Synthesis of 3-(1-methylindol-3-yl)-4-(benzyimidazol-1-yl)-1-acetylpyrrole-2,5-dione and 3-(1-methylindol-3-yl)-4-(imidazol-1-yl)-1-acetylpyrrole-2,5-dione To a THF solution of compound 108 and a base such as triethylamine (4 equiv), is added 3 equiv of acetyl chloride.

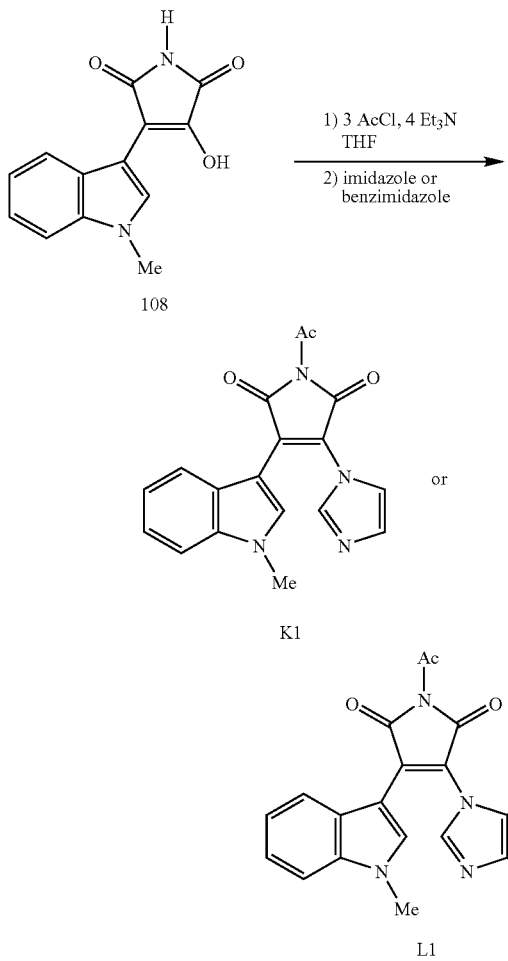

This solution is stirred for 2 hours before either imidazole or benimidazole is added. After stirring for 2 to 24 hours intermediates K1 or L1, respectively, was obtained after purification by recrystallization or silica gel chromatography.

Method M: One Pot preparation of 3-(indol-3-yl)-1H-pyrrole-2,5-diones

Indole A1 (1.0 equiv) is dissolved in a solvent such as diethyl ether or THF and treated with oxalyl chloride (1.1 equiv). After stirring at room temperature for 1 to 24 hours the volatiles are removed under reduced pressure. Acetamide (3 equiv) is added to the resulting 3-indolylglyoxalyl chloride hydrochloride salt, and this mixture is taken up in dry THF. After stiring at room temperature for 2 to 3 hours a 1.0 M THF solution of KO$^t$Bu (5 equiv) is added. Ths resulting purple solution is stirred for 3 to 24 hours before the reaction is quenched with conc $H_2SO_4$ (30 minutes at room temperature), followed by aqueous extraction and purification by recrystallization or silica gel chromatography to yield compound 92.

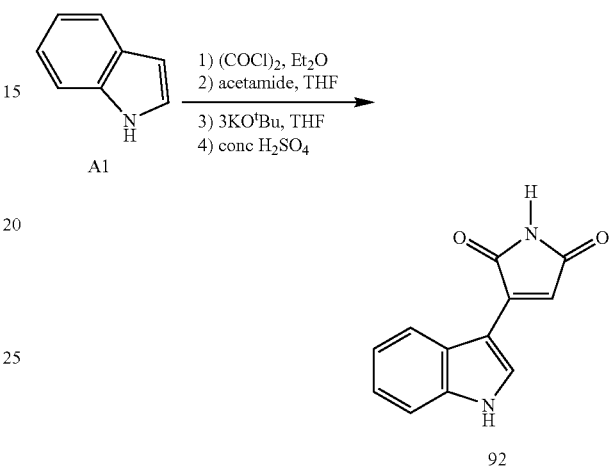

The one pot synthesis according to Method M can be generally described by the above reaction. The invention relates to the above-noted method for preparation of a 3-(indol-3-yl)-1H-pyrrole-2,5-dione compound, said method comprising the following steps: (a) dissolving indole in a solvent and treating with oxalyl chloride to form a hydrochloride salt; (b) treating said hydrochloride salt with acetamide in solvent; (c) reacting the product of step (b) with excess strong base in THF; and (d) reacting the product of step (c) with strong acid to form 3-(indol-3-yl)-1H-pyrrole-2,5-dione.

Method N: Acylation and Sulfonylation of 3-(1H-indol-3-yl)-1H-pyrrole-2,5-diones The disclosed 3-(1H-indol-3-yl)-1H-pyrrole-2,5-diones were readily acylated with a number of anhydrides, mixed anhydrides, and acid chlorides. Acylations using acetic anhydride or acetyl chloride were complete within 1 hour, however, aryl acid chlorides and mixed anyhydrides required refluxing over night in THF, with triethylamine and catalytic DMAP.

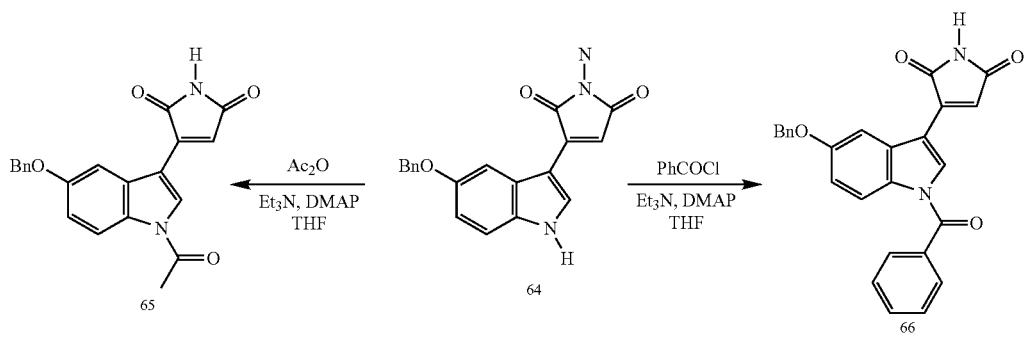

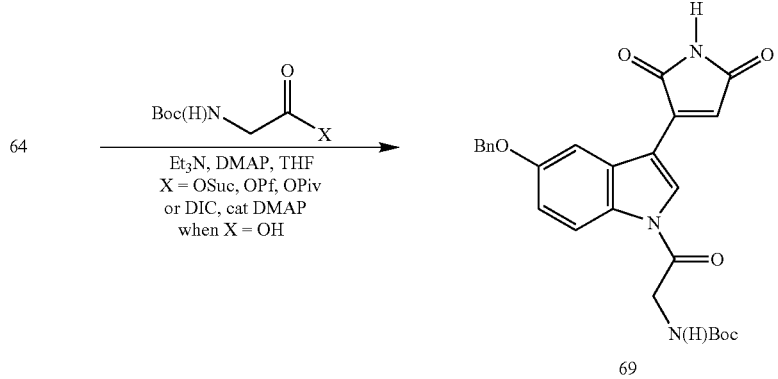

Similarly, Boc-Gly-OH couples with 64 in the presence of DIC and cat. DMAP in refluxing THF. Sulfonylation with various sulfonyl chlorides, triethylamine, and up to 2 equiv of DMAP, in THF, required refuxing for 48 hours and provided the desired sulfonamides in low to moderate yields.

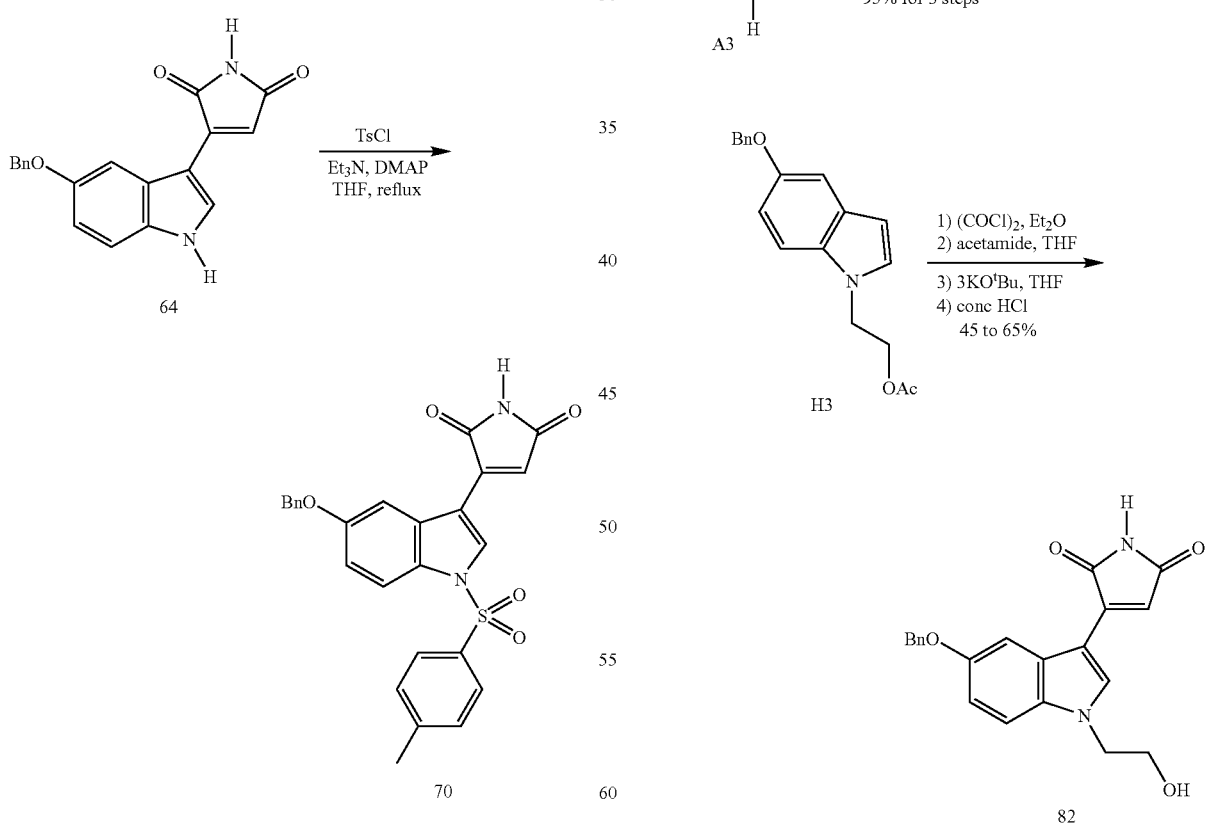

Method O: Functionalization of Compound 82

Indole A3 was converted to intermediate H3 via the three step process described in Method E. Intermediate H3 was converted to compound 82 using Method M.

Compound 82 was acylated in a similar manner as that described in Method N, to provide compounds 83 and 84. Treatment of 82 with phenylisocyanate provides compound 85.

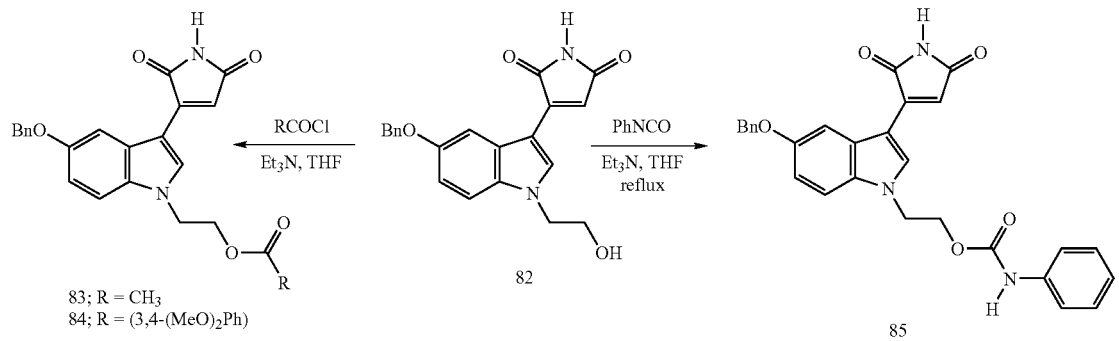

83; R = CH₃
84; R = (3,4-(MeO)₂Ph)

PREPARATIVE METTHODS FOR INTERMEDIATE COMPOUNDS

Preparation methods of intermediate compounds for synthesis of compounds of formula I to III are within the scope of the invention, as are the intermediate compounds themselves. Various commercially available indoles were used and are labled as follows; indole, intermediate A1; 5-methoxyindole, intermediate A2; 5-benzyloxyindole, intermediate A3; 5-bromoindole, intermediate A4; 5-iodoindole, intermediate A5. Exemplary Preparative methods are provided below Intermediate A6: N-Boc-5-iodoindole Di-tert-butyl dicarbonate (2.2 mL; 9.05 mmol) was added to a solution of 5iodoindole (2.00 g, 8.23 mmol) in THF (50 mL) followed by a catalytic amount of DMAP and left to stir at room temperature for 10 minutes. The reaction was diluted with ethyl acetate (200 mL), the organic solution washed with saturated ammonium chloride solution (100 mL), water (100 mL) and brine (100 mL). The organic phase was dried over anhydrous magnesium sulfate and concentrated in vacuo to yield Intermediate A6 as an off white solid, which was used without further purification. $^1$H NMR (200 MHz, CDCl$_3$) δ 7.91 (d, J=7.1 Hz, 1H), 7.88 (s, 1H), 7.59 (d, J=7.1 Hz, 1H), 7.52 (d, 2.5 Hz, 1H), 6.45 (d, J=2.5 Hz, 1H), 1.65 (s, 3H).

Intermediate A7: N-Boc-5-(2-phenethyl)indole

Pd(PPh$_3$)$_2$Cl$_2$ (288 mg, 0.411 mmol) and CuI (157 mg, 0.822 mmol) were suspended in THF (50 mL and the solution purged with N$_2$ for 10 minutes. Intermediate A6 (2.82 g, 8.22 mmol) and triethyl amine (50 mL) were added and the solution purged with N$_2$ for a further 10 minutes. Phenyl acetylene (903 μl; 8.22 mmol) was added and the reaction left to stir at room temperature for 2 hours. The solvent was removed in vacuo and the material purified by silica gel chromatography, eluting with 2:1 hexanes/ethyl acetate, to provide intermediate A7 as an off white solid (2.05 g, 78.5%). m.p. 106–107° C. $^1$H NMR (500 MHz, DMSO-d$^6$) 1.61 (9H, s), 6.72 (1H, d, J 3.7), 7.42 (3H, m), 7.48 (1H, dd, J 8.5, 1.2), 7.55 (1H, dd, J 7.7, 2.1), 7.71 (1H, d, J 3.7), 7.83 (1H, s), 8.07 (1H, d, J 8.5).

Intermediate A8: 1H-5-(2-phenethyl)indole

A solution of intermediate A7 (1.20 g, 3.78 mmol) in acetonitrile (50 mL) was placed directly above a 150 W light bulb and left for 16 hours. The solvent was removed in vacuo and the residue purified by silica gel chromatography, eluting with 3:1 hexanes/ethyl acetate, to yield intermediate A8 as a yellow solid (700 mg, 85%).

m.p. 133–135° C. $^1$H NMR (500 MHz, DMSO-d$^6$) δ 6.47 (1H, m), 7.26 (1H, dd, J 8.4, 1.5), 7.39 (4H, m), 7.44 (1H, d, J 8.4), 7.53 (2H, dd, J 8.4, 1.5), 7.79 (1H, d, J 0.6), 11.32 (1H, s).

Intermediate A9: 5-(2-phenethy)lindole

A solution of intermediate A8 (2.05 g, 6.5 mmol) and p-toluenesulfonohydrazide (12.1 g, 6.5 mmol) in 1,2-dimethoxyethane (80 mL) was heated to reflux. A solution of sodium acetate (8.9 g, 0.1 mol) in water (80 mL) was added dropwise over a period of 4 hours maintaining the reaction at reflux. The reaction was left to reflux for a further 16 hours, cooled to room temperature and poured onto water (500 mL). The solution was extracted with dichloromethane (3×300 mL), the organic extracts combined, washed with water (300 mL), dried over anhydrous magnesium sulfate and concentrated in vacuo. Purification by silica gel chromatography, eluting with 3:1 hexanes/ethyl acetate, yielded intermediate A9 as an off white solid. $^1$H NMR (200 MHz, CDCl$_3$) δ 8.03 (br s, 1H), 7.50 (s, 1H), 7.40–7.15 (m, 7H), 7.06 (dd, J=1.2, 5.0 Hz, 1H), 6.52 (s, 1H), 3.02 (s, 4H).

Intermediate B1: Methyl 3-indoleglyoxylate

Oxalyl chloride (1.50 mL; 17.2 mmol) was added dropwise to an ice cold solution of indole, A1, (2.00 g; 17.1 mmol) in anhydrous diethyl ether (20 mL). The resulting solution was allowed to stir on ice for 1 hour after which time a yellow slurry had formed. A freshly prepared solution of sodium methoxide in methanol (780 mg Na metal in 20 mL methanol; 34.1 mmol) was added, the reaction allowed to warm to room temperature and stirred for 1 hour. The reaction was quenched with the addition of water (30 mL) and the resulting orange solid isolated by fitration, washed with diethyl ether and recrystallised from methanol. Yield 2.94 g; 85%. mp 226–228° C. $^1$H NMR (500 MHz, DMSO-d$^6$) 12.40 (br s, 1H), 8.17 (dd, J=1.5, 7.6 Hz, 1H), 7.55 (dd, J=1.5, 7.6 Hz, 1H), 7.29 (dt, j=1.5, 7.6 Hz, 1H), 7.26 (dt, J=1.5, 7.6 Hz, 1H), 3.89 (s, 3H).

Intermediate B2: Methyl 5-methoxy-3-indoleglyoxylate 5-methoxy-indole (2.00 g, 13.6 mmol) was dissolved in diethyl ether and stirred at 0° C. for 15 min. Oxalyl chloride (1.30 ml) was added via syringe and the reaction stirred at RT for 3 h. During this time a precipitate formed. A solution of sodium methoxide in methanol (27.2 mmol) was then added using a syringe at −78° C. The reaction was then brought to RT and stirred for 3 h, until it was quenched with water (15 ml). A solid yellow precipitate formed, and was filtered off, before being dried in vacuo to yield intermediate B2 as a yellow solid (2.10 g, 66%). m.p. 251.6–252.7° C. $^1$H NMR (200 MHz, DMSO-d$^6$) δ 12.60 (br s, 1H), 8.35 (d, J=3.0 Hz, 1H), 7.65 (d, J=2.4 Hz, 1H), 7.46 (d, J=8.8 Hz, 1H), 6.91 (dd, J=2.6, 8.9 Hz, 1H), 3.88 (s, 1H), 3.79 (s, 1H).

Intermediate B3: Methyl 5-benzyloxy-3-indoleglyoxylate

Intermediate B3 was prepared according to the method described for Intermediate A1, using 5-benzyloxy-indole, A3, (1.91 g; 8.55 mmol), oxalyl chloride (750 µL; 8.6 mmol), 5-benzyloxy-indole, A3, (1.91 g; 8.55 mmol), anhydrous diethyl ether (10 mL), and a freshly prepared solution of sodium methoxide in methanol (390 mg Na metal in 10 mL methanol; 17.1 mmol), to yield intermediate B3 as a yellow solid (2.07 g, 78%). mp 254–255° C.

Intermediate B4: Methyl 5-bromo-3-indoleglyoxylate

Intermediate B3 was prepared according to the method described for Intermediate A1, using 5-benzyloxy-indole, A3, (1.91 g; 8.55 mmol), oxalyl chloride (750 µL; 8.6 mmol), 5-benzyloxy-indole, A3, (1.91 g; 8.55 mmol), anhydrous diethyl ether (10 mL), and a freshly prepared solution of sodium methoxide in methanol (390 mg Na metal in 10 mL methanol; 17.1 mmol), to yield intermediate B3 as a yellow solid (2.07 g, 78%). $^1$H NMR (200 MHz, DMSO-d$^6$) δ 12.66 (br s), 8.51 (dd, J=0.4, 3.3 Hz, 1H), 8.28 (s, 1H), 7.50 (t, J=7.6 Hz, 1H), 7.45 (t, J=7.6 Hz, 1H), 3.89 (t, 3H).

Intermediate B5: Methyl 5-iodo-3-indoleglyoxylate

Intermediate B5 was prepared according to the method described for Intermediate B 1, using 5-iodoindole, A5, (1.0 g, 4.11 mmol), oxalyl chloride (361 µL; 4.14 mmol), anhydrous diethyl ether (5 mL), and a freshly prepared solution of sodium methoxide in methanol 190 mg Na metal in 5 mL methanol; 8.22 mmol), to yield intermediate B5 as a yellow solid (501 mg, 37%).m.p. 280–281° C. $^1$H NMR (500 MHz, DMSO-d$^6$) δ 3.88 (3H, s), 7.40 (1H, d, J 8.6), 7.57 (1H, dd, J 8.5, 1.7), 8.44 (1H, d, J 3.3), 8.49 (1H, d, J 1.7), 12.6 (1H, br).

Intermediate B8: Methyl 5-(2-phenethyl)-3-indole glyoxylate

Intermediate B8 was prepared according to the method described for Intermediate B 1, intermediate A8 (400 mg, 1.84 mmol), oxalyl chloride (321 µL; 3.68 mmol), anhydrous diethyl ether (10 mL), and a freshly prepared solution of sodium methoxide in methanol (85 mg Na metal in 5 mL methanol; 3.68 mmol), to yield intermediate B5 as a yellow solid (301 mg, 54%). m.p. 275–279° C. HRMS Cal'd for C$_{19}$H$_{13}$NO$_3$ 303.0895. Found 303.0899.

Intermediate B9: Methyl 5-(2-phenethyl)-3-indoleglyoxylate

Intermediate B9 was prepared according to the method described for Intermediate B 1, intermediate A9 (300 mg, 1.40 mmol), oxalyl chloride (147 µL; 1.68 mmol), anhydrous diethyl ether (10 mL), and a freshly prepared solution of sodium methoxide in methanol (64 mg Na metal in 5 mL methanol, 2.80 mmol), to yield intermediate B5 as a yellow solid (327 mg, 76%). m.p. 204–207° C. HRMS Cal'd for C$_{19}$H$_{17}$NO$_3$ 307.1208. Found 307.1206.

Intermediate B10: Methyl 1-(2-hydroxyethyl)-5-benzyloxy-3-indoleglyoxylate

Intermediate A11 (5.64 g, 18.37 mmol) was dissolved in dry ether (250 mL). Oxalyl chloride (1.77 mL) was added via syringe and the reaction allowed to stir for 3 hours. In a seperate flask Na metal (1.39 g, 55.11 mmol) is dissolved slowly into omnisolv methanol (50 mL). After 3 hours the sodium methoxide solution is slowly added to the original reaction at 0° C. The reaction is then allowed to stir over night at room temperature. After 24 hours water (50 mL) is added to quench the reaction. A large amount of solid precipitates out. The solid is filtered off and washed with water (20 mL) and methanol (3×20 mL). This afforded intermediate B11 as a yellow solid (3.35 g, 52%). m.p. 148.2–149.5° C. $^1$H NMR (200 MHz, DMSO-d$^6$) δ 10.52 (br s, 1H), 7.98 (s, 1H), 7.43 (m, 6H), 7.11 (d, 9.0 Hz, 2H), 6.96, (m, 2H), 6.72 (m, 2H), 5.30 (dd, 5.2 Hz, 4.5 Hz, 1H), 5.10 (d, 3.7 Hz, 2H), 4.91, (t, 5.2 Hz, 1H), 4.26 (m, 2H), 3.69 (m, 2H).

Intermediate B11: Methyl 1-(2-hydroxyethyl)-3-indoleglyoxylate

Oxalyl chloride (663 µl; 7.6 mmol) was added dropwise to an icecold solution of intermediate A11 (780 mg; 3.8 mmol) in diethyl ether (5 mL). The solution was allowed to warm to room temperature and stirred for 2 hours. The reaction was cooled on ice and a freshly prepared solution of sodium methoxide in methanol (262 mg Na metal in 8 mL methanol) added. The reaction was allowed to warm to room temperature and stirred for 3 hours. The reaction was quenched by the addition of water (10 mL) and the resulting pale brown solid isolated by filtration, washed with water, diethyl ether and dried in vacuo to furnish intermediate B8 (550 mg, 59%). m.p. 131–132° C. $^1$H NMR (500 MHz, DMSO-d$^6$) δ 3.76 (2H, dt, J 5.3, 5.3), 3.89 (3H, s), 4.36 (2H, t, J 5.3), 4.98 (1H, t, J 5.3), 7.30 (1H, ddd, J 7.1, 7.1, 1.0), 7.33 (1H, ddd, J 7.2, 7.2, 1.4), 7.66 (1H, d, J 7.6), 8.18 (1H, d, J 7.7), 8.46 (1H, s).

Intermediate C1: 2-(N-indolyl) acetamide

A solution of indole (10 g; 0.085 mol) in DMF (50 mL) was added dropwise to an ice cooled suspension of NaH (supplied as 60% dispersion in mineral oil) (4.1 g; 0.10 mol) in DMF (100 mL). The reaction was allowed to warm to room temperature and stirred for 4 hours until all NaH was consumed. A solution of iodoacetamide (18.5 g; 0.1 mol) in DMF (50 mL) was added and the reaction left to stir at room temperature overnight. The DMF was removed in vacuo and the residue dissolved in ethyl acetate (1 L). The organic solution was washed with water until the washings were clear (3×500 mL), brine (500 mL), dried over anhydrous magnesium sulfate and the solvent removed in vacuo. Recrystallisation from ethyl acetate provided intermediate C1 as an off white solid (9.20 g, 62%). m.p. 177–179° C. $^1$H NMR (500 MHz, DMSO-d$^6$) δ 4.79 (2H, s), 6.44 (1H, dd, J 3.1, 0.7), 7.03 (1H, ddd, J 7.8, 7.8, 0.9), 7.13 (1H, ddd, J 8.2, 8.2, 1.0), 7.24 (1H, br), 7.31 (1H, d, J 3.1), 7.35 (1H, dd, J 8.2, 0.6), 7.50 (1H, br), 7.55 (1H, d, J 7.8).

Intermediate C2: 1H-5-methoxyindol-3-yl acetamide 5-methoxyindole (2.00 g, 13.6 mmol) was dissolved in DMF (75 mL). Sodium hydride (652 mg, 16.31 mmol) was added quickly and the reaction was stirred for 4 hours. Iodoacetamide (2.51 g, 13.6 mmol) was then added and the reaction allowed to stir over night at room temperature. The DMF is then removed on the rotary evaporator and the resulting solid worked up in ethyl acetate and water. The recovered solid is then purified through 2 recrystallizations in ethyl acatete. This yields the white solid intermediate C2 (1.95 g, 71%). m.p. 201.1–202.8° C. $^1$H NMR (200 MHz, DMSOA-d$^6$) δ 7.55(br s, 1H), 7.12 (m, 3H), 7.04 (s, 1H), 6.75 (d, 7.25 Hz, 1H), 6.33, (d, 3.4 Hz, 1H), 6.74(s, 2H), 6.73(s, 3H).

Intermediate C3: 1H-5-benzyloxyindol-3-yl acetamide

A solution of 5-benzyloxyindole (2.0 g; 8.6 mmol) in DMF (20 mL) was added dropwise to an ice cooled suspension of NaH (60% dispersion in mineral oil) (413 mg; 10.32 mmol) in DMF (30 mL). The reaction was allowed to warm to room temperature and stirred for 3 hours until all NaH was consumed. A solution of iodoacetamide (1.9 g; 10.32 mmol) in DMF (20 mL) was added and the reaction left to stir at room temperature for 3 hours. The DMF was removed in vacuo and the residue dissolved in ethyl acetate (200 mL). The organic solution was washed with water until the washings were clear, brine, dried over anhydrous magnesium sulfate and the solvent removed in vacuo. Recrystallisation from ethyl acetate firnished Intermediate C3 as an off white solid (2.2 g, 87%).

m.p. 204.0–205.0° C. $^1$H NMR (500 MHz, DMSO-d$^6$) δ 4.72 (s, 2H), 5.09 (s, 2H), 6.32 (1H, d, J 3.0), 6.85 (1H, dd, J 8.8, 2.4), 7.12 (1H, d, J 2.4), 7.19 (1H, br), 7.24 (2H, m), 7.30 (1H, dd, J 7.3, 7.3), 7.3 (2H, dd, J 7.4, 7.4), 7.44 (1H, br), 7.45 (2H, d, J 7.3).

Intermediate C12: 2-(6-methoxyindol-1-yl) acetamide

Intermediate C12 was prepared as described for Intermediate C2 using 6-methoxyindole (489 mg, 3.32 mmol), sodium hydride (160 mg, 3.98 mmol) and iodoacetamide (615 mg, 3.32 mmol) in DMF (50 mL). Two recrystallizations from ethyl acatete yielded intermediate C12 as a whte solid (252 mg, 37%). m.p. 210.1–211.0° C. $^1$H NMR (200 MHz, DMSO-D$^6$) δ 7.48 (br s, 1H), 7.41 (d, 8.6 Hz, 1H), 7.25 (br s, 1H), 7.16 (d, 3.2 Hz, 1H), 6.91 (d, 2.0 Hz, 1H), 6.69 (dd, 6.4 Hz, 2.2 Hz, 1H), 6.35 (d, 0.8 Hz, 1H), 4.74 (s, 2H), 3.77 (s, 3H).

Intermediate C13: 7-aza-indol-3-yl acetamide

Intermediate C13 was prepared as described for intermediate C2 using 7-aza-indole (1.00 g, 8.46 mmol), sodium hydride (406 mg, 10.15 mmol) and iodoacetamide (1.57g, 8.46 mmol) in DMF (100 mL). Two recrystallizations from ethyl acatete yielded Intermediate C5 as a whte solid (920 mg, 62%).

m.p. 180.0–181.0° C. $^1$H NMR (200 MHz, DMSO-d) δ 8.21 (dd, 3.1 Hz, 1.5 Hz, 1H), 7.95 (dd, 6.3 Hz, 1.6 Hz, 1H), 7.60 (br s, 1H), 7.48 (d, 3.5 Hz, 1H), 7.19 (br s, 1H), 7.08 (m, 2H), 6.46 (d, 3.5 Hz, 1H), 4.88 (s, 3H). MS (EI, m/z) M$^+$=175.

Intermediate D2:

To a solution of 5-methoxyindole (2.50 g, 17.0 mmol) in 50 mL of anhydrous diethyl ether cooled to 0° C. was added oxalyl chloride (1.63 mL, 18.68 mmol) and subsequently warmed to room temperatue. After 3.5 hours the solution was cooled to 0° C. and 50 mL of an aqueous solution of ammonium carbonate was added. After stirring overnight the precipitate was filtered off and washed with water, isopropanol and diethyl ether to afford the desired acetamide in 78% yield as a bright yellow solid.

m.p. 251.6–252.7° C. $^1$H-NMR (200 MHz, DMSO-d$^6$) δ 11.3 (broad s, 1H), 8.6 (s, 1H), 8.0 (s, 1H), 7.73 (d, 1H, J=2.57 Hz), 7.68 (s, 1H), 7.4 (d, 1H, J=8.81 Hz), 6.8 (dd, 1H, J=2.56; 8.79 Hz), 3.8 (s, 3H).

Intermediate F1: N-(indolyl)acetic acid

Indole (1.17 g, 10.0 mmol) and n-Bu$_4$NHSO$_3$ (339 mg, 1.0 mmol) were dissolved in benzene (30 mL) and stirred rapidly with 50% aqueous NaOH (10 mL). After 5 minutes ethyl bromoacetate (1.66 mL, 15 mmol) was added and the reaction was stirred for an additional hour. The aqueous layer was separated and washed with diethyl ether, acidified and extracted with methylene chloride under standard workup conditions to yield intermediate F1 as an off white solid in 72% yield. m.p. 175–178° C. $^1$H NMR(500 MHz, DMSO-d$^6$) δ 5.03 (2H, s), 6.47 (1H, d, J 3.1), 7.05 (1H, dd, J 7.8, 7.8), 7.13 (1H, dd, J 8.2, 8.2), 7.35 (1H, d, J 3.1), 7.39 (1H, d, J 8.2), 7.57 (1H, d, J 7.8), 13.01 (1H, br).

Intermediate F2: N-(5-benzyloxyindole) acetic acid

5-Benzyloxyindole (10.00 g, 44.8 mmol) and n-Bu$_4$NHSO$_4$ (1.00 g) were partitioned between toluene (500 mL) and 50% aqueous NaOH (200 mL). This solution was stirred vigorously for 30 minutes before neat ethyl bromoacetate (5.0 mL, 44.8 mmol) was added. After stirring for an additional 2 h the mixture was diluted with diethyl ether and water. The aqueous layer was washed with diethyl ether before being acidified with 6N HCl. The resulting solid was filtered off, washed with water, and dried in vacuo to privide of N-(5-benzyloxyindole)acetic acid as an off white solid (12.21 g, 98%).

Intermediate G1:

Crude intermediate H1 (1.00 g, 6.21 mmol) was dissolved in THF (100 mL) and added dropwise to a cold THF (500 mL) suspension of LiAlH$_4$ (2.70 g, 6.83 mmol). After stirring at room temperature for 1 hour 2M HCl was added, followed by diethyl ether. The organic layer was subjected to standard aqueous workup to provide intermediate G as a clear oil (0.94 g, 94%). $^1$H NMR (500 MHz, CDCl$_3$) δ 1.91 (1H, br), 3.79 (2H, t, J 5.3), 4.16 (2H, t, J 5.3), 6.51 (1H, dd, J 3.1, 0.6), 7.10 (1H, d, J 3.1), 7.14 (1H, ddd, J 7.0, 7.0, 1.0), 7.23 (1H, ddd, J 7.0, 7.0, 1.1), 7.34 (1H, dd, J 8.3, 0.6), 7.61 (1H, ddd, J 7.9, 1.0, 1.0).

Intermediate G2:

Crude N-(5-benzyloxyindole)acetic acid (12.21 g, 44.2 mmol) was dissolved in THF (100 mL) and added dropwise to a cold THF (500 mL) suspension of LiAlH$_4$ (1.78 g, 44.2 mmol). After stirring at room temperature for 1 hour 2M HCl was added, followed by diethyl ether. The organic layer was subjected to standard aqueous workup to provide N-(2-hydroxyethyl)-5-benzyloxindole as a clear oil (11.09 g, 94%). $^1$H NMR (500 MHz, CDCl$_3$) δ 7.51 (d, J=11.8 Hz, 1H), 7.50 (d, J=7.4 Hz, 2H), 7.41 (t, J=7.4 Hz, 2H), 7.34 (t, J=7.4 Hz, 1H), 7.22 (d, J=8.9 Hz, 1H), 7.19 (s, 1H), 6.99 (d, J=8.9 Hz, 1H), 6.42 (d, J=2.5 Hz, 1H), 5.11 (s, 2H), 4.10 (m, 2H), 3.75 (m, 2H), 2.01 (br s, 1H). MS (EI, m/z) M$^+$=267.

Intermediate H1:

Acetic anhydride (492 µl, 5.2 mmol) was added to a solution of intermediate G1(700 mg; 4.34 mmol) in THF (10 mL) followed by a catalytic amount of DMAP and the reaction left to stir at room temperature for 10 minutes. The reaction was diluted with ethyl acetate (50 mL), the organic solution washed with a saturated solution of sodium bicarbonate (20 mL), water (20 mL), rinsed with brine (20 mL), dried over anhydrous magnesium sulfate and concentrated in vacuo to yield intermediate H1 as a yellow oil (820 mg; 93%) which was used without further purification. $^1$H NMR (500 MHz, CDCl$_3$) δ 7.64 (dd, J=0.9, 8.0 Hz, 1H), 7.36 (dd, J=8.0 Hz, 1H), 7.23 (dt, J=0.9, 8.0 Hz, 1H), 7.12 (dt, J=0.9, 8.0 Hz, 1H), 7.11 (d, J=3.2 Hz, 1H), 6.52 (d, H=3.2 Hz, 1H), 4.37 (m, 4H), 2.00 (s, 3H).

Intermediate H2:

Crude N-(2-hydroxyethyl)-5-benzyloxyindole (11.09 g, 42.1 mmol), acetic anhydride (4.36 mL, 46.3 mmol), triethylamine (6.50 mL,46.3 mmol), and DMAP (100 mg) were stirred together in THF for 1 hour before standard aqueous workup provided N-2-acetoxyethyl)-5-benzyloxyindole as a clear oil (13.0 g, 99%). $^1$H NMR (500 MHz, CDCl$_3$) δ 7.51 (d, J=8.1 Hz, 2H), 7.42 (t, J=8.1 Hz, 2H), 7.35 (s, 1H), 7.27 (d, J=8.9 Hz, 1H), 7.21 (d, J=2.4 Hz, 1H), 7.09 (d, J=3.1 Hz, 1H), 7.01 (dd, J=2.4, 8.1 Hz, 1H), 6.47 (dd, J=0.8, 3.1 Hz, 1H),5.14(s,2H), 4.37 (t, J=5.0 Hz 2H), 4.31(t, J=5.0 Hz, 2H), 2.02 (s, 3H).

EXEMPLARY PREPARATIVE METHODS FOR FORMULA I TO III

The following examples provide synthetic methods for preparation of compounds according to the invention. Generally, the example number corresponds to the compound numbers shown in Tables 2 to 5.

EXAMPLE 1

3-(indol-1-yl)-4-(1H-indol-3-yl)-1H-pyrrole-2,5-dione

A 1.0M solution of KO$^t$Bu (13.44 mL, 13.44 mmol) was added to a slurry intermediate B1 (1.82 g, 8.96 mmol) and intermediate C1 (780 mg; 4.48 mmol) in THF (10 mL). The reaction slowly turned red as the reactants started to go into solution. The reaction was stirred for 3 hours at room temperature after which time the reaction was quenched by the addition of concentrated HCl (8 mL) and diluted with ethyl acetate (100 mL). The organic solution was washed with water (100 mL), brine (100 mL), dried over anhydrous magnesium sulfate and concentrated in vacuo. The crude solid was purified by silica gel chromatography, eluting with 1:1 hexanes/ethyl acetate, to provide Compound 1 as a red solid (983 mg, 67%). m.p. 212–213° C. $^1$H NMR (500 MHz, DMSO-d) δ 6.08 (1H, d, J 8.1), 6.49 (1H, ddd, J 8.1, 8.1,0.9), 6.75 (1H, dd, J 3.4, 0.7), 6.86 (1H, ddd, J 8.1, 8.1, 1.0), 6.93 (1H, ddd, J 8.1, 8.1, 1.0), 6.98 (2H, m), 7.33 (1H, d, J 8.1), 7.55 (1H, d, J 3.4), 7.56 (1H, d, J 8.8), 8.04 (1H, d, J 2.9), 11.23 (1H, s), 11.93 (1H, br s).

EXAMPLE 2

3-(5-Methoxyindol-3-yl)-4-(indol-1-yl)-1H-pyrrole-2,5-dione

Indole was dissolved in THF (25 mL) and treated with a 1.0M THF solution of KO$^t$Bu. This solution was stirred for 1 hour before ethyl bromoacetate was added. After stirring hour 3 hours intermediate D2 was added, followed by a 1.0M THF solution of KOtBU. This mixture was stirred over night before being quenced with conc HCl (3 mL) followed by standard aqueous workup. Purification by silica gel chromatography, eluting with 3:1 hexane/ethyl acetate, provided compound 2 as an orange solid (32%). $^1$H NMR (500 MHz, DMSO-d$^6$) δ 11.83 (s, 1H), 11.18 (s, 1H), 8.05 (d, J=3.0 Hz, 1H), 7.55 (d, J=7.8 Hz, 1H), 7.50 (d, J=3.3 Hz, 1H), 7.19 (d, J=8.7 Hz, 1H), 7.07 (d, J=8.2 Hz, 1H), 7.01 (t, J=7.2 Hz, 1H), 6.93 (t, J=7.2 Hz, 1H), 6.69 (d, J=3.3 Hz, 1H), 6.50 (dd, J=2.4, 8.7 Hz, 1H), 5.49 (d, J=2.3 Hz, 1H), 2.93 (s, 3H).

EXAMPLE 3

3-(5-Methoxyindol-1-yl)-4-(1H-indol-3-yl)-1H-pyrrole-2,5-dione

Indole (2.21 g, 18.9 mmol) was dissolved in THF (5 mL) and treated with a 1.0M solution of KO$^t$Bu (18.9 mL, 18.9 mmol). After stirring for 2 hours neat ethyl bromoacetate (2.10 mL, 18.9 mmol) was added and the resulting slurry was stirred for an additional 3 hours. Solid intermediate D2 (2.06 g, 9.44 mmol) was added followed by a 1.0M solution of KO$^t$Bu (37.8 mL, 37.8 mmol). After stirring for 16 hours the reaction was quenched with 10 mL of conc HCl and subjected to standard aqueous workup. Purification by silica gel chromatography, eluting with 2.5:1 petroleum ether/ acetone provided compound 4 as an orange/brown solid in 33% yield. $^1$H NMR (200 MHz, CDCl$_3$) δ 8.83 (br s, 1H), 8.00 (br s, 1H), 7.88 (d, J=3.0 Hz, 1H), 7.39 (d, J=3.4 Hz, 1H), 7.22 (d, J=8.6 Hz, 1H), 7.01 (m, 2H), 6.79 (d, J=9.0 Hz, 1H), 6.65 (m, 2H), 6.49 (dd, J=2.5, 9.0 Hz, 1H), 6.25 (d, J=8.2 Hz, 1H), 3.74 (s, 3H).

EXAMPLE 4

3-(5-Methoxy-1H-indol-3-yl)-4-(5-methoxyindol-1-yl)-pyrrole-2,5-dione

5-Methoxyindole (1.00 g, 6.79 mmol) was dissolved in TBF (20 mL) and treated with a 1.0M solution of KO$^t$Bu (6.80 mL, 6.80 mmol). After stirring for 2 hours neat ethyl bromoacetate (753 μL, 6.80 mmol) was added and the resulting slurry was stirred for an additional 3 hours. Solid intermediate D2 (1.48 g, 6.79 mmol) was added followed by a 1.0M solution of KO$^t$Bu (33.80 mL, 33.80 mmol). After stirring for 3 days the reaction was quenched with 3 mL of conc HCl and subjected to standard aqueous workup. Purification by silica gel chromatography, eluting with 3:2 petroleum ether/acetone provided compound 4 as a deep red solid in 9% yield. $^1$H NMR (200 MHz, DMSO-d$^6$) δ 11.49 (br s, 1H), 10.43 (br s, 1H), 8.61 (d, J=3.0 Hz, 1H), 7.95 (d, J=3.3 Hz, 1H), 7.70 (dd, J=5.2, 9.7 Hz, 1H), 7.52 (d, J=2.3 Hz, 1H), 7.48 (d, J=9.0 Hz, 1H), 7.25 (dd, J=2.3, 9.0 Hz, 1H), 7.10 (d, J=0.7 Hz, 1H), 7.05 (m, 1H), 6.85 (d, J=0.7 Hz, 1H), 6.14 (d, J=2.3 Hz, 1H), 4.23 (s, 3H), 4.17 (s, 3H).
MS (EI, m/z) M$^+$=387.

EXAMPLE 5

3-(5-Benzyloxy-1H-indol-3-yl)-4-(indol-1-yl)-pyrrole-2,5-dione

KO$^t$Bu (1.0M solution in THF; 5.16 mL; 5.16 mmol) was added to a slurry of intermediate B3 (1.06 g; 3.44 mmol) and C1 (300 mg; 1.72 mmol) in THF (5 mL). The reaction slowly turned red as the reactants started to go into solution. The reaction was left for 3 hours at room temperature before being quenched by the addition of concentrated HCl (3 mL) and diluted with ethyl acetate (100 mL). The organic solution was washed with water (100 mL), brine (100 mL), dried over anhydrous magnesium sulfate and concentrated in vacuo. Purification by silica gel chromatography using 3:2 hexanes/ethyl acetate as mobile phase yielded Compound 5 as a red solid (689 mg; 92%). m.p. 217–220° C. $^1$H NMR (500 MHz, DMSO-d$^6$) δ 4.03 (2H, s), 5.57 (1H, d, J 2.3), 6.60 (1H, dd, J 8.7, 2.3), 6.74 (1H, dd, J 3.3, 0.7), 7.22 (1H, d, J 8.7), 7.49 (1H, d, J 3.3), 7.58 (1H, d, J 7.6), 8.09 (1H, s), 11.19 (1H, s), 11.87 (1H, s).

EXAMPLE 6

3-(1-(2-hydoxyethyl)-5-benzyloxyindol-3-yl)-4-(indol-1-yl)-1H-pyrrole-2,5-dione

Intermediate B7 (1.01 g, 0.287 mmol) and Intermediate C1 (0.25 g, 0.144 mmol) were suspended in dry THF (100 mL). A 1M solution of potassium tert-butoxide (4.31 mL) was added at 0° C. and allowed to stir at room temperature over the weekend. Solvent was removed in vacuo and the residue partitioned between ethyl acetate and 1M HCl. The organic layer was subjected to standard aqueous workup and further purified using silicon gel chromatography, eluting with pure ethyl acetate, to provide Compound 6 as an orange solid (150 mg, 22%). m.p. 205.0–207.0° C. $^1$H NMR (200 MHz, DMSO-d$^6$) δ 11.20, (br s, 1H), 8.20 (s, 1H), 7.58 (d, 7.7 Hz, 1H), 7.21, (m, 10H), 6.67 (m, 2H), 5.54, (d, 1.7 Hz, 1H), 5.11 (br s, 1H), 4.23, (m, 2H), 3.99, (s, 2H).

EXAMPLE 7

3-(1-(2-hydoxyethyl)-5-benzyloxyindol-3-yl)-4-(5-methoxyindol-1-yl)-1H-pyrrole-2,5-dione Intermediate B7 (0.5 g, 0.142 mmol) and Intermediate C2 (0.145 g, 0.071 mmol) were suspended in dry THF (100 mL). A 1M solution of potassium tert-butoxide (2.14 mL) was added at 0° C. and allowed to stir at room temperature over night. Solvent was removed in vacuo and the residue partitioned between ethyl acetate and 1M HCl. The organic layer was subjected to standard aqueous workup and further purified using silicon gel chromatography, eluting with pure ethyl acetate, to provide Compound 7 as an orange solid was recovered (221 mg, 62%). m.p. 200.0–201.0° C. $^1$H NMR (200 MHz, DMSO-D$^6$) δ 11.23 (br s, 1H), 8.19 (s, 1H), 7.25 (m, 9H), 6.65 (m, 3H), 5.59 (s, 1H), 5.02 (br s, 1H), 4.27 (br s, 2H), 3.97 (s, 2H), 3.75 (br s, 2H), 3.61 (s, 3H).

EXAMPLE 8 and 9

3-(1-(2-hydoxyethyl)-5-benzyloxyindol-3-yl)-4-(6-methoxyindol-1-yl)-1H-pyrrole-2,5-dione, 8, and 3-(5-benzyloxyindol-3-yl)-4-(6-methoxyindol-1-yl)-1H-pyrrole-2,5-dione, 9.

Intermediate B7 (0.5 g, 0.142 mmol) and Intermediate C3 (0.145 g, 0.071 mmol) was suspended in dry THF (100 mL). A 1M solution of potassium tert-butoxide (2.14 mL) was added at 0° C. and allowed to stir at room temperature over night. The solvent was removed in vacuo and the residue partitioned between ethyl acetate and 1M HCl. The organic layer was subjected to standard aqueous workup. Purification using silicon gel chromatography, eluting with 2:1 ethyl acetate/petroleum ether yielded Compound 8 as an orange solid (245 mg, 69%) along with Compound 9 as an orange solid (24 mg, 8%). Compound 8: $^1$H NMR (200 MHz, DMSO-d$^6$) δ 11.25 (br s, 1H), 8.17 (s, 1H), 7.30 (m, 8H), 6.65 (m, 4H), 5.63 (s, 1H), 5.00 (t, 5.0 Hz, 1H), 4.36 (br s, 2H), 4.12 (s, 2H), 3.78 (br s, 2H), 3.39 (s, 3H). Compound 9: $^1$H NMR (200 MHz, DMSO-d$^6$) δ 11.87 (br s, 1H), 11.21 (br s, 1H), 8.05 (d, 3.0 Hz, 1H), 7.31 (m, 8H), 6.63 (m, 4H), 5.65 (s, 1H), 4.15 (s, 1H).

EXAMPLE 10

3-(1-(2-hydoxyethyl)-indol-3-yl)-4-(indol-1-yl)-1H-pyrrole-2,5-dione

KO$^t$Bu (1.0 M solution in THF; 2.73 mL; 2.73 mmol) was added to a slurry of intermediate B11 (500 mg; 1.8 mmol) and intermediate C1 (160 mg; 0.91 mmol) in THF (2.5 mL). The reaction slowly turned red as the reactants started to go into solution. The reaction was left for 2 hours at room temperature after which time all C1 had been consumed. The reaction was quenched by the addition of concentrated HCl (1.5 mL) and diluted with ethyl acetate (30 mL). The organic solution was washed with water (10 mL), brine (10 mL), dried over anhydrous magnesium sulfate and concentrated in vacuo. Purification by silica gel chromatography using 1:1 hexanes: ethyl acetate as mobile phase yielded Compound 10 as a red solid (257 mg; 76%). m.p. 210–212° C. $^1$H NMR (500 MHz, DMSO-d$^6$) δ 3.73 (2H, dt, J 5.3, 5.3), 4.29 (2H, t, J 5.3), 4.94 (1H, t, J 5.3), 5.99 (1H, d, J 8.1), 6.48 (1H, dd, J 8.0, 8.0), 6.72 (1H, d, J 3.3), 6.88 (1H, dd, J 8.2, 8.2), 6.96 (2H, m), 6.99 (1H, d, J 7.3), 7.43 (1H, d, J 8.2), 7.49 (1H, d, J 3.3), 7.56 (1H, d, J 7.3), 8.14 (1H, s), 11.2 (1H, s).

EXAMPLE 11

3-(5-benzyloxyindol-1-yl)-4-(1H-5-benzyloxyindol-3-yl)-1H-pyrrole-2,5-dione

KO$^t$Bu (1.0M solution in THF; 1.71 mL; 1.71 mmol) was added to a slurry of intermediate B3 (353 mg, 1.14 mmol) and intermediate C3 (160 mg; 0.57 mmol) in THF (2 mL). The reaction slowly turned red as the reactants started to go into solution. After stirring for 3 h the reaction was quenched by addition of concentrated HCl (2 mL) and diluted with ethyl acetate (50 mL). The organic solution was washed with water (20 mL), brine (20 mL), dried over anhydrous magnesium sulfate and concentrated in vacuo. Tituration with acetone yielded compound 11 as a red solid in 68% yield.

EXAMPLE 12

3-(5-benzyloxyindol-1-yl)-4-(1H-indol-3-yl)-1H-pyrrole-2,5-dione

KO$^t$Bu (1.0M solution in THF; 3.21 mL; 3.21 mmol) was added to a slurry of intermediate B1 (435 mg; 2.14 mmol) and intermediate C3 (300 mg; 1.07 mmol) in THF (3 mL). The reaction slowly turned red as the reactants started to go into solution. The reaction was left for 3 hours at room temperature after which time all intermediate C3 had been consumed by TLC analysis. The reaction was quenched by the addition of concentrated HCl (2 mL) and diluted with ethyl acetate (50 mL). The organic solution was washed with water (20 mL), brine (20 mL), dried over anhydrous magnesium sulfate and concentrated in vacuo. Purification by silica gel chromatography using 1:1 hexanes/ethyl acetate as mobile phase yielded compound 12 as a red solid (322 mg, 70%). m.p. 114–116° C. $^1$H NMR (500 MHz, DMSO-d$^6$) δ 5.01 (2H, s), 6.12 (1H, d, J 8.1), 6.52 (1H, dd, J 7.6, 7.6), 6.5 (1H, dd, J 8.9, 2.1), 6.65 (1H, d, J 3.0), 6.84 (1H, d, J 8.9), 6.95 (1H, dd, J 7.6, 7.6), 7.14 (1H, d, J 2.0), 7.34 (6H, m), 7.50 (1H, d, J 3.2), 8.00 (1H, d, J 2.7), 11.18 (1H, s), 11.90 (1H, br).

EXAMPLE 13

3-(indol-1-yl)-4-(1H-5-bromoindol-3-yl)-1H-pyrrole-2,5-dione

This structure was prepared according to the procedure described for Example 12 using intermediate B4 and C1. $^1$H NMR (200 MHz, DMSO-d$^6$) δ 12.03 (br s, 1H), 11.27 (br s, 1H), 8.05 (s, 1H), 7.59 (d, J=4.5 Hz, 11), 7.56 (s, 1H), 7.27 (d, J=8.6 Hz, 1H), 7.05 (d, J=1.8 Hz, 1H), 6.97 (d, J=8.6 Hz, 1H), 6.86 (t, J=8.6 Hz, 2H), 6.79 (d, J=3.3 Hz, 1H), 6.02 (d, J=1.8 Hz, 1H).

EXAMPLE 14

3-(indol-1-yl)-4-(1H-5-iodoindol-3-yl)-1H-pyrrole-2,5-dione

KO$^t$Bu (1.0M solution in THF; 6.9 mL; 6.9 mmol) was added to a slurry of intermediate B5 (1.5 g; 4.6 mmol) and intermediate C1 (400 mg; 2.3 mmol) in THF (10 mL). The reaction slowly turned orange as the reactants started to go into solution. The reaction was left for 5 hours at room temperature after which time all 2-indol-1-yl-acetamide had been consumed. The reaction was quenched by the addition of concentrated HCl (4 mL) and diluted with ethyl acetate (100 mL). The organic solution was washed with water (100 mL), brine (100 mL), dried over anhydrous magnesium sulfate and concentrated in vacuo. Purification by silica gel chromatography using 1:1 hexanes/ethyl acetate as mobile phase yielded compound 14 as an orange solid (503 mg, 48%). m.p. 260–261° C. $^1$H NMR (500 MHz, DMSO-d) δ 6.18 (1H, s, ArH), 6.81 (1H, d, J 3.3, ArH), 6.85 91H, d, J, 7.3, ArH), 6.89 (1H, d, J 8.2, ArH), 7.56(11H, d, J 3.3, ArH), 7.60 (1H, d, J 7.9, ArH), 8.03 (1H, d, J 2.9, ArH), 11.25 (1H, s, maleamide NH), 12.04 (1H, br, indole NH).

EXAMPLE 15

3-(Indol-1-yl)-4-(5-(β-phenylethynyl)-indol-3-yl)-pyrrole-2,5dione

A 1.0M THF solution of KO$^t$Bu (1.23 mL, 1.23 mmol) was added to a slurry of intermediate B8 (250 mg, 0.82 mmol) and intermediate C1 (71.4 mg, 0.41 mmol) in THF (1.5 mL). The reaction slowly turned red as the reactants started to go into solution. The reaction was left for 4 hours at room temperature until no remaining C1 was observed by TLC. The reaction was quenched by the addition of concentrated HCl (750 µL) and diluted with ethyl acetate (30 mL). The organic solution was washed with water (20 mL), brine (20 mL), dried over anhydrous magnesium sulfate and concentrated in vacuo. Purification by silica gel chromatography, eluting with 1:1 hexanes/ethyl acetate, yielded compound 15 as a red solid (135 mg, 77%). m.p. 141–144° C. $^1$H NMR (500 MHz, DMSO-d6) δ 6.11 (1H, s), 6.79 (1H, d, J 3.2), 6.91 (1H, m), 7.01 (2H, dd, J 7.0, 7.0), 7.08 (1H, dd, J 8.3, 1.3), 7.39 (6H, m), 7.52 (1H, d, J 3.3), 7.58 (1H, d, J 7.8), 8.08 (1H, d, J 1.4), 11.25 (1H, s), 12.09 (1H, s).

EXAMPLE 16

3-(Indol-1-yl)-4-(5-(β-phenethyl)indol-3-yl)-pyrrole-2,5-dione

A 1.0M THF solution of KO$^t$Bu (1.50 mL, 1.50 mmol) was added to a slurry of B9 (307 mg, 1.00 mmol) and C1 (87.0 mg, 0.50 mmol) in THF (1.5 mL). The reaction slowly turned red as the reactants started to go into solution. The reaction was left for 16 hours at room temperature after until no remaining C1 was observed by TLC. The reaction was quenched by the addition of concentrated HCl (1 mL) and diluted with ethyl acetate (20 mL). The organic solution was washed with water (15 mL), brine (15 mL), dried over anhydrous magnesium sulfate and concentrated in vacuo. Purification by silica gel chromatography using 1:1 hexanes: ethyl acetate as mobile phase yielded compound 16 as a red solid (205 mg, 95%). m.p. 210–211° C. $^1$H NMR (500 MHz, DMSO-d) δ 2.20 (2H, AB splitting), 2.28 (2H, AB splitting), 5.68 (1H, s), 6.73 (1H, d, J 8.2), 6.77 (1H, d, J 2.8), 6.91 (1H, dd, J 7.6, 7.6), 7.00 (4H, m), 7.14 (1H, dd, J 7.3, 7.3), 7.18 (1H, d, J 8.2), 7.24 (2H, dd, J 7.3, 7.3), 7.53 (1H, d, J 3.2), 7.56 (11H, d, J 7.8), 8.13 (1H, d, J 2.8), 11.19 (11H, s), 11.87 (1H, br).

EXAMPLE 17

2-(N-benzimidazolyl)-3-(indol-3-yl)-pyrrole-2,5-dione

Benzimidazole (2.56 g, 21.74 mmol) and 3bromo acetamide (1.5 g, 10.87 mmol) were added to dry THF (50 mL). The solution was stirred under nitrogen over night. The THF is removed in vacuo and the resulting solid is partitioned between ethyl acetate and water. The organic layer, after removal of the solvent in vacuo yielded 2-N-benzimidazolyl)acetamide, intermediate K1, as a white solid. Crude intermediate K1 from above and intermediate B1(2.20 g, 10.9 mmol) were suspended in THF (100 mL) and treated with a 1.0M solution of potassium tert-butoxide (43.5 mL, 43.5 mmol) at 0° C. and stirred for 3 days. Standard workup using ethyl acetate and aqueous 2M HCl yielded an orange residue, which was further purified by acetone titration to afford compound 17 as an orange solid (650 mg, 18%). m.p. 246.4–249.0° C. $^1$H NMR (200 MHz, DMSO-d$^6$) δ 12.09 (br s, 1H), 11.41 (br s, 1H), 8.43 (s, 1H), 8.11 (d, J=2.3 Hz, 1H), 7.70 (d, 7.9 Hz, 1H), 7.37 (d, J=8.2 Hz, 1H), 7.08 (m, 4H), 6.53 (t, J=7.6 Hz, 1H), 6.08 (d, J=8.1 Hz, 1H).

EXAMPLE 18

Compound 17 (328 mg, 1.0 mmol) was added too a DMF (5 mL) solution of 60% w/w parifin/NaH (120 mg, 3 mmol). After stirring for 2 hours Boc$_2$0 (273 mg, 1.25 mmol) was added and the mixture as stirred for 16 hours. Standard aqueous/ethyl acetate workup, followed by silica gel chromatography, eluting with 1:1 petroleum ether/ehtyl acetate, yieled compound 18 was a yellow solid (165 mg, 39%).

EXAMPLE 19

Compound 17 (296 mg, 0.903 mmol), DMAP (5 mg), triethylamine (138 µL, 0.990 mmol), and acetyl chloride (64 µL, 0.900 mmol) were stirred together in DMF (5 mL) for 16 hours. Standard aqueous/ethyl acetate workup and purification by silica gel chromatography, eluting with 2:1 petroleum ether/acetone, provided compound 19 as a red solid. $^1$H NMR (200 MHz, DMSO-d$^6$) δ 11.40 (br s, 1H), 8.45 (s, 1H), 8.14 (s, 1H), 8.08 (d, J=7.8 Hz, 1H), 7.68 (d, J=8.0 Hz, 1H), 7.20–6.98 (m, 4H), 6.78 (t, J=7.8 Hz, 1H), 6.30 (d, J=7.8 Hz, 1H), 2.68 (s, 3H).

EXAMPLE 20

Compound 17, triethylamine, and phenylisocyanate were refluxed in THF for 24 hours. The solvent was removed in vacuo and the resulting solid purified by silica gel chromatography, eluting with 2:1 hexane/acetone, to provide compound 20 as a yellow solid in 78% yield. $^1$H NMR (200 MHz, DMSO-d$^6$) δ 11.66 (br s, 1H), 10.56 (s, 1H), 8.66 (s, 1H), 8.46 (s, 1H), 8.12 (d, J=8.3 Hz, 1H), 7.68 (d, J=7.8 Hz, 3H), 7.41 (t, J=8.0 Hz, 1H), 7.23–6.99 (m, 5H), 6.71 (t, J=7.1 Hz, 1H), 6.29 (d, J=8.1 Hz, 1H).

EXAMPLE 21

3-(N-benzimidazolyl)-4(5-benzyloxyindol-3-yl)-pyrrole-2,5-dione

Intermediate B3 (1.18 g, 4 mmol), intermediate K1 (700 mg, 4 mmol), K$_2$CO$_3$ (4.42 g, 32 mmol), and CETAB (102 mg, 0.28 mmol) are suspended in dry benzene (150 mL). This mixture was refluxed for 4 days, removing water using a Dean Stark apparatus. The solvent was removed in vacuo and the resulting solid was partitioned between ethyl acetate and 2M aqueous HCl. The organic layer was washed with water, dried over anhydrous MgSO$_4$, filtered and dried down under reduced pressure. The resulting red solid was further purified by two silica gel chromatography columns, the first eluting with 2.5:1 petroleum ether/acetone, and the second eluting with 1:1 petroleum ether/acetone, to provide compound 21 as an orange solid (90 mg, 5%). $^1$H NMR (500 MHz, DMSO-d$^6$) δ 12.05 (br s, 1H), 8.34 (s, 1H), 8.19 (s, 1H), 7.74 (d, J=8.0 Hz, 1H), 7.26 (m, 9H), 6.65 (dd, J=8.8 Hz, 1H), 5.53 (d, J=2.2 Hz, 1H), 3.97 (s, 2H), 3.08 (s, 3H).

EXAMPLE 22

Intermediate B1 (0.25 g, 1.43 mmol) and Intermediate C13 (0.58 g, 2.86 mmol) were suspended in dry THF (100 mL). A 1M solution of potassium tert-butoxide (4.30 mL) was added at 0° C. and allowed to stir at room temperature over night. Solvent was removed in vacuo and the residue partitioned between ethyl acetate and 1M HCl. The organic layer was subjected to standard aqueous workup and further purified using silicon gel chromatography, eluting with 1:1 ethyl acetate/petroleum ether, to provide Compound 21 as an orange solid was recovered (59 mg, 12%). $^1$H NMR (200MHz, DMSO-d$^6$) δ 11.99 (br s, 1H), 11.28 (br s, 1H), 8.14 (d, J=2.8 Hz, 1H), 8.01 (m, 2H), 7.65 (d, J=3.6 Hz, 1H), 7.33 (d, J=8.1 Hz, 1H), 7.04 (m, 2H), 6.76 (d, J=2.9 Hz, 1H), 6.77 (m, 1H), 5.92 (d, J=8.1 Hz, 1H).

EXAMPLE 23

Compound 22 (79 mg, 0.238 mmol), DMAP (29 mg, 0.238 mmol) and Boc$_2$O (55 μL, 0.238 mmol) were stirred together in THF (25 mL) for 16 hours. Standard aqueous/ethyl acetate workup and purification by preparative TLC, eluting with 3:1 petroleum ether/ethyl acetate, provided compound 23 as a red solid (35 mg, 34%).

EXAMPLE 24

Compound 1 (1.6 g; 4.89 mmol) was partially solubilised in dichloromethane (150 mL). TMSOTf (1.08 mL, 5.87 mmol) was added and the reaction left to stir at room temperature for 2 hours. The reaction was split into 3×50 mL portions and each portion treated as follows. The reaction was diluted with ethyl acetate (500 mL), washed with a saturated solution of sodium bicarbonate (250 mL), water (250 mL), brine (250 mL), dried over anhydrous magnesium sulfate and concentrated in vacuo. Purification by silica gel chromatography, eluting with 1:1 hexanes/ethyl, provided compound 23 as a dark purple solid (1.41 g, 88%). m.p. >300° C. $^1$H NMR (500 MHz, DMSO-d$^6$) δ 3.64 (1H, dd, J 9.9, 16.5), 3.91 (1H, dd, J 2.5, 16.5), 5.10 (1H, dd, J 2.5, 9.9), 7.16 (3H, m), 6.98 (1H, dd, J 7.6, 7.6), 6.78 (2H, m), 7.26 (1H, d, J 7.4), 7.44 (1H, d, J 7.6), 7.98 (1H, d, J 2.7), 10.57 (1H, s), 11.81 (1H, br).

EXAMPLE 25 and 26

Compound 24 (500 mg, 1.50 mmol) was suspended in ethanol (50 mL) and treated with 4 portions of NaBH$_4$ (170 mg, 4.5 mmol) over 4 hours. The reaction was quenched with water and diluted with ethyl acetate. The organic layer was washed with aqueous NH$_4$Cl followed by saturated aqueous NaHCO$_3$, and water, dried over anhydrous MgSO$_4$, filtered and volatiles removed under reduced pressure, providing a 1:1 mix of regeoisomers, compounds 25 and 26 in 89% combined yield.

EXAMPLE 27

Compound 32 was placed in a quartz tube, dissolved in acetonitrile, and placed in front of a 150 W light bulb for 16 hrs. Removal of the solvent under reduced pressure provided compound 27 as an off white solid. $^1$H NMR (200 MHz, DMSO-d$^6$) δ 11.30 (s, 1H), 7.90 (d, J=2.4 Hz, 1H), 7.80 (s, 1H), 7.37 (d, J=7.8 Hz, 1H), 7.28 (d, J=7.1 Hz, 1H), 7.17–6.99 (m, 4H), 6.84 (t, J=7.1 Hz, 1H), 5.29 (dd, J=8.0, 9.4 Hz, 1H), 4.96 (dd, J=8.0, 8.9 Hz, 1H), 3.88 (d, J=17.8 Hz, 2H), 3.77 (m, 1H).

EXAMPLE 29

Compound 24 (1.00 g, 3.05 mmol) was dissolved in THF (50 mL) and treated with Boc$_2$O (772 μL, 3.36 mmol) and DMAP (5 mg). The solution was stirred for 10 minutes before standard aqueous/ethyl acetate workup and purification by silica gel chromatography, eluting with 3:1 hexane/ethyl acetate, provided compound 29 as a red solid (530 mg, 41%).

EXAMPLE 30 and 31

Compound 29 (3.45 mg, 8.09 mmol) was dissolved in EtOH (150 mL) and treated with NaBH$_4$ (1.80 g, 48.5 mmol). After stirring for 3 hours the reation mixture was quenched with water and diluted with ethyl acetate. The organic layer was washed with aqueous NH$_4$Cl and worked up as usual provided a 3:1 mixture of regeoisomers. Purification by silica gel chromatography, eluting with 3:1 hexane/ethyl acetate, provided compound 30 (1.09 g, 31%, as a light brown solid, and compound 31 (340 mg, 10%) as an off white solid.

Compound 30: $^1$H NMR (200 MHz, DMSO-d$^6$) δ 8.25 (s, 1H), 8.20 (s, 1H), 8.04 (d, J=7.2 Hz, 1H), 7.41–7.20 (m, 4H), 7.06 (t, J=7.2 Hz, 1H), 6.84 (t, J-7.4 Hz, 1H), 6.30 (d, J=12.0 Hz, 1H), 6.14 (d, J=9.9 Hz, 1H), 5.29 (dd, J=5.4, 10.5 Hz, 1H), 3.91 (dd, J=5.4, 16.6 Hz, 1H), 3.67 (dd, J=10.5, 16.6 Hz, 1H), 1.63 (s, 9H).

Compound 31: $^1$H NMR (200 MHz, DMSO-d$^6$) δ 8.14 (d, J=3.1 Hz, 1H), 8.01 (d, J=7.0 Hz, 1H), 7.2 Hz, 1H), (d, J=8.4 Hz, 1H), 7.33 (m, 3H), 7.13 (t, J=7.6 Hz, 1H), 6.95 (t, J=7.3 Hz, 1H), 6.77 (d, J=9.9 Hz, 1H), 5.51 (d, J=9.9 Hz, 1H), 5.37 (dd, J=6.8, 9.9 Hz, 1H), 3.93 (dd, J=6.8, 18.5 Hz, 1H), 3.62 (dd, J=9.9, 18.5 Hz, 1H), 1.64 (s, 9H).

EXAMPLE 32

Major Isomer

Compound 30 (50 mg, 0.12 mmol) and p-toluenesulfonic acid (5 mg) were dissolved in methylene chloride (4 mL) and treated with phenyl selenol (89 μL, 0.84 mmol). The solution was stirred for 1 hour before the volatiles were removed under reduced pressure and the resulting solid was purified by silica gel chromatography, eluting with 19:1 methylene chloride/methanol, to provide compound 32 as a light brown solid (39 mg, 80%). $^1$H NMR (200 MHz, DMSO-d$^6$) δ 8.21 (s, 1H), 8.04 (d, J=7.7 Hz, 1H), 7.94 (s, 1H), 7.41–7.21 (m, 4H), 7.12 (t, J=7.9 Hz, 1H), 6.92 (t, J=7.2 Hz, 1H), 5.40 (dd, J=7.2, 10.2 Hz, 1H), 4.92 (d, J=18.2 Hz, 1H), 3.98 (d, J=18.2 Hz, 1H), 3.86–3.70 (m, 2H), 1.64 (s, 9H). MS (FAB, m/z) M$^+$1=414.

EXAMPLE 33

Minor Isomer

Compound 31 (100 mg, 0.24 mmol) and p-toluenesulfonic acid (5 mg) were dissolved in methylene chloride (5 mL) and treated with phenyl selenol (74 pL, 0.69 mmol). The solution was stirred for 1 hour before the volatiles were removed under reduced pressure and the resulting solid was purified by silica gel chromatography, eluting with 19:1 methylene chloride/methanol, to provide compound 32 as a light brown solid (75 mg, 79%).

EXAMPLE 34

Compound 3 was partially solubilized in dichloromethane and treated with neat TMSOTf. The mixture was stirred for 16 hours. The solvent was removed in vacuo and the resulting residue dissolved in ethyl acetate (10 mL). The organic solution was washed with saturated sodium bicarbonate solution (10 mL), water (10 mL), brine (10 mL), dried over anhydrous magnesium sulfate and concentrated in vacuo. Purification by silica gel chromatography, eluting with 1:1 hexanes/ethyl acetate, provided compound 34 as a dark purple solid. m.p. 248.4–250.5° C. $^1$H NMR (200 MHz, DMSO-d$^6$) δ 11.70 (s, 1H), 10.53 (s, 1H), 7.94 (d, J=2.6 Hz, 1H), 7.43 (d, J=7.1 Hz, 6.90 (d, J=1.8 Hz, 1H), 6.76 (d, J=8.6 Hz, 1H), 6.59 (dd, J=2.4, 8.6 Hz, 1H), 5.00 (d, J=7.5 Hz, 1H), 3.89 (d, J=7.5 Hz, 1H), 3.69 (s, 3H), 3.66 (m, 1H). MS (EI, m/z) M$^+$=357.

EXAMPLE 35

Compound 5 (20 mg; 0.046 mmol) was partially solubilized in dichloromethane (2 mL). Neat boron trifluoride diethyl etherate (11 μL; 0.055 mmol) added and the reaction left to stir at room temperature for 5 hours. The solvent was removed in vacuo and the resulting residue dissolved in ethyl acetate (10 mL). The organic solution was washed with saturated sodium bicarbonate solution (10 mL), water (10 mL), brine (10 mL), dried over anhydrous magnesium sulfate and concentrated in vacuo. Purification by silica gel chromatography, eluting with 1:1 hexanes/ethyl acetate, provided compound 35 as a dark purple solid (13 mg; 65%). mp 258.0–261.0° C. $^1$H NMR (500 MHz, DMSO-d$^6$) δ 11.69 (br s, 1H), 10.49 (br s, 1H), 7.92 (s, 1H), 7.31 (m, 6H), 7.07 (d, J=8.8 Hz, 1H), 6.86 (d, J=8.1 Hz, 1H), 6.32 (s, 1H), 6.29 (d, J=5.7 Hz, 1H), 5.31 (t, J=4.9 Hz, 1H), 5.08 (d, J=11.6 Hz, 1H), 5.06 (d, J=11.6 Hz, 1H), 5.15 (m, 1H), 3.65 (m, 1H), 3.63 (s, 3H).

EXAMPLE 36

Compound 6 (0.5 g, 1.05 mmol) was dissolved in CH$_2$Cl$_2$ (50 mL). Neat BF$_3$•EtO$_2$ (0.216 mL) was added via syringe at −78° C. The temperature was allowed to come to room temperature over night. Solvent was removed in vacuo, and the resulting solid was suspended in methanol and placed in the freezer for 2 hours. Filtration and washing with cold methanol yielded Compound 36 as a purple solid (320 mg, 64%). m.p. 238.6–240.5° C. $^1$H NMR (500 MHz, DMSO-d$^6$) δ 10.50 (br s, 1H), 7.98 (s, 1H), 7.48 (m, 3H), 7.41 (m, 2H), 7.36 (m, 1H), 7.10 (d, J=9.0 Hz, 1H), 6.98 (m, 2H), 6.72 (m, 2H), 5.29 (dd, J=5.2,4.7 Hz, 1H), 5.08 (dd, J=15.9 Hz, 11.6 Hz, 2H), 4.89 (t, J=5.2 Hz, 2H), 4.27 (m, 3H), 3.70, (m, 3H).

EXAMPLE 37

Compound 36 (15 mg, 0.0314 mmol), DMAP (3.84 mg, 0.0314 mmol), and NEt$_3$ (4.81 μL) were dissolved in dry THF (25 mL). Acetoxy acetyl chloride (3.4 μL) was added via syringe and the reaction was allowed to stir over night at room temperature. The THF was removed on a rotary evaporator and the resulting solid worked up in ethyl acetate and water. Purification of thecrude solid by silicon gel chromatography, eluting with 1:1 ethyl acetate/petroleum ether, provided compound 37 as a light yellow solid (8.2 mg, 45%). $^1$H NMR (500.1 MHz, DMSO-d$^6$) δ 10.52 (br s, 1H), 7.99 (s, 1H), 7.45 (m, 6H), 7.14 (d, J=9.0 Hz, 1H), 6.97 (m, 2H), 6.72 (m, 2H), 5.32 (dd, J=4.9, 5.0 Hz, 1H), 5.10 (d, J=16.2 Hz, 2H), 4.52 (m, 4H), 4.40 (m, 2H), 4.23 (dd, J=4.9, 11.9 Hz, 1H), 3.72 (m, 1H), 2.50 (m, 2H), 2.02 (s, 3H).

EXAMPLE 38

Compound 38 was prepared as described for Compound 36, using Compound 7 (50.0 mg, 0.0986 mmol) and BF$_3$•EtO$_2$ (0.0224 mL) in CH$_2$Cl$_2$ (50 mL) to provide Compound 38 as a purple solid (6.3 mg, 12%). m.p. 248.0–249.0° C. $^1$H NMR (500 MHz, DMSO-d$^6$) δ 10.41 (br s, 11H), 7.94 (s, 1H), 7.43 (m, 6H), 7.07 (d, J=9.0 Hz, 1H), 6.71 (d, J=8.4 Hz, 1H), 6.56 (m, 2H), 5.27 (dd, J=5.5, 4.3 Hz, 1H), 5.07 (q, J=11.6 Hz, 2H), 4.88 (t, J=5.3 Hz, 1H), 4.28 (m, 3H), 3.65 (m, 3H).

EXAMPLE 39

Compound 39 was prepared as described for Compound 36, using Compound 8 (55 mg, 0.108 mmol) and BF$_3$•EtO$_2$ (226 μL) in CH$_2$Cl$_2$ (50 mL) to provide Compound 38 as a purple solid (3.6 mg, 7%). m.p.>300.0° C. $^1$H NMR (500 MHz, DMSO-d$^6$) δ 10.49 (br s, 1H), 7.98 (s, 1H), 7.42 (m, 6H), 7.10 (d, J=9.0 Hz, 1H), 6.86 (d, J=8.0 Hz, 1H), 6.30 (m, 2H), 5.31 (dd, J=4.6, 5.1 Hz, 1H), 5.08 (dd, J=11.7, 15.4 Hz, 2H), 4.88 (t, J=6.8 Hz, 2H), 4.27 (m, 2H), 4.16 (dd, J=4.6, 11.7 Hz, 1H), 3.68 (m, 3H), 3.62 (s, 3H).

EXAMPLE 40

Compound 10 (95 mg, 0.26 mmol) was partially solubilised in dichloromethane (15 mL). Trimethylsilyl trifluoromethanesulfonate (65 μL, 0.30 mmol) was added and the reaction left to stir at room temperature for 1 h. Standard aqueous workup and purification by silica gel chromatography, eluting with ethyl acetate, provided compound 40 as a dark purple solid (25 mg, 26%). m.p. 280–282° C. $^1$H NMR (500 MHz, DMSO-d$^6$) 3.64 (1H, dd, J 10.0, 16.5), 3.71 (2H, dt, J 5.3, 5.3), 3.92 (1H, dd, J 2.5, 16.5), 4.30 (m, 2H), 4.89 (1H, t, J 5.3), 5.10 (1H, dd, J 2.5, 10.0), 6.78 (1H, dd, J 7.5, 7.5), 6.98 (1H, dd, J 7.6, 7.6), 7.19 (2H, m), 7.26 (1H, d, J 7.3), 7.55 (1H, d, J 7.8), 8.02 (1H, s), 10.58 (s, 1H).

EXAMPLE 41

Compound 12 (20 mg, 0.046 mmol) was partially solubilised in dichloromethane (2 mL), boron trifluoride diethyl etherate (11 μL, 0.055 mmnol) added and the reaction left to stir at room temperature for 5 hours. The solvent was removed in vacuo and the resulting residue dissolved in ethyl acetate (10 mL). The organic solution was washed with saturated sodium bicarbonate solution (10 mL), water (10 mL), brine (10 mL), dried over anhydrous magnesium sulfate and concentrated in vacuo. Purification by silica gel chromatography, eluting with 1:1 hexanes/ethyl acetate, provided compound 41 as a dark purple solid. m.p. 238–242° C. $^1$H NMR (500 MHz, DMSO-d$^6$) δ 3.64 (1H, dd, J 10.0, 16.7, CH), 3.87 (1H, dd, J 2.8, 16.8, CH), 5.03 (2H, s, benzylic CH$_2$), 5.11 (1H, dd, J 2.8, 9.9, CH), 6.68 (1H, dd, J 2.5, 8.7, ArH), 6.75 (1H, d, J 8.7, ArH), 6.98 (1H, d, J 2.2, ArH), 7.11 (1H, d, J 7.5, ArH), 7.16 (1H, dd, J 7.6, 7.6, ArH), 7.30 (1H, dd, J 7.2, 7.2, ArH), 7.37 (2H, dd, J 7.4, 7.4, 2 ArH), 7.42 (3H, m, 3 ArH), 7.93 (1H, d, J 2.7, ArH), 10.49 (1H, s, maleamide NH), 11.75 (1H, br, indole NH). HRMS (m/z) Cal'd for C$_{27}$H$_{19}$N$_3$O$_3$ 433.14264. Found 433.1420.

EXAMPLE 42

A solution of 2,3-dichloro-5,6-dicyano-1,4-benzoquinone (122 mg, 0.540 mmol) in 1,4-dioxan (5 mL) was added dropwise to a solution of compound 24 (80.0 mg, 0.240 mmol) in 1,4-dioxan (5 mL) and the reaction left to stir at room temperature for 2 hours. The solvent was removed in vacuo and the resulting residue purified by silica gel chromatography, eluting with 1:1 hexanes/ethyl acetate, to provide compound 41 as a dark purple solid (43 mg, 54%). mp>300° C. HRMS (m/z) Cal'd for C$_{20}$H$_{11}$N$_3$O$_3$ 325.0851. Found 325.0855.

EXAMPLE 43 and 44

Compound 42 was dissolved in methanol and treated with 3 portions of sodium borohydride, at 15 minute intervals. The solution was stirred for an additional 60 minutes before being quenched with 1M HCl and extracted with ethyl acetate. The crude product contained a 1:1 mixture of regeoisomers, one of which was isolated pure by tituration with acetone. MajorIsomer: $^1$H NMR (200 MHz, DMSO-d$^6$) δ 11.39 (s, 1H), 8.56 (s, 1H), 8.07 (d, J=2.4 Hz, 1H), 7.91 (d, J=8.6 Hz, 1H), 7.58 (d, J=7.7 Hz, 1H), 7.51 (s, 1H), 7.49 (d, J=7.7 Hz, 1H), 7.25 (d, J=8.0 Hz, 1H), 7.17–7.07 (m, 3H), 6.56 (d, J=10.0 Hz, 1H), 6.39 (d, J=10.0 Hz, 1H). MS (EI, m/z) M$^+$=327.

EXAMPLE 47

Compound 2 (50 mg, 0.14 mmol) was stirred with TMSOTf (32.4 μL, 0.168 mmol) in CH$_2$Cl$_2$ (5 mL) for 3 days. Removal of volatiles and purification by silica gel chromatography, eluting with 3:2 hexanes\ethyl acetate, yielded a deep purple solid in 67% yield. $^1$H-NMR (200 MHz, DMSO-d$^6$) δ 11.82 (s, 1H), 10.93 (s, 1H), 7.97 (d, J=3.5 Hz, 1H), 7.68 (s, 1H), 7.45 (m, 1H), 7.38 (m, 1H), 7.30 (d, J=7.8 Hz, 1H), 7.06 (m, 3H), 3.95 (s, 3H).

EXAMPLE 48:

Compound 34 (50 mg, 0.14 mmol) was stirred with TMSOTf (32.4 liL, 0.168 mmol) in CH$_2$Cl$_2$ (5 mL) for 3 days. Removal of volatiles and purification by silica gel chromatography, eluting with 3:2 hexanes\ethyl acetate, yielded compound 48 as deep purple solid in 42% yield. m.p. >300 ° C. $^1$H NMR(200 MHz, DMSO-d$^6$) δ 11.94 (s, 1H), 10.96(s, 1H), 8.01 (d, J=2.6 Hz, 1H), 7.58 (d, J=7.2 Hz, 1H), 7.40 (d, J=9.1 Hz, 1H), 7.29 (t, J=9.1 Hz, 1H), 7.26 (d, J=9.1 Hz, 1H), 6.95 (d, J=2.6 Hz, 1H), 6.69 (dd, J=2.6, 9.1 Hz, 1H), 3.77 (s, 3H). MS (EI, m/z) M$^+$=355.

EXAMPLE 49

Compound 4 (392 mg, 1.00 mmol) was dissolved in methylene chloride (25 mL) and treated with neat TMSOTf (215 μL, 1.11 mmol). After stirring over night the volatiles were removed in vacuo and the resulting material purified by silica gel chromatography, eluting with 2:1 petroleum ether/acetone, to provide compound 49 as a purple solid in 31% yield. $^1$H NMR (200 MHz, DMSO-d$^6$) δ 11.70 (br s, 1H), 11.00 (br s, 1H), 7.94 (s, 1H), 7.60 (s, 1H), 7.26 (d, J=9.0 Hz, 1H), 7.04 (d, J=9.0 Hz, 1H), 6.98 (d, J=2.4 Hz, 1H), 6.78 (dd, J=2.5, 9.0 Hz, 1H), 3.93 (s, 3H), 3.76 (s, 1H).

EXAMPLE 50

Compound 47 (50 mg, 0.141 mmol), triethylamine (22 liL, 0.154 mmol), DIC (24 μL, 0.154 mmol), Boc-Gly-OH (27 mg, 0.154 mmol), and DMAP (2 mg) were dissolved in THF and refluxed for 16 hours. Volatiles were removed under reduced pressure and purification by silica gel chromatography, eluting with 25:1 methylene chloride/methanol, followed by preparative TLC, eluting with 25:1 methylene chloride/methanol, provided compound 46 as a deep red solid in 46% yield. $^1$H NMR (200 MHz, DMSO-d$^6$) δ 11.20(br s,1H), 8.24(s,1H), 8.14(d, J=9.0 Hz, 1H), 7.72 (s,1H), 7.52–7.30(m, 3H), 7.21(d, J=9.0 Hz, 1H), 7.1 1(m, 2H), 4.47(d, J=5.0 Hz, 2H), 3.96(s, 3H), 1.43 (s, 9H).

EXAMPLE 51

Compound 47 (25 mg, 0.070), triethylamine (11 μL, 0.077 mmol), acetoxyacetyl chloride (8 μL, 0.077 mmol), and DMAP (1 mg) were dissolved in THF and stirred for 16 hour. Volatiles were removed under reduced pressure and purification by preparative TLC, eluting with 15:1 methylene chloride/methanol, provided compound 46 as a deep red solid in 34% yield. $^1$H NMR (200 MHz, DMSO-d$^6$) δ 11.22 (br s, 1H), 8.24 (s, 1H), 8.16 (d, J=8.1 Hz, 1H), 7.82 (s, 1H), 7.52 (m, 2H), 7.30 (d, J=9.3 Hz, 1H), 7.12 (m, 2H), 5.48 (s, 2H), 4.01 (s, 3H), 2.19 (s, 3H).

EXAMPLE 52

A solution of 2,3-dichloro-5,6-dicyano-1,4-benzoquinone (44.5 mg; 0.20 mmol) in 1,4-dioxan (5 mL) was added dropwise to a solution of compound 35 (38.6 mg; 0.089 mmol) in 1,4-dioxan (5 mL) and the reaction left to stir at room temperature for 2 hours. The solvent was removed in vacuo and the resulting residue purified by silica gel chromatography, eluting with 1:1 hexanes/ethyl acetate, provided compound 52 as a dark purple solid (20 mg; 52%). m.p. 197–200° C. $^1$H NMR (500 MHz, DMSO-d$^6$) δ 5.27 (2H, s, benzylic CH$_2$), 7.02 (1H, ddd, J 7.5, 7.5, 0.9, ArH), 7.07 (1H, ddd, J 7.0, 7.0, 1.3, ArH), 7.11 (1H, d, J 8.8, ArH), 7.26 (1H, d, J 8.8, ArH), 7.38 (5H, m, ArH), 7.52 (m, 2H, d, J 7.0, ArH), 7.72 (1H, d, J 0.7, ArH), 7.96 (1H, d, J 2.8, ArH), 10.92 (1H, s, maleamide NH), 11.83 (1H, br, indole NH). HRMS (m/z) Cal'd for C$_{27}$H$_{17}$N$_3$O$_3$ 431.1270. Found 431.1273.

EXAMPLE 53

Compound 20 (20 mg) was placed in a quartz tube and dissolved in acetonitrile. This solution was placed in front of a 150 W bulb for 48 h. Compound 53 precipitated from solution, was removed by filtration, and washing with aceonitrile, to provide compound 53 as a deep red solid (2 mg, 10%). $^1$H NMR (200 MHz, DMSO-d) δ 13.40 (br s, 1H), 11.48 (br s, 1H), 9.34 (d, J=8.1 Hz, 1H), 8.7 (d, J=8.1 Hz, 1H), 7.79 (d, J=8.1 Hz, 1H), 7.70 (t, J=8.1 Hz, 1H), 7.62–7.55 (m, 4H), 7.41 (t, J=8.1 Hz, 1H).

EXAMPLE 54

Compound 19 (100 mg) was placed in a quartz tube and dissolved in acetonitrile. This solution was placed in front of a 150 W light bulb for 16 hours. Compound 53 precipitated from solution and was removed by filtration, washing with aceonitrile, to provide compound 53 as an orange solid (28 mg, 28%). $^1$H NMR (200 MHz, DMSO-d$^6$) δ 11.75 (br s, 1H), 9.36 (d, J=7.9 Hz, 1H), 8.92 (d, J=7.7 Hz, 1H), 8.13 (d, J=8.3 Hz, 1H), 8.02 (d, J=7.7 Hz, 1H), 7.70–7.52 (m, 4H), 3.15 (s, 3H).

EXAMPLE 55

Compound 18 (20 mg) was placed in a quartz tube and dissolved in acetonitrile. This solution was placed in front of a 150 W light bulb for 48 hours. Compound 53 precipitated from solution and was removed by filtration, and titurated with methylene chloride, to provide compound 55 as a deep red solid (10 mg, 50%). MS (EI, m/z) M$^+$=426.

EXAMPLE 56

Synthesis of 3-(1H-5-bromoindol-3-yl)-1H-pyrrole-2,5-dione

Oxalyl chloride (445 uL, 5.10 mmol) ) was added to a THF (25 ) solution of 5-bromoindole (1.00 g, 5.10 mmol). After stirring at room temperature for 3 hours, volatiles were removed under reduced pressure. Solid acetamide (903 mg, 15.3 mmol) was added to the resulting solid, and the mixture was dissolved in THF (10 mL). After stirring for 3 hours, a 1M solution of KO$^t$Bu (15.3 mL, 15.3 mmol) was added. The resulting, deep purple solution was stirred overnight, quenched with conc H$_2$SO$_4$ (1 mL), stirred for 30 minutes before being diluted with water (20 mL) and ethyl acetate. The aqueous layer was washed with ethyl acetate and the combined organic layers were dried over anhydrous MgSO$_4$, filtered, and the solvent removed under reduced pressure. Purification by silica gel chromatography, eluting with 3:1 to 1:1 petroleum ether/ethyl acetate, provided compound 56 in 45% yield. Compound 56 could be further purified, where necessary, by recrystallization from methanol.

m.p. 270.5–271.0° C. $^1$H NMR (200 MHz, acetone-d$^6$) δ 11.28 (br s, 1H), 9.66 (br s, 1H), 8.48 (d, J=1.5 Hz, 1H), 8.15 (s, 1H), 7.53 (d, J=8.5 Hz, 1H), 7.42 (d, J=8.5 Hz, 1H), 6.82 (s, 1H).

EXAMPLE 57

Synthesis of 3-(N-acetyl-5-bromoindol-3-yl)-1H-pyrrole-2,5-dione

Compound 56 (80 mg, 0.275 mmol), triethylamine (42 μL, 0.3 mmol), DMAP (5 mg), and actetic anhydride (30 μL, 0.3 mmol) were stirred together in THF (5 mL) over night. Standard aqueous workup and purification by silica gel chromatography, eluting with 3:1 petroleum ether/ethyl acetate, provided compound 57 in 51% yield, as a yellow solid. m.p. 271.0–272.9° C. $^1$H NMR (200 MHz, DMSO-d$^6$) δ 11.07 (br s, 1H), 8.49 (s, 1H), 8.25 (d, J=8.5 Hz, 1H), 8.18 (s, 1H), 7.56 (d, J=8.5 Hz, 1H), 7.24 (s, 1H), 2.70 (s, 3H). $^{13}$C NMR (74.5 MHz, DMSO-d$^6$) δ 172.4, 172.2, 169.7, 136.3, 133.9, 131.0, 129.1, 128.6, 123.0, 117.8, 117.3, 109.4.

EXAMPLE 58

3-(N-(N,N-dimethylcarbamoyl)-5-bromoindol-3-yl)-1H-pyrrole-2,5-dione

Compound 56 (80 mg, 0.275 mmol), triethylamine (42 μL, 0.3 mmol), DMAP (5 mg), and N,N-dimethylcarbamoyl chloride (26 μL, 0.3 mmol) were stirred together in THF (5 mL) over night. Standard aqueous workup and recrystallization from ethyl acetate, provided compound 58 in 21% yield, as a yellow solid. The filtrate was approximately 95% pure. m.p. 287.0–288.0° C. $^1$H NMR (200 MHz, DMSO-d$^6$) δ 10.98 (br s, 1H), 8.43 (s, 1H), 8.22 (s, 1H), 7.57 (d, J=8.7 Hz, 1H), 7.48 (d, J=8.7 Hz, 1H), 3.02 (s, 6H).

EXAMPLE 59

Synthesis of 3-(N-benzoyl-5-bromoindol-3-yl)-1H-pyrrole-2,5-dione

Compound 56 (80 mg, 0.275 mmol), triethylamine (42 μL, 0.3 mmol), DMAP (5 mg), and benzoyl chloride (52 μl, 0.3 mmol) were stirred together in THF (5 mL) over night. Standard aqueous workup and recrystallization from ethyl acetate, provided compound 59 in 51% yield, as a yellow solid.

EXAMPLE 60

3-(N-(p-toluenesulfoiiyl)-5-bromoindol-3-yl)-1H-pyrrole-2,5-dione

Compound 56 (50 mg, 0.172 mmol), DMAP (44 mg, 260 mmol), and p-toluenesulfonyl chloride (33 mg, 0.172 mmol) were refluxed in THF (5 mL) for 48 hours. Standard aqueous workup and purification by silica gel chromatography, eluting with 4:1 petroleum ether/ethyl acetate, provided compound 60 in 91% yield, as a yellow solid. m.p. 262.0–263.8° C. $^1$H NMR (200 MHz, DMSO-d$^6$) δ 11.13 (s, 1H), 8.54 (s, 1H), 8.23 (s, 1H), 7.93 (d, J=8.2 Hz, 2H), 7.93 (d, J=8.8 Hz, 1H), 7.58 (dd, J=2.1, 8.8 Hz, 1H), 7.40 (d, J=8.2 HZ, 2H), 7.32 (s, 1H), 2.31 (s, 3H).

EXAMPLE 61

3-(N-(1-naphthylenesulfonyl)-5-bromoindol-3-yl)-1H-pyrrole-2,5-dione

Compound 56 (146 mg, 0.50 mmol), triethylamine (77 μL, 0.55 mmol), DMAP (10 mg), and 1-naphthylenesulfonyl chloride (113 mg, 0.5 mmol) were refluxed in THF (5 mL) for 48 hours. Standard aqueous workup and purification by silica gel chromatography, eluting with 3:1 petroleum ether/ ethyl acetate, provided compound 61 in 73% yield, as an off white solid. $^1$H NMR (200 MHz, DMSO-d$^6$) δ 11.14 (br s, 1H), 8.78 (s, 1H), 8.54 (d, J=7.4 Hz, 1H), 8.50 (d, J=8.2 Hz, 1H), 8.36 (d, J=8.2 Hz, 1H), 8.20 (s, 1H), 8.08 (d, J=7.8 Hz, 1H), 7.79–7.63 (m, 4H), 7.49 (d, J=9.0 Hz, 1H), 7.30 (s, 1H). $^{13}$C NMR (74.5 MHz, DMSO-d$^6$) δ 172.4, 172.2, 169.7, 136.3, 133.9, 131.0, 129.1, 128.6, 123.0, 117.8, 117.3, 109.4.

EXAMPLE 62

3-(N-(2-naphthylenesulfonyl)-5-bromoindol-3-yl)-1H-pyrrole-2,5-dione

Compound 56 (146 mg, 0.50 mmol), triethylamine (77 μL, 0.55 mmol), DMAP (10 mg), and 2-naphthylenesulfonyl chloride (1 13 mg, 0.5 mmol) were refluxed in THF (5 mL) for 48 hours. Standard aqueous workup and purification by silica gel chromatography, eluting with 3:1 petroleum ether/ethyl acetate, provided compound 62 in 48% yield, as an off white solid. $^1$H NMR (200 MHz, DMSO-d$^6$) δ 11.14 (br s, 1H), 8.96 (s, 1H), 8.64 (s, 1H), 8.26–8.22 (m, 2H), 8.10 (d, J=9.0 Hz, 1H), 8.05–7.98 (m, 1H), 7.99 (dd, J=2.0, 8.7 Hz, 1H), 7.747.65 (m, 3H), 7.57 (dd, J=1.7, 9.0 Hz, 1H), 7.31 (s, 1H). $^{13}$CNMR(74.5 MHz, DMSO-d$^6$) δ 172.4, 172.2, 135.8, 135.1, 132.9, 132.7, 131.5, 130.5, 130.3, 130.2, 129.8, 129.6, 129.3, 128.8, 128.3, 128.0, 123.8 (2 C's), 121.1, 117.8, 115.2, 110.5.

EXAMPLE 63

Synthesis of 3-(N-dansyl-5-bromoindol-3-yl)-1H-pyrrole-2,5-dione

Compound 56 (146 mg, 0.50 mmol), triethylamine (77 μL, 0.55 mmol), DMAP (10 mg), and dansyl chloride (202 mg, 0.75 mmol) were refluxed in THF (5 mL) for 48 hours. Standard aqueous workup and purification by silica gel chromatography, eluting with 3:1 petroleum ether/ethyl acetate, provided compound 63 in 42% yield, as an off white solid. $^1$H NMR (200 MHz, DMSO-d$^6$) δ 11.14 (br s, 1H), 8.78 (s, 1H), 8.57 (d, J=7.2 Hz, 1H), 8.54 (d, J=7.2 Hz, 1H), 8.24 (s, 1H), 8.11 (d, J=8.8 Hz, 1H), 7.74 (J, J=8.4 Hz, 2H), 7.66 (d, J=8.0 Hz, 1H), 7.58 (d, J=8.6 Hz, 1H), 7.53 (d, J=8.8 Hz, 1H), 7.33 (s, 1H), 7.20 (d, J=7.7 Hz, 11H), 2.74 (s, 6H). $^{13}$C NMR (74.5 MHz, DMSO-d$^6$) δ 171.8, 171.6, 151.6, 135.3, 132.4, 132.1, 130.8, 129.8, 129.2, 128.5, 128.4, 128.1, 127.9, 123.4, 123.3, 117.0, 115.9, 115.4, 114.3, 113.1, 109.1, 44.4.

EXAMPLE 64

Synthesis of 3-(1-H-5-benzyloxyindol-3-yl)-1H-pyrrole-2,5-dione

Compound 64 was prepared in a manner similar manner to compound 56, using 5-benzyloxyindole (2.00 g, 8.96 mmol), oxalyl chloride (0.82 mL, 9.41 mmol), acetamide (1.70 g, 28.7 mmol), and a 1M solution of KO$^t$Bu (45 mL, 44.8 mmol). Standard workup and purification first by silica gel chromatography, eluting with 3:1 petroleum ether/ethyl acetate, followed by recrystallization from MeOH, provided compound 64 as an orange solid in 53% yield. $^1$H NMR (200 MHz, DMSO-d$^6$) δ 11.92 (s, 1H), 10.72 (s, 1H), 8.31 (d, J=3.0 Hz, 1H), 7.53–7.31 (m, 7H), 6.95 (dd, J=3.0, 8.0 Hz, 1H), 6.82 (s, 1H), 5.22 (s, 2H). $^{13}$C NMR (74.5 MHz, DMSO-d$^6$) δ 173.5, 173.3, 154.3, 139.4, 137.7, 131.6, 131.2, 128.4, 127.7, 126.2, 114.8, 113.6, 113.3, 105.3, 103.9, 69.9.

EXAMPLE 65

Synthesis of 3-(N-acetyl-5-benzyloxyindol-3-yl)-1H-pyrrole-2,5-dione

Compound 64 (50 mg, 0.164 mmol), triethylamine (23 1L, 0.164 mmol), acetic anhydride (16 μL, 0.164 mmol), and DMAP (2 mg) were stirred together in THF (5 mL) over night. Standard aqueous workup and purification by silica gel chromatography, eluting with 3:1 petroleum ether/ethyl acetate, provided compound 65 in 78% yield, as a yellow solid.

EXAMPLE 66

Synthesis of 3-(N-benzoyl-5-benzyloxyindol-3-yl)-1H-pyrrole-2,5-dione

Compound 64 (50 mg, 0.164 mmol), triethylamine (23 μL, 0.164 mmol), benzoyl chloride (19 μL, 0.164 mmol), and DMAP (2 mg) were stirred together in THF (5 mL) over night. Standard aqueous workup and purification by silica gel chromatography, eluting with 4:1 petroleum ether/ethyl acetate, provided compound 66 in 51% yield, as a yellow solid. $^1$H NMR (500 MHz, DMSO-d$^6$) δ 10.99 (s, 1H), 8.27 (s, 1H), 8.24 (d, J=9.0 Hz, 1H), 7.80 (d, J=7.4 Hz, 1H), 7.73 (t, J=7.4 Hz, 1H), 7.63 (t, J=7.4 Hz, 2H), 7.60 (d, J=2.2 Hz, 1H), 7.51 (d, J=7.4 Hz, 2H), 7.41 (t, J=7.4 Hz, 2H), 7.33 (t, J=7.4 Hz, 1H), 7.29 (s, 1H), 7.18 (dd, J=2.3, 9.0 Hz, 1H), 5.28 (s, 2H). $^{13}$C NMR (74.8 MHz, DMSO-d$^6$) δ 172.7, 172.5, 168.0, 156.2, 137.2, 136.7, 133.3, 132.6, 131.8, 130.2, 129.3, 128.83, 128.79, 128.4, 127.83, 127.79, 122.3, 117.0, 155.2, 110.2, 105.0, 70.0.

EXAMPLE 67

3-(N-(2,4-dimethoxybenzoyl)-5-benzyloxyindol-3-yl)-1H-pyrrole-2,5-dione

Compound 64 (76 mg, 0.25 mmol), triethylamine (35 μL, 0.25 mmol), 2,4-dimethoxybenzoyl chloride (30 μL, 0.3 mmol), and DMAP (2 mg) were stirred together in THF (5 mL) over night. Standard aqueous workup and recrystallization from methanol, provided compound 67 in 62% yield, as a yellow solid. $^1$H NMR (500 MHz, DMSO-$^6$) δ 10.97 (s, 1H), 8.24 (d, J=9.0 Hz, 1H), 8.09 (s, 1H), 7.56 (d, J=1.4 Hz, 1H), 7.52 (d, J=9.9 Hz, 1H), 7.50 (d, J=8.6 Hz, 1H), 7.40 (t, J=7.5 Hz, 2H), 7.33 (t, J=7.5 Hz, 1H), 7.25 (s, 1H), 7.14 (dd, J=2.4, 9.0 Hz, 1H), 6.79 (d, J=2.2 Hz, 1H), 6.73 (dd, J=2.2, 9.0 Hz, 1H), 5.26 (s, 2H), 3.89 (s, 3H), 3.73 (s, 3H). $^{13}$C NMR (74.8 MHz, DMSO-d$^6$) δ 172.6, 172.3, 166.4, 163.4, 157.9, 156.0, 137.2, 136.7, 131.9, 131.3, 129.6, 128.8, 128.4, 127.8, 127.7, 122.0, 116.6, 115.4, 115.0, 110.0, 106.1, 104.9, 98.84, 69.9, 55.9, 55.7.

EXAMPLE 68

3-(N-(3,4-dimethoxybenzoyl)-5-benzyloxyindol-3-yl)-1H-pyrrole-2,5-dione

Compound 64 (76 mg, 0.25 mmol), triethylamine (35 μL, 0.25 mmol), 3,4-dimethoxybenoyl chloride (30 μL, 0.3 mmol), and DMAP (2 mg) were stirred together in THF (5 mL) over night. Standard aqueous workup and recrystallization from methanol, provided compound 68 in 74% yield, as a yellow solid. $^1$H NMR (200 MHz, DMSO-d$^6$) δ 11.04 (s, 1H), 8.42 (s, 1H), 8.20 (d, J=9.0 Hz, 1H), 7.51–7.22 (m, 8H), 7.21 (s, 1H), 7.15 (d, J=9.0 Hz, 1H), 5.29 (s, 2H), 3.90 (s, 2H), 3.90 (s, 3H), 3.84 (s, 3H).

EXAMPLE 69

3-(N-(N-Boc-2-aminoacetyl)-5-benzyloxyindol-3-yl)-1H-pyrrole-2,5-dione

Compound 64 (22 mg) was dissolved in THF (5 mL) and refluxed with N-Boc-Gly-OPf (50 mg), and DMAP (2 mg) for 48 hrs. The solvent was removed in vacuo and purified by silica gel chromatography, eluting with 3:1 hexane/ethyl acetate, to provide a 3:1 inseparable mixture of compound 69 and compound 64 (34 mg). $^1$H NMR(200 MHz, DMSO-d$^6$) δ11.10 (s,1H), 8.60(s,1H), 8.40(m,2H), 8.08(m,1H), 7.60–7.35(m,5H), 7.20(s,1H), 4.50(m 2H), 3.50(s,2H), 1.42 (s, 9H).

EXAMPLE 70

Synthesis of 3-(N-tosyl-5-benzyloxyindol-3-yl)-1H-pyrrole-2,5-dione

Compound 64 (100 mg, 0.314 mmol), triethylamine (48 μL, 0.346 mmol), DMAP (10 mg), and p-toluenesulfonyl chloride (66 mg, 0.346 mmol) were refluxed in TTF (5 mL) for 48 hours. Standard aqueous workup and purification by silica gel chromatography, eluting with 3:1 petroleum ether/ethyl acetate, provided compound 70 in 86% yield, as an off white solid. $^1$H NMR (200 MHz, DMSO-d$^6$) δ 11.11 (s, 1H), 8.52 (s, 1H), 7.90 (d, J=8.2 Hz, 2H), 7.88 (d, J=9.4 Hz, 1H), 7.52–7.31 (m, 8H), 7.27 (s, 1H), 7.12 (dd, J=2.2, 9.1 Hz, 1H), 5.19 (s, 2H), 2.31 (s, 3H). $^{13}$C NMR (125.7 MHz, DMSO-d$^6$) δ 172.5, 172.3, 156.1, 146.2, 137.0, 136.3, 133.3, 130.5, 129.7, 128.7, 128.4, 127.8, 127.7, 127.0, 122.8, 115.5, 114.3, 113.6, 111.0, 105.1, 70.0, 21.0.

EXAMPLE 71

3-(N-(4-nitrobenzenesulfonyl)-5-benzyloxyindol-3-yl)-1H-pyrrole-2,5-dione

Compound 64 (50 mg, 0.157 mmol), triethylamine (24 pL, 0.157 mmol), DMAP (2 mg), and 4-nitrobenzenesulfonyl chloride (38 mg, 0.173 mmol) were refluxed in THF (5 mL) for 48 hours. Standard aqueous workup and purification by silica gel chromatography, eluting with 4:1 to 1:1 petroleum ether/ethyl acetate, provided compound 71 in 27% yield, as a light yellow solid. $^1$H NMR (200 MHz, DMSO-d$^6$) δ 11.16 (s, 1H), 8.53 (s, 1H), 8.33 (br s, 4H), 7.92 (d, J=9.0 Hz, 1H), 7.53–7.41 (m, 4H), 7.36 (d, J=7.6 Hz, 2H), 7.32 (s, 1H), 7.15 (dd, J=1.2, 9.0 Hz, 1H), 5.2 (s,2H). $^{13}$C NMR (74.8 MHz, DMSO-d$^6$) δ 172.5, 172.2, 156.4, 151.1, 141.1, 137.0, 136.0, 129.4, 128.9, 128.7, 128.4, 127.9, 127.8, 125.3, 123.5, 120.1, 115.8, 114.3, 112.0, 105.3, 70.0.

EXAMPLE 72

3-(N-(3-nitrobenzenesulfonyl)-5-benzyloxyindol-3-yl)-1H-pyrrole-2,5-dione

Compound 64 (50 mg, 0.157 mmol), triethylamine (24 μL, 0.157 mmol), DMAP (2 mg), and 3-nitrobenzenesulfonyl chloride (38 mg, 0.173 mmol) were refluxed in THF (5 mL) for 48 hours. Standard aqueous workup and purification by silica gel chromatography, eluting with 4:1 to 1:1 petroleum ether/ethyl acetate, provided compound 72 in 42% yield, as a light yellow solid.

EXAMPLE 73

Synthesis of 3-(N-benzyl-5-benzyloxyindol-3-yl)-1H-pyrrole-2,5-dione

Step 1: 5-Benzyloxyindole, intermediate A1 (500 mg, 2.24 mmol), was dissolved in benzene (15 mL) and treated with a 50% sodium hydroxide solution (5 mL) in the presence of tetrabutylammonium hydrogensulfate (76 mg, 0.22 mmol) for 30 minutes, followed by the addition of benzyl bromide (0.40 mL, 3.36 mmol). After stirring for 48 hours, standard aqueous workup provided 800 mg of crude material. Purification by silica gel chromatography, eluting with 10:1 hexanes\ethyl acetate, afforded clean product in 50% yield. $^1$H NMR (200 MHz, CDCl$_3$) δ 7.30 (m, 15H), 6.59 (d, J=2.2 Hz, 1H), 5.22 (m, 4H).

Step 2: Compound 73 was prepared from N-benzyl-5-benzyloxyindole in a similar fashion as that described for compound 56 using N-Benzyl-5-benzyloxyindole (0.96 mmol), oxalyl chloride (83.5 μL, 0.96 mmol), acetamide (0.15 g, 2.55 mmol), and 1M THF solution of KO$^t$Bu (4.1 mL, 4.07 mmol). The reaction mixture was stirred for 3 days at room temperature. Standard workup and purification using silica gel chromatography, eluting with 3:1 hexanes/ethyl acetate, provided compound 73 as a yellow solid in 21% overall yield. $^1$H NMR (200 MHz, DMSO-d$^6$) δ 10.77 (s, 1H), 8.50 (s, 1H), 7.38 (m, 12H), 6.95 (dd, J=2.15; 8.97 Hz, 1H), 6.86 (s, 1H), 5.51 (s, 2H).

EXAMPLE 74

3-(N-(3-pyridinylmethylene)-5-benzyloxyindol-3-yl)-1H-pyrrole-2,5-dione

Step 1: 5-Benzyloxyindole (500 mg, 2.24 mmol) was dissolved in THF (20 mL) and treated with 1M KO$^t$Bu in THF (4.48 mL, 4.48 mmol). After stirring for 3 hours, 3(bromomethyl)pyridine hydrobromide (1.13 g, 4.48 mmol) was added and the reaction mixture was stirred for an additional 24 hrs. Standard aqueous workup and purification by silica gel chromatography, eluting with 4:1 hexane/ethyl acetate, provided N-(43-pyridinylmethylene)-5-benzyloxyindole (421 mg, 68%). $^1$H NMR (200 MHz, CDCl$_3$) δ 8.50 (s, 2H), 7.55–7.25 (m, 5H), 7.54–7.04 (m, 5H), 6.84 (dd, J=2.3, 8.9 Hz, 1H), 6.49 (d, J=3.2 Hz, 1H), 5.24 (s, 2H), 5.00 (s, 2H). MS (EI, m/z) M$^+$=314.

Step 2: Compound 74 was prepared from N-(3-pyridinyl-methylene)-5-benzyloxyindole in a similar fashion as that described for compound 56 using N-(2,3-dimethoxybenzyl)-5-benzyloxyindole (100 mg, 0.318 mmol), oxalyl chloride (27 μL, 0.318 nunol), acetamide (56 mg, 0.954 mmol), and 1M THF solution of KO$^t$Bu (1.60 mL, 1.60 mmol). The reaction mixture was stirred for 3 days at room temperature. Standard workup and purification using silica gel chromatography, eluting with 3:1 hexanes/ethyl acetate, provided compound 74 as a yellow solid in 4% yield. MS (EI, m/z) M$^+$=409.

EXAMPLE 75

3-(N-(2,3-dimethoxybenzyl)-5-benzyloxyindol-3-yl)-1H-pyrrole-2,5-dione

Step 1: 5-Benzyloxyindole (500 mg, 2.24 mmol) was dissolved in THF (20 mL) and treated with 1M KO$^t$Bu in THF (2.24 mL, 2.24 mmol). After stirring for 3 hours, 3,5-dimethoxybenzyl bromide (460 mg, 2.46 mmol) was added and the reaction mixture was stirred for an additional 24 hrs. Standard aqueous workup and purification by silica gel chromatography, eluting with 5:1 hexane/ethyl acetate, provided N-2,3-dimethoxybenzyl)-5-benzyloxyindole (465 mg, 76%). $^1$H NMR (200 MHz, CDCl$_3$) δ 8 7.46 (d, J=7.9 Hz, 2H), 7.38 (t, J=7.9 Hz, 2H), 7.32 (t, J=7.9 Hz, 1H), 7.23 (s, 1H), 7.18 (m, 2H), 7.09 (d, J=2.5 Hz, 1H), 6.91 (m, 1H), 6.45 (d, J=2.0 Hz, 1H), 6.34 (m, 1H), 6.23 (d, J=2.5 Hz, 1H), 5.19 (s, 2H), 5.08 (s, 2H), 3.80 (s, 6H).

Step 2: Compound 75 was prepared from N-2,3-dimethoxybenzyl)-5-benzyloxyindole in a similar fashion as that described for compound 56 using N-(2,3-dimethoxybenzyl5-benzyloxyindole (250 mg, 0.56 mmol), oxalyl chloride (49 μL, 0.56 mmol), acetamide (99 mg, 1.68 mmol), and 1M THF solution of KO$^t$Bu (2.80 mL, 2.80 mmol). The reaction mixture was stirred for 3 days at room temperature. Standard workup and purification using silica gel chromatography, eluting with 3:1 hexanes/ethyl acetate, provided compound 75 as a yellow solid in 56% yield. MS (EI, m/z) M$^+$=444.

EXAMPLE 76

3-(N-(3-fluorobenzyl)-5-benzyloxyindol-3-yl)-1H-pyrrole-2,5-dione

Step 1: 5-Benzyloxyindole (500 mg, 2.24 mmol) was dissolved in THF (20 mL) and treated with 1M KO$^t$Bu in THF (2.24 mL, 2.24 mmol). After stirring for 3 hours, 3-fluorobenzyl bromide (274 μL, 2.24 mmol) was added and the reaction mixture was stirred for an additional 24 hrs. Standard aqueous workup and purification by silica gel chromatography, eluting with 5:1 hexanes/ethyl acetate, provided N-(2-fluorobenzyl)-5-benzyloxyindole (325 mg, 44%). $^1$H NMR (200 MHz, CDCl$_3$) δ 7.55–7.29 (mn, 5H), 7.28–7.05 (m, 3H), 7.04–6.81 (m, 5H), 6.49 (dd, J=0.7, 3.1 Hz, 1H), 5.26 (s, 2H), 5.10 (s, 2H). MS (EI, m/z) M$^+$=33 1.

Step 2: Compound 76 was prepared from N-(2-fluorobenzyl)-5-benzyloxyindole in a similar fashion as that described for compound 56 using N-2{fluorobenzyl)-5-benzyloxyindole (250 mg, 0.75 mmol), oxalyl chloride (65 μL, 0.75 mmol), acetamide (132 mg, 2.25 mmol), and 1M THF solution of KO$^t$Bu (3.75 mL, 3.75 mmol). The reaction mixture was stirred for 3 days at room temperature. Standard workup and purification using silica gel chromatography, eluting with 3:1 hexanes/ethyl acetate, provided compound 76 as a yellow solid in 43% overall yield $^1$H NMR (200 MHz, DMSO-d$^6$) δ 10.78 (s, 1H), 8.52 (s, 1H), 7.46 (m, 3H), 7.36 (m, 4H), 7.09 (m, 2H), 7.05 (s, 1H), 7.00 (m, 2H), 6.87 (s, 1H), 5.53 (s, 2H), 5.20 (s, 2H). 13C NMR (DMSO-d$^6$) δ 172.2, 171.9, 153.4, 138. MS (EI, m/z) M$^+$=426.

EXAMPLE 77

3-(N-(4-fluorobenzyl)-5-benzyloxyindol-3-yl)-1H-pyrrole-2,5-dione

Step 1:
5-Benzyloxyindole (500 mg, 2.24 mmol) was dissolved in THF (20 mL) and treated with 1M KO$^t$Bu in THF (2.24 mL, 2.24 mmol). After stirring for 3 hours, 4fluorobenzyl bromide (274 μL, 2.24 mmol) was added and the reaction mixture was stirred for an additional 24 hrs. Standard aqueous workup and purification by silica gel chromatography, eluting with 5:1 hexane/ethyl acetate, provided N-(4-fluoro)benzyl-5-benzyloxyindole (455 mg, 61%). $^1$H NMR (200 MHz, CDCl$_3$) δ 7.60–7.38 (m, 5H), 7.23 (d, J=3.1 Hz, 1H), 7.18–6.92 (m, 7H1), 6.50 (d, J=3.1 Hz, 1H), 5.23 (s, 2H), 5.12 (s, 2H). MS (EI, m/z) M$^+$=331.

Step 2: Compound 77 was prepared from N-(4-fluorobenzyl)-5-benzyloxyindole in a similar fashion as that described for compound 56 using N-(4fluorobenzyl}5-benzyloxyindole (250 mg, 0.75 mmol), oxalyl chloride (65 μL, 0.75 mmol), acetamide-(132 mg, 2.25 mmol), and 1M THF solution of KO$^t$Bu (3.75 mL, 3.75 mmol). The reaction mixture was stirred for 3 days at room temperature. Standard workup and purification using silica gel chromatography, eluting with 3:1 hexanes/ethyl acetate, provided compound 77 as a yellow solid in 42% overall yield. $^1$H NMR (200 MHz, DMSO-d$^6$) δ 10.77 (s, 1H), 7.56–7.44 (m, 10H) 7.13 (t, J=8.9 Hz, 2H), 6.96 (dd, J=2.2, 6.8 Mz, 1H), 6.86 (s, 1H), 5.50 (s, 2H), 5.20 (s, 2H). MS (EI, m/z) M$^+$=426.

EXAMPLE 78

3-(N-(methylenephthalimido)-5benzyloxyindol-3-yl)-1H-pyrrole-2,5-dione

Step 1: 5-Benzyloxyindole (500 mg, 2.24 mmol) was dissolved in THF (20 mL) and treated with 1M KO$^t$Bu in THF (2.24 mL, 2.24 mmol). After stirring for 3 hours, N-(bromomethyl) phthalimide (538 mg, 2.24 mmol) was added and the reaction mixture was stirred for an additional 24 hrs. Standard aqueous workup and purification by silica gel chromatography, eluting with 3:1 hexane/ethyl acetate, provided N-(methylenephthalimido)-5-benzyloxyindole (650 mg, 76%). $^1$H NMR (200 MHz, CDCl$_3$) δ 7.83 (d, J=5.5 Hz, 1H), 7.81 (d, J=5.5 Hz, 1H), 7.72–7.65 (m, 2H), 7.45 (m, 1H), 7.42 (d, 3.0 Hz, 2H), 7.40–25 (m, 2H), 7.09 (d, J=2.2 Hz, 1H), 7.00 (dd, J=2.2, 9.0 Hz, 1H), 6.49 (d, J=3.2 Hz, 1H), 5.91 (s, 2H), 5.07 (s, 2H). MS (EI. m/z) M$^+$=382.

Step 2: Compound 78 was prepared from N-(methylenephthalimido)-5-benzyloxyindole in a similar fashion as that described for compound 56 using N-(methylenephthalimido)-5-benzyloxyindole (250 mg, 0.654 mmol), oxalyl chloride (75 mL, 0.654 mmol), acetamide (116 mg, 1.96 mmol), and 1M THF solution of KO$^t$Bu (3.30 mL, 3.30 mmol). The reaction mixture was stirred for 3 days at room temperature. Standard workup and purification using silica gel chromatography, eluting with 2:1 hexanes/ethyl acetate, provided compound 78 as a yellow solid in 32% yield. $^1$H NMR (200 MHz, DMSO-d$^6$) δ 10.80 (s, 1H), 9.50 (br t, 1H), 8.50 (s, 1H), 7.75 (m, 2H), 7.60–7.25 (m, 10H), 7.06 (dd, J=0.7, 8.3 Hz, 1H), 6.86 (s, 1H), 5.64 (br d, J=5.3 Hz, 2H), 5.21 (s, 2H).

EXAMPLE 79

3-(N-(2-naphthylmethylene)-5-benzyloxyindol-3-yl)-1H-pyrrole-2,5-dione

Step 1: 5-Benzyloxyindole (500 mg, 2.24 mmol) was dissolved in THF (20 mL) and treated with 1M KO$^t$Bu in THF (2.24 mL, 2.24 mmol). After stirring for 3 hours, 2-(bromomethyl)naphthylene (246 mg, 2.24 mmol) was added and the reaction mixture was stirred for an additional 24 hrs. Standard aqueous workup and purification by silica gel chromatography, eluting with 5:1 hexane/ehtyl acetate, provided N-(2-naphthylmethylene)-5-benzyloxyindole. $^1$H NMR (200 MHz, CDCl$_3$) δ 7.95–7.81 (m, 4H), 7.64–7.50 (m, 4H), 7.7.47 (m, 1H), 7.43 (m, 1H), 7.39 (m, 1H), 7.30 (dd, J=4.0, 9.8 Hz, 1H), 7.21 (d, J=2.7 Hz, 1H), 7.07 (td, J=2., 8.9 Hz, 1H0, 6.98 (s, 1H), 6.65 (d, J=3.1 Hz, 1H0, 6.65 (d, J=11.6 Hz, 2H), 5.18 (d, J=14.6 Hz, 2H). MS (EI, m/z) M⁺=363.

Step 2: Compound 79 was prepared from N-(2-naphthylmethylene)-5-benzyloxyindole in a similar fashion as that described for compound 56 using N-(2-naphthylmethyl)-5-benzyloxyindole (250 mg, 0.690 mmol), oxalyl chloride (60 μL, 0.69 mmol), acetamide (122 mg, 2.07 mmol), and 1M THF solution of KO$^t$Bu (3.45 mL, 3.45 mmol). The reaction mixture was stirred for 3 days at room temperature. Standard workup and purification using silica gel chromatography, eluting with 3:1 hexanes/ethyl acetate, provided compound 79 as a yellow solid in 49% yield. $^1$H NMR (200 MHz, DMSO-d$^6$) δ 10.77 (s, 1H), 8.57 (s, 1H), 7.82 (m, 3H), 7.6–7.40 (m, 6H), 7.39–7.24 (m, 6H), 6.93 (dd, J=2.1, 9.0 Hz, 1H), 6.88 (s, 1H), 5.68 (s, 2H), 5.12 (s, 2H). MS (EI, m/z) M⁺=458.

EXAMPLE 80

Synthesis of 3-(N-(cyclohexylmethylene)-5-benzyloxyindol-3-yl)-1H-pyrrole-2,5-dione Step 1: 5-Benzyloxyindole (500 mg, 2.24 mmol) was dissolved in THF (20 mL) and treated with 1M KO$^t$Bu in THF (2.24 mL, 2.24 mmol). After stirring for 3 hours, (bromomethyl)cyclohexane (312 μL, 2.24 mmol) was added and the reaction mixture was stirred for an additional 24 hrs. Standard aqueous workup and purification by silica gel chromatography, eluting with 5:1 hexane/ethyl acetate, provided N-(2-naphthylmethylene)-5-benzyloxyindole as a white solid (475 mg, 66%). $^1$H NMR (200 MHz, CDCl$_3$) δ 7.56 (m, 2H), 7.51–7.38 (m, 3H), 7.25 (m, 2H), 7.07 (dd, J=2.5, 6.4 Hz, 1H), 7.02 (dd, J=2.5, 6.4 Hz, 1H), 6.46 (d, J=2.5 Hz, 1H), 5.17 (s, 2H), 3.93 (d, J=4.1 Hz, 2H, 1.91 (m, 1H), 1.88–1.60 (m, 5H), 1.56 (m, 3H), 1.11 (m, 2H). MS (EI, m/z) M⁺=319.

Step 2: Compound 80 was prepared from N-(cyclohexylmethylene)-5-benzyloxyindole in a similar fashion as that described for compound 56 using N-(2-naphthylmethyl)-5-benzyloxyindole (250 mg, 0.78 mmol), oxalyl chloride (68 μL, 0.78 mmol), acetamide (138 mg, 2.34 mmol), and 1M THF solution of KO$^t$Bu (3.90 mL, 3.90 mmol). The reaction mixture was stirred for 3 days at room temperature. Standard workup and purification using silica gel chromatography, eluting with 3:1 hexanes/ethyl acetate, provided compound 80 as a yellow solid in 41% yield. $^1$H NMR (200 MHz, CDCl$_3$) δ 8.23 (s, 1H), 7.52–7.24 (m, 8H), 7.02 (dd, J=2.4, 9.0 Hz, 1H), 6.42 (s, 1H), 5.13 (s, 2H), 3.93 (d, J=7.1 Hz, 2H), 1.85 (m, 1H), 1.79–1.57 (m, 4H), 1.30–0.95 (m, 6H). MS (EI, m/z) M$^{+1}$=415.

EXAMPLE 81

Synthesis of 3-(N-octyl-5-benzyloxyindol-3-yl)-1H-pyrrole-2,5-dione

Step 1: N-Octyl-5-benzyloxyindole was prepared by general method A. 5-Benzyloxyindole (500 mg, 2.24 mmol) was dissolved in THF (20 mL) and treated with 1M KO$^t$Bu in THF (3.81 mL, 3.8 mmol). After stirring for 3 hours, 1-bromooctane (0.39 mL, 2.24 mmol) was added and the reaction mixture was stirred for an additional 24 hrs. Standard aqueous workup and purification by silica gel chromatography, eluting with 3:1 hexane/ethyl acetate, provided N-octyl-5-benzyloxyindole. $^1$H NMR (200 MHz, CDCl$_3$) δ 7.68 (m, 7H), 7.35 (m, 2H), 6.78 (d, J=2.9 Hz, 1H), 5.40 (s, 2H), 4.23 (t, J=7.0 Hz, 2H), 2.05 (broad t, J=6.5 Hz, 2H), 1.62 (broad s, 10H), 1.31 (t, J=6.2 Hz, 3H)

Step 2: Compound 81 was prepared from N-octyl-5-benzyloxyindole in a similar fashion as that described for compound 56. To a solution of N-octyl-5-benzyloxyindole in THF was added oxalyl chloride (0.12 mL, 1.4 mmol), stirred for 24 hours followed by addition of acetamide (0.22 g, 3.74 mmol), and 1M THF solution of KO$^t$Bu (5.95 mL, 5.95 mmol). The reaction mixture was stirred for 3 days at room temperature. Standard workup and purification using silica gel chromatography, eluting with 5:1 hexanes/ethyl acetate, yielded compound 81 as an orange solid in 30% overall yield.

$^1$H NMR (200 MHz, DMSO-d$^6$) δ 10.73 (s, 1H), 8.33 (s, 1H), 7.41 (m, 7H), 7.01 (d, J=2.4 Hz, 1H), 6.80 (s, 1H), 5.21 (s, 2H), 4.23 (t, J=2.7 Hz, 2H), 1.72 (m, 2H), 1.21 (s, 10H),

EXAMPLE 82

3-(N-(2-hydroxyethyl)-5-benzyloxyindol-3-yl)-1H-pyrrole-2,5-dione

Step 1: 5-Benzyloxyindole (10.00 g, 44.8 mmol) and n-Bu$_4$NHSO$_4$ (1.00 g) were partitioned between toluene (500 mL) and 50% aqueous NaOH (200 mL). This solution was stirred vigerously for 30 minutes before neat ethyl bromoacetate (5.0 mL, 44.8 mmol) was added. After stirring for an additional 2 hours the mixture was diluted with diethyl ether and water. The aqueous layer was washed with diethyl ether before being acidified with 6N HCl. The resulting solid was filtered off, washed with water, and dried in vacuo to pride of N-(5-benzyloxyindole)acetic acid as an off white solid (12.21 g, 98%).

Step 2: Crude N-(5-benzyloxyindole)acetic acid (12.21 g, 44.2 mmol) was dissolved in THF (100 mL) and added dropwise to a cold THF (500 mL) suspension of LiAlH4 (1.78 g, 44.2 mmol). After stirring at room temperature for 1 hour 2M HCl was added, followed by diethyl ether. The organic layer was subjected to standard aqueous workup to provide N-(2-hydroxyethyl)-5-benzyloxyindole in yield as a clear oil (11.09 g, 94%).

$^1$H NMR (500 MHz, CDCl$_3$) δ 7.51 (d, J=11.8 Hz, 1H), 7.50 (d, J=7.4 Hz, 2H), 7.41 (t, J=7.4 Hz, 2H), 7.34 (t, J=7.4 Hz, 1H), 7.22 (d, J=8.9 Hz, 1H), 7.19 (s, 1H), 7.07 (d, J=2.5 Hz, 1H), 6.99 (d, J=8.9 Hz, 1H), 6.42 (d, J=2.5 Hz, 1H), 5.11 (s, 2H), 4.10 (m, 2H), 3.75 (m, 2H), 2.01 (br s, 1H). MS (EI, m/z) M⁺=267.

Step 3: Crude N-(2-hydroxyethyl)-5-benzyloxyindole (11.09 g, 42.1 mmol), acetic anhydride (4.36 mL, 46.3 mmol), triethylamine (6.50 mL, 46.3 mmol), and DMAP (100 mg) were stirred together in THF for 1 hour before standard aqueous workup provided N-(2-acetoxyethyl)-5-benzyloxyindole in yield as a clear oil (13.0 g, 99%). $^1$H NMR (500 MHz, CDCl$_3$) δ 7.51 (d, J=8.1 Hz, 2H), 7.42 (t, J=8.1 Hz, 2H), 7.35 (s, 1H), 7.27 (d, J=8.9 Hz, 1H), 7.21 (d, J=2.4 Hz, 1H), 7.09 (d, J=3.1 Hz, 1H), 7.01 (dd, J=2.4, 8.1 Hz, 1H), 6.47 (dd, J=0.8, 3.1 Hz, 1H), 5.14 (s, 2H), 4.37 (t, J=5.0 Hz, 2H), 4.31 (t, J=5.0 Hz, 2H), 2.02 (s, 3H). $^{13}$C NMR (50 MHz, CDCl$_3$) δ 170.6, 153.3, 137.7, 131.6, 128.9, 128.5 (2 C's), 128.4, 127.7, 127.5 (2 C's), 112.8, 109.8, 104.,3 101.4, 70.9, 63.0, 45.0, 20.7. MS (EI, m/z) M⁺=309.

Step 4: Compound 82 was prepared in a manner similar manner to compound 69, using N-(2-acetoxyethyl)-5-benzyloxyindole (2.00 g, 13.5 mmol), oxalyl chloride (1.18 mL, 13.5 mmol), acetamide (2.67 g, 40.5 mmol), and a 1M solution of KO$^t$Bu (68.0 mL, 68.0 mmol). Standard workup and purification first by silica gel chromatography, eluting with 2:1 petroleum ether/ethyl acetate, provided compound 82 as a deep red solid in 62% yield. 1H NMR (200 MHz, DMSO-d$^6$) δ 10.72 (s, 1H), 8.36 (s, 1H), 7.55–7.31 (m, 7H), 6.98 (dd, J=2.0, 9.0 Hz, 1H), 6.80 (s, 1H), 5.22 (s, 2H), 4.94 (t, J=5.1 Hz, 1H), 4.28 (m, 2H), 3.70 (m, 2H).

EXAMPLE 83

3-(N-(O-acetoxyethyl)-5-benzyloxyindol-3-yl)-1H-pyrrole-2,5 dione

Compound 82 (76 mg, 0.25 mmol), triethylamine (35 μL, 0.25 mmol), acetic anhydride (30 μL, 0.3 mmol), and DMAP (2 mg) were stirred together in THF (5 mL) over night. Standard aqueous workup and recrystallization from methanol, provided compound 83 in 62% yield, as a yellow solid.
$^1$H NMR (200 MHz, CDCl$_3$) δ 8.31 (d, J=12.1 Hz, 1H), 7.48–7.24 (m, 7H), 7.06 (td, J=2.0, 8.2 Hz, 1H), 6.44 (d, J=12.1 Hz, 1H), 5.13 (s, 2H), 4.38 (s, 4H), 1.98 (s, 3H).

EXAMPLE 84

3-(N-(2-(3,4-dimethoxy)benzoyl)oxyethyl)-5-benzyloxyindol-3-yl)-1H-pyrrole-2,5-dione Compound 82 (76 mg, 0.25 mmol), triethylamine (35 μL, 0.25 mmol), 3,4-dimethoxybenzoyl chloride (60 mg, 0.3 mmol), and DMAP (2 mg) were stirred together in THF (5 mL) over night. Standard aqueous workup and recrystallization from methanol, provided compound 84 in 75% yield, as a light yellow solid. $^1$H NMR (200 MHz, CDCl$_3$) δ 10.72 (s, 1H), 8.49 (s, 1H), 7.67 (d, J=9.0 Hz, 1H), 7.52–7.31 (m, 7H), 7.27 (d, J=1.4 Hz, 1H), 6.99 (d, J=8.7 Hz, 1H), 6.85 (s, 1H), 5.21 (s, 2H), 4.68 (m, 2H), 4.53 (m, 2H), 3.81 (s, 3H), 3.71 (s, 3H).

EXAMPLE 85

Compound 82 (76 mg, 0.25 mmol), triethylamine (35 ML, 0.25 mmol), and phenyl isocyanate were refluxed together in THF (5 mL) over night. Standard aqueous workup and recrystallization from methanol, provided compound 85 in 62% yield, as a yellow solid.

EXAMPLE 86

Synthesis of 3-(1H-5-methoxyindol-3-yl)-1H-pyrrole-2,5-diones

Compound 86 was prepared in a manner similar manner to compound 56, using 5-methoxyindole (2.00 g, 13.5 mmol), oxalyl chloride (1.18 mL, 13.5 mmol), acetamide (2.67 g, 40.5 mmol), and a 1M solution of KO$^t$Bu (68.0 mL, 68.0 mmol). Standard workup and purification first by silica gel chromatography, eluting with 2:1 petroleum ether/ethyl acetate provided compound 86 as an light orange solid in 62% yield. $^1$H NMR (200 MHz, DMSO-d) δ 11.95 (s, 1H), 10.71 (s, 1H), 8.31 (s, 1H), 7.40 (d, J=8.7 Hz, 1H), 7.32 (d, J=2.2 Hz, 1H), 6.87 (dd, J=2.2, 8.7 Hz, 1H), 6.81 (s, 1H), 3.84 (s, 3H). $^{13}$C NMR (50 MHz, acetone-d$^6$) δ 172.7, 172.5, 155.9, 140.1, 131.8, 131.2, 126.7, 114.94, 114.8, 113.2, 113.0, 105.9, 102.4, 55.2.

EXAMPLE 87

Synthesis of 3-(N-tosyl-5-methoxyindol-3-yl)-1H-pyrrole-2,5-dione

Compound 86 (70 mg, 0.289 mmol), triethylamine (48 μL, 0.347 mmol), DMAP (10 mg), and p-toluenesulfonyl chloride (66 mg, 0.347 mmol) were refluxed in THF (5 mL) for 48 hours. Standard aqueous workup and purification by silica gel chromatography, eluting with 2:1 petroleum ether/ethyl acetate, provided compound 87 in 43% yield, as a light yellow solid.

EXAMPLE 88

3-(N-(4-nitrobenzenesulfonyl)-5-methoxyindol-3-yl)-1H-pyrrole-2,5-dione

Compound 86 (44 mg, 0.182 mmol), triethylamine (32 μL, 0.227 mmol), DMAP (2 mg), and 4-nitrobenzenesulfonyl chloride (50 mg, 0.227 mmol) were refluxed in THF (5 mL) for 48 hours. Standard aqueous workup and purification by silica gel chromatography, eluting with 4:1 to 1:1 petroleum ether/ethyl acetate, provided compound 88 in 17% yield, as a light yellow solid. $^1$H NMR (200 MHz, DMSO-d$^6$) δ 11.15 (s, 1H), 8.52 (s, 1H), 8.33 (br s, 4H), 7.91 (dd, J=1.1, 9.0 Hz, 1H), 7.39 (s,1H), 7.32 (s, 1H), 7.07 (d, J=9.1 Hz, 1H), 3.84 (s, 3H). $^{13}$C NMR (74.8 Hz, DMSO-d$^6$) δ172.4, 172.2, 157.3, 151.1, 141.1, 136, 129.4, 128.9, 128.7, 128.2, 125.3, 123.6, 115.2, 114.3, 112, 104.2, 55.9.

EXAMPLE 89

Synthesis of 3-(N-allyl-5-methoxyindol-3-yl)-1H-pyrrole-2,5-dione

Step 1: 5-Methoxyindole (294 mg, 2.0 mmol) was dissolved in THF (10 mL) and treated with 1M KO$^t$Bu in THF (2.2 mL, 2.2 mmol). After stirring for 1 hour, allyl bromide (190 μL, 2.2 mmol) was added and the reaction mixture was stirred for an additional 2 hrs. Standard aqueous workup provided N-Allyl-5-methoxyindole as an off white solid, which was used without further purification.
$^1$H NMR (200 MHz, CDCl$_3$) δ 7.25 (d, J=9.0 Hz, 1H), 7.13 (d, J=2.5 Hz, 1H), 7.09 (d, J=2.0 Hz, 1H), 6.93 (dd, J=2.0, 9.0 Hz, 1H), 6.51 (d, J=2.5 Hz, 1H), 6.03 (tdd, J=5.4, 10.4, 19.7 Hz, 1H), 5.23 (dd, J=1.1, 10.4 Hz, 1H), 5.14 (dd, J=1.1, 16.9 Hz, 1H), 4.90 (d, J=5.4 Hz, 2H), 3.91 (s, 3H).
Step 2: Compound 89 was prepared from N-Allyl-5-methoxyindole in a similar fashion as that described for compound 56, using the crude N-Allyl-5-methoxyindole from above, oxalyl chloride (192 μL, 2.2 mmol), acetamide (360 mg, 6.0 mmol), and 1M THF solution of KO$^t$Bu (20 mL, 20.0 mmol). Standard workup and purification using silica gel chromatography, eluting with 4:1 to 1:1 petroleum ether/ethyl acetate, yielded a light yellow solid in 60% overall yield. $^1$H NMR (200 MHz, DMSO-d$^6$) δ 10.75 (s, 1H), 8.34 (s, 1H), 7.45 (d, J=9.0 Hz, 1H), 7.33 (d, J=2.0 Hz, 1H), 6.91 (dd, J=2.0, 9.0 Hz, 1H), 6.83 (s, 1H), 6.00 (tdd, J=5.4, 10.4, 19.7 Hz, 1H), 5.19 (dd, J=1.1, 10.4 Hz, 1H), 5.09 (dd, J=1.1, 16.9 Hz, 1H), 4.90 (d, J=5.4 Hz, 2H), 3.85 (s, 3H). $^{13}$C NMR (74.8 Hz, DMSO-d$^6$) δ 173.4, 173.2, 155.5, 138.9, 133.7, 131.4, 126.9, 120.1, 117.6, 115.0, 112.8, 112.1, 104.5, 102.8, 55.7, 48.6.

EXAMPLE 90

Synthesis of 3-(N-allyl-5-hydroxyindol-3-yl)-1H-pyrrole-2,5-dione

Compound 89 (103 mg, 0.366 mmol) and BBr$_3$ (346 mL, 3.66 mmol) were refluxed together in CH$_2$Cl$_2$ for 16 hours. The resulting solution was treated with 2M HCl (5 mL) and extracted with ethyl acetate. A deep blue solid was filtered off, and the organic layer was washed with water, dried over anhydrous Mg$_2$SO$_3$, filtered, and the solvent removed under reduced pressure. The resulting solid was purified by silica gel chromatography, eluting with 2:1 petroleum ether/ethyl acetate, to yield compound 90 as a pail yellow solid in 32% yield.

EXAMPLE 91

Synthesis of 3-(N-tosyl-5-hydroxyindol-3-yl)-1H-pyrrole-2,5-dione

Compound 87 (15 mg, 0.038 mmol) and BBr$_3$ (7.2 μL, 0.076 mmol) were refluxed together in CH$_2$Cl$_2$ for 16 hours. An additional 8 μL of BBr$_3$ was added and the reaction mixture was refluxed for an additional 24 hours. Standard aqueous/ethyl acetate workup and purification of the crude solid by silica gel chromatography, eluting with 2:1 petroleum ether/ethyl acetate, provided compound 91 as a pail yellow solid in 57% yield. $^1$H NMR (200 Hz, DMSO-d$^6$) δ 11.21 (s, 1H), 9.59 (s, 1H), 8.43 (s, 1H), 8.91 (m, 3H), 8.85 (d, J=7.1 Hz, 1H), 7.41 (d, J=7.8 Hz, 2H), 7.25 (m, 1H), 6.94 (s, 1H), 2.38 (s, 3H). $^{13}$C NMR (74.8 Hz, DMSO-d$^6$) δ 172.3, 172.2, 154.9, 146.0, 136.7, 133.5, 130.4, 129.5, 128.9, 127.5, 126.9, 122.2, 114.9, 114.2, 110.7, 106.1, 21.0.

EXAMPLE 92

Synthesis of 3-(1H-indol-3-yl)-1H-pyrrole-2,5-dione

Compound 92 was prepared in a manner similar manner to compound 56, using indole (4.00 g, 19.7 mmol), oxalyl chloride (1.47 mL, 19.7 mmol), acetamide (1.16 g, 19.7 mmol), and a 1M solution of KO$^t$Bu (59.1 mL, 59.1 mmol). Standard workup and purification by titration with acetone provided compound 92 as an orange solid 45% yield. $^1$H NMR (200 MHz, DMSO-d$^6$) δ 12.01 (s, 1H), 10.76 (s, 1H), 8.36 (d, J=7.2 Hz, 1H), 7.95 (d, J=6.8 Hz, 1H), 7.52 (d, J=7.0 Hz, 1H), 7.28–7.15 (m, 2H), 6.77 (s, 1H).

EXAMPLE 93

Synthesis of 3-(N-(p-toluenesulfonyl)indol-3-yl)-1H-pyrrole-2,5-dione

Compound 92 (52 mg, 0.25 mmol), triethylamine (52 μL, 0.375 mmol), DMAP (10 mg), and p-toluenesulfonyl chloride (72 mg, 0.375 mmol) were refluxed in THF (5 mL) for 48 hours. Standard aqueous workup and purification by silica gel chromatography, eluting with 4:1 petroleum ether/ethyl acetate, provided compound 93 in 66% yield, as a light yellow solid. $^1$H NMR (200 MHz, DMSO-d$^6$) δ 11.12 (s, 1H), 8.56 (s, 1H), 8.07 (d, J=7.7 Hz, 1H), 8.02 (d, J=7.7 Hz, 1H), 7.9 (d, J=8.7 Hz, 2H), 7.42 (t, J=7.7 Hz, 1H), 7.40 (d, J=8.3 Hz, 2H), 7.37 (t, J=7.7 Hz, 1H), 7.21 (s, 1H), 2.31 (s, 3H). $^{13}$C NMR (74.8 Hz, DMSO-d$^6$) δ 172.4, 172.3, 146.3, 136.4, 133.9, 133.4, 130.6, 129.1, 127.6, 127.1, 126.0, 124.6, 123.0, 121.5, 113.4, 111.0, 21.1.

EXAMPLE 94

3-(N-(4-acetamindobenzenesulfonyl)indol-3-yl)-1H-pyrrole-2,5-dione

Compound 92 (52 mg, 0.25 mmol), triethylamine (52 μL, 0.375 mmol), DMAP (10 mg), and 4-acetamindobenzene-sulfonyl chloride (88 mg, 0.375 mmol) were refluxed in THF (5 mL) for 48 hours. Standard aqueous workup and purification by silica gel chromatography, eluting with 2:1 to 1:1 petroleum ether/ethyl acetate, provided compound 94 in 33% yield, as a light yellow solid. $^1$H NMR (200 MHz, DMSO-d$^6$) δ 11.11 (s, 1H), 10.44 (s, 1H), 8.56 (s, 1H), 8.15 (d, J=6.5 Hz, 1H), 7.37 (t, (d, J=9.0 Hz, 2H), 7.95 (d, J=6.5 Hz, 1H), 7.75 (d, J=9.0 Hz, 2H), 7.46 (t, J=6.5 Hz, 1H), 7.37 (t, J=6.5 Hz, 1H), 7.20 (s, 1H), 2.03 (s, 3H). $^{13}$C NMR (74.8 Hz, DMSO-d) δ 172.5, 172.3, 169.3, 145.2, 136.5, 133.8, 129.2, 128.7, 125.9, 124.5, 122.8, 121.9, 121.6, 121.5, 119.0, 113.3, 110.8, 24.1.

EXAMPLE 95

Synthesis of 3-(N-(2-nitrobenzenesulfonyl)indol-3-yl)-1H-pyrrole-2,5-dione

Compound 92 (52 mg, 0.25 mmol), triethylamine (52 μL, 0.375 mmol), DMAP (10 mg), and 2-nitrobenzenesulfonyl chloride (56 mg, 0.25 mmol) were refluxed in THF (5 mL) for 48 hours. Standard aqueous workup and purification by silica gel chromatography, eluting with 2:1 petroleum ether/ethyl acetate, provided compound 95 in 44% yield, as a light yellow solid. $^1$H NMR (200 MHz, DMSO-d$^6$) δ 11.15 (br s, 1H), 8.71 (s, 1H), 8.65 (s, 1H), 8.53 (d, J=8.2 Hz, 2H), 8.07 (dd, J=5.0, 7.6 Hz, 1H), 7.91 (t, J=8.0 Hz, 1H), 7.55–7.36 (m, 2H), 7.24 (s, 1H).

EXAMPLE 96

Synthesis of 3-(N-(4-nitrobenzenesulfonyl)indol-3-yl)-1H-pyrrole-2,5-dione

Compound 92 (52 mg, 0.25 mmol), triethylamine (52 μL, 0.375 mmol), DMAP (10 mg), and 2-nitrobenzenesulfonyl chloride (56 mg, 0.25 mmol) were refluxed in THF (5 mL) for 48 hours. Standard aqueous workup and purification by silica gel chromatography, eluting with 2:1 petroleum ether/ethyl acetate, provided compound 96 in 11% yield, as a light yellow solid. $^1$H NMR (200 MHz, DMSO-d$^6$) δ 11.16 (s, 1H), 8.58 (s, 1H), 8.36 (br s, 4H), 8.09 (d, J=7.0 Hz, 1H), 7.51 (t, J=7.0 Hz, 1H), 7.41 (t, J=7.0 Hz, 1H), 7.26 (s, 1H). $^{13}$C NMR (74.8 Hz, DMSO-d$^6$) δ 172.3, 172.1, 151.1, 141.1, 133.8, 130.9, 128.8, 128.7, 127.6, 126.4, 125.3, 125.0, 123.7, 121.7, 113.3, 111.9.

EXAMPLE 97

Synthesis of 3-(N-(2-thiophenesulfonyl)indol-3-yl)-1H-pyrrole-2,5-dione

Compound 92 (52 mg, 0.25 mmol), triethylamine (52 μL, 0.375 mmol), DMAP (10 mg), and 2-thiophenesulfonyl chloride (66 mg, 0.375 mmol) were refluxed in THF (5 mL) for 48 hours. Standard aqueous workup and purification by silica gel chromatography, eluting with 2:1 petroleum ether/ethyl acetate, provided compound 97 in 58% yield, as an off white solid. $^1$H NMR (200 MHz, DMSO-d$^6$) δ 11.12 (br s, 1H), 8.47 (s, 1H), 8.04–7.97 (m, 3H), 7.45 (t, J=7.5 Hz, 1H), 7.38 (t, J=7.5 Hz, 1H), 7.19–7.15 (m, 2H). $^{13}$C NMR (74.8 Hz, DMSO-d$^6$) δ 172.5, 172.3, 137.4, 136.3, 135.7 (2), 133.9, 128.8 (2), 127.7, 126.2, 125.0, 123.2, 121.7, 113.5, 111.6.

EXAMPLE 98

Synthesis of 3-(N-octanesulfonylindol-3-yl)-1H-pyrrole-2,5-dione

Compound 92 (52 mg, 0.25 mmol) was dissolved in THF (5 mL) and treated with a 1.0M THF solution of KO$^t$Bu (250 µL, 0.25 mmol). To the resulting deep red solution was added neat butanesulfonyl chloride (36 µL, 0.257 mmol) and this mixture was stirred for 16 hours. Standard aqueous workup and purification by silica gel chromatography, eluting with 3:1 petroleum ether/ethyl acetate, provided compound 98 in 10% yield, as red semi-solid.

EXAMPLE 99

Synthesis of 3-(1H-5-chloroindol-3-yl)-1H-pyrrole-2,5-dione

Compound 99 was prepared in a manner similar manner to compound 56, using 5-chloroindole (1.00 g, 6.60 mmol), oxalyl chloride (633 µL, 7.26 mmol), acetamide (1.19 g, 19.8 mmol), and a 1M solution of KO$^t$Bu (38.0 mL, 33.0 mmol). Standard workup and purification by tituration with acetone provided compound 99 as a light orange solid in 5% yield. $^1$H NMR (200 MHz, DMSO-d$^6$) δ 12.14 (br s, 1H), 10.78 (br s, 1H), 8.38 (s, 1H), 8.00 (s, 1H), 7.51 (d, J=8.6 Hz, 1H), 7.25 (d, J=1.6 Hz, 1H), 6.89 (s, 1H). MS (EI, m/z) M$^+$=246.

EXAMPLE 100

Synthesis of 3-(1H-6-chloroindol-3-yl)-1H-pyrrole-2,5-dione

Compound 100 was prepared in a manner similar manner to compound 56, using 6-chloroindole (500 mg, 3.30 mmol), oxalyl chloride (317 µL, 3.62=3 mmol), acetamide (590 mg, 9.90 mmol), and a 1M solution of KO$^t$Bu (16.5 mL, 16.5 mmol). Standard workup and purification by tituration with acetone provided compound 100 as a light orange solid in 43% yield. m.p. 280.2–282.2° C. $^1$H NMR (200 MHz, DMSO-d6) δ 12.07 (br s, 1H), 10.79 (r s, 1H), 8.37 (d, J=2.4 Hz, 1H), 7.99 (d, J=8.5 Hz, 1H), 7.56 (s, 1H), 7.18 (d, J=8.5 Hz, 1H), 6.83 (s, 1H). $^{13}$C NMR (57.3 MHz, DMSO-d$^6$) δ 173.2, 172.9, 138.9, 137.1, 131.7, 127.5, 124.3, 121.7, 121.4, 116.2, 112.2, 105.4. MS (EI, m/z) M$^+$=246.

EXAMPLE 101

Synthesis of 3-(1H-7-chloroindol-3-yl)-1H-pyrrole-2,5-dione

Compound 101 was prepared in a manner similar manner to compound 56 using 7-chloroindole (500 mg, 3.30 mmol), oxalyl chloride (317 µL, 3.62 mmol), acetamide (590 mg, 9.90 mmol), and a 1M solution of KO$^t$Bu (16.5 mL, 16.5 mmol). Standard workup and purification by tituration with acetone provided compound 101 as a light orange solid in 37% yield. m.p. 247.6–249.8° C. $^1$H NMR (200 MHz, DMSO-d$^6$) δ 3 12.39 (br s, 1H), 10.84 (br s, 1H), 8.32 (d, J=3.1 Hz, 1H), 7.98 (d, J=8.0 Hz, 1H), 7.35 (d, J=7.6 Hz, 1H), 7.20 (t, J=7.9 Hz, 1H), 6.90 (s, 1H). $^{13}$C NMR (57.3 MHz, DMSO-d$^6$) δ 171.9, 171.7, 137.5, 132.2, 130.2, 130.1, 126.2, 121.3, 121.1, 118.2, 115.7, 105.1. MS (EI, m/z) M$^+$=246.

EXAMPLE 102

Synthesis of 3-(1H-5-flouroindol-3-yl)-1H-pyrrole-2,5-dione

Compound 102 was prepared in a manner similar manner to compound 56, using 5-fluoroindole (500 mg, 3.70 mmol), oxalyl chloride (355 µL, 4.07 mmol), acetamide (655 mg, 11.1 mmol), and a 1M solution of KO$^t$Bu (18.5 mL, 18.5 mmol). Standard workup and purification by titration with acetone provided compound 102 as a light orange solid 36% yield. $^1$H NMR (200 MHz, DMSO-d$^6$) δ 12.07 (br s, 1H), 10.74 (br s, 1H), 8.40 (d, J=2.7 Hz, 1H), 7.52 (dd, J=4.8 Hz, 8.9 Hz, 1H), 7.09 (m, 1H), 6.86 (s, 1H). MS (EI,m/z) M$^+$=230.

EXAMPLE 103

Synthesis of 3-(1H-6-flouroindol-3-yl)-1H-pyrrole-2,5-dione

Compound 103 was prepared in a manner similar manner to compound 56, using 6-fluoroindole (500 mg, 3.70 mmol), oxalyl chloride (355 µL, 4.07 mmol), acetamide (655 mg, 11.1 mmol), and a 1M solution of KO$^t$Bu (18.5 mL, 18.5 mmol). Standard workup and purification by tituration with acetone provided compound 103 as a light orange solid 15% yield. m.p. 248.5–249.0° C. $^1$H NMR (200 MHz, DMSO-d$^6$) δ 12.02 (br s, 1H), 10.77 (br s, 1H), 8.33 (d, J=3.0 Hz, 1H), 7.96 (dd, J=8.9 Hz, 5,2 Hz, 1H), 7.30 (dd, J=10.4 Hz, 2.3 Hz, 1H), 7.04 (dt, J=7.3 Hz, 2.3 Hz, 1H), 6.83 (s, 1). $^{13}$C NMR (50MHz, DMSO-d$^6$) δ 173.1, 172.9, 139.0, 129.5, 121.6, 121.5, 115.8, 109.6, 109.3, 105.4, 98.9, 98.5. MS (EI,m/z) M$^+$=230.

EXAMPLE 104

Synthesis of 3-(1H-5-nitroindol-3-yl)-1H-pyrrole-2,5-dione

Compound 104 was prepared in a manner similar manner to compound 56, using 5-nitroindole (1.00 mg, 6.17 mmol), oxalyl chloride (565 µL, 6.48 mmol), acetamide (1.15 g, 19.4 mmol), and a 1M solution of KO$^t$Bu (31.00 mL, 31.0 mmol). Standard workup and purification by tituration with acetone provided compound 104 as a light orange solid 59% yield. $^1$H NMR (200 MHz, DMSO-d) δ 12.56 (br s, 1H), 10.90 (s, 1H), 8.72 (d, J=1.9 Hz, 1H), 8.44 (s, 1H), 8.08 (d, J=8.4 Hz, 1H), 7.64 (d, J=8.8 Hz, 1H), 6.93 (s, 1H). $^{13}$C NMR (50MHz, DMSO-d$^6$) δ 172.8, 172.6, 139.8, 133.7, 130.3, 124.7, 118.3, 118.1, 116.8, 113.0, 107.0, 92.4.

EXAMPLE 105

Synthesis of 3-(1-H-5-benzyioxyindol-3-yl)-1H-pyrrole-2-one-5-thione

Compound 105 was prepared in a manner similar manner to compound 56, using 5-benzyloxyindole (223 mg, 1.0 mmol), oxalyl chloride (96 µL, 1.1 mmol), thioacetamide (250 mg, 3.3 mmol), and a 1M solution of KO$^t$Bu (5.0 mL, 5.0 mmol). Standard workup and purification by tituration with acetone provided compound 105 as a red solid 19% yield. $^1$H NMR (200 MHz, DMSO-d$^6$) δ 12.07 (s, 1H), 11.93 (s, 1H), 8.38 (d, J=2.8 Hz, 1H), 7.53–7.31 (m, 7H), 7.01 (s, 1H), 6;97 (dd, J=2.0, 8.8 Hz, 1H), 5.22 (s, 2H). $^{13}$C NMR (50 MHz, DMSO-d$^6$) δ 175.1, 154.5, 137.6, 133.9, 132.2, 131.8, 128.3, 127.7, 127.6, 126.1, 122.0, 113.6, 113.5, 104.9, 104.2, 70.0.

EXAMPLE 106

Compound 106 was prepared as a by-product of the reaction described for Compound 17.

EXAMPLE 107

3-hydroxy4-(indol-3-yl)-pyrrole-2,5-dione

Indole-3-acetamide and dimethyl oxylate were dissolved in THF (10 mL) and treated with a 1.0M solution of KO$^t$Bu (3 equiv). After stirring for 1 hour the reaction mixture was diluted with water and the resulting solid filtered, washed with water and dried in vacuo, to provide a compound 108 as a deep red solid in 65%. $^1$H NMR (200 MHz, acetone-d$^6$) δ 10.67 (br s, 1H), 9.44 (br s, 1H), 8.31 (dd, J=0.8, 8.0 Hz, 1H), 8.03 (s, 1H), 7.42 (dd, J=0.8, 8.0 Hz, 1H), 7.16 (dt, J=1.1, 7.3 Hz, 1H), 7.08 (dt, J=1.1, 7.3 Hz, 1H). $^{13}$C NMR (50 MHz, acetone-d$^6$) δ 172.2, 169.1, 147.1, 137.3, 127.6, 127.4, 126.8, 123.3, 122.8, 120.4, 112.2. MS (EI, m/z) M$^+$=228.

EXAMPLE 108

3-hydroxy-4-(N-methylindol-3-yl)-pyrrole-2,5-dione

N-Methylindole-3-acetamide and dimethyl oxylate were dissolved in THF (10 mL) and treated with a 1.0M solution of KO$^t$Bu (3 equiv). After stirring for 1 hour the reaction mixture was diluted with water and the resulting solid filtered, washed with water and dried in vacuo, to provide a compound 108 as a deep red solid in 87%.

$^1$H NMR (200 MHz, DMSO-d$^6$) δ 8.90 (br s, 1H), 8.53 (d, J=8.0 Hz, 1H), 7.59 (s, 1H), 7.23 (d, J=8.2 Hz, 1H), 7.00 (dt, J=1.2, 6.9 Hz, 1H), 6.89 (dt, J=1.2, 6.9 Hz, 1H), 3.70 (s, 3H).

EXAMPLE 109

Compound 122 was prepared according to the procedure described for compound 56, using 3-(1-(4-chlorobenzyl)-5-(1-quinolinylmethyl)indolyl)-2,2-dimethylpropianoate (1 equiv), oxalyl chloride (1.1 equiv), acetamide (3 equiv) and 1.0 M KO$^t$Bu in THF (3 equiv). Standard workup and purification using silica gel chromatography, eluting with 10:1 methylene chloride/methanol, provided compound 109 as an orange solid in 55%. $^1$H NMR (200 MHz, DMSO-d$^6$) δ 10.87 (br s, 1H), 8.39 (d, J=5.6 Hz, 1H), 8.06 (d, J=5.6 Hz, 1H), 7.98 (d, J=5.6 Hz, 1H), 7.79 (d, J=5.6 Hz, 1H), 7.75 (t, J=5.6 Hz, 1H), 7.51 (t, J=5.6 Hz, 1H), 7.51 (m, 4H), 6.95 (m, 3H), 6.75 (s, 1H), 5.72 (s, 5H), 5.51 (s, 2H), 5.40 (s, 2H).

EXAMPLE 110

Compound 84 was refluxing in methylene chloride with 5 equiv of BBr$_3$ for 16 hours. Aqueous workup and purification by silica gel chromatography, eluting with 1:1 acetone/hexane, provided compound 110 in 54% yield.

EXAMPLE 111

Compound 111 was prepared according to the procedure described for compound 56, using intermediate H1, oxalyl chloride, acetamide, and 1M KotBu in THF. Purification by silica gel chromatography, eluting with 2:1 hexane/acetone, provided compound 111 in 32% yield.

EXAMPLE 112

High/Low Potassium Assay

CGNs were harvested from day 8/9 post-natal CD1 mice, plated on Poly-D-Lycine coated plates and incubated for 6 days at 37° C., with 25 μM potassium, under 5% CO$_2$. Pretreated cells were treated with drug 24 hours prior to changing the media to one containing 5 μM potassium and drug. Cells were assayed 16 hours after the final media change using cell TITER96 (Promega). IC$_{50}$ was evaluated as the concentration at which cell death was inhibited by 50%, as shown in TABLE 6.

TABLE 6

| Example | IC$_{50}$ (μM) |
| --- | --- |
| K252a | 0.30 |
| CEP 1347 | 1 |
| 24 | 10 |
| 34 | 10 |
| 42 | 3 |
| 47 | 3 |
|  | (100% inhibition at 10 (μM) |
| 48 | 3 |
| 60 | 10 |
| 77 | 10 |
| 95 | 10 |
| 96 | 10 |

The compounds formed according to this invention inhibit HK/LK apoptotic cell death in CGNs with selected compounds protecting upwards of 100% of the neurons at 10 μm drug concentrations with IC$_{50}$ values in the range of 1–10 μM. K252a and CEP 1347 displayed IC$_{50}$ values of 0.3 and 1 μM, respectively. These compounds, however, were toxic at higher doses, while the compounds tested herein displayed little or no toxicity in untreated controls.

EXAMPLE 113

β-Amyloid Aggregation Assay

CGNs were harvested from day 8/9 post-natal CD1 mice, plated on Poly-D-Lycine coated plates and incubated for 6 days at 37° C. under 5% CO$_2$. Pretreated cells were treated with drug 24 hours prior to A-β (25 μM) and drug addition. Cells were assayed 5 days after Aβ addition using cell TITER96 (Promega), as shown in TABLE 7.

TABLE 7

| Example | IC$_{50}$ (μM) |
| --- | --- |
| CEP 1347 | toxic <300 nM |
| 2 | 10 |
| 24 | 10 |
| 42 | 1 |
| 64 | 1 |
| 87 | 10 |

Linear Aβ rapidly aggregates in CGN cultures, leading to the apoptotic cell death of approximately 50% of the neurons after 5 days. Addition of selected compounds of the formula I through III saves upwards of 100% of these cells at drug concentrations of 10 μM with $IC_{50}$ values of 1–10 μM. These compounds may be added to the CGN culture 24 hours prior to linear Aβ addition or at the time of linear Aβ addition. Similar saves were observed under these two scenarios. The most active compounds displayed limited toxicity, less than 5%, in their respective in vitro controls. As observed in the HK/LK assays, CEP 1347 displayed limited protection (>10% at concentrations below 300 nM) and severe toxicity at concentrations greater than 300 nM.

EXAMPLE 114

Ceramide Killing of CGNs

CGNs were harvested from day 8/9 post-natal CD1 mice, plated on Poly-D-Lycine coated plates and incubated for 6 days at 37° C. under 5% $CO_2$. Cells were pretreated with drug 24 hours prior to ceramide (100 uM) and drug addition. Cells were assayed 16 hours after final drug treatments using cell TITER96 (Promega), as shown in TABLE 8.

TABLE 8

| | % CGN Survival at Various Concentrations | | | | | |
|---|---|---|---|---|---|---|
| Example | 10 μM | 3 μM | 1 μM | 300 nM | 100 nM | 30 nM |
| K252a | — | — | — | 0 (250 nM) | — | — |
| CEP 1347 | — | — | 1.8 | 0 (250 nM) | — | — |
| 24 | 10.7 | — | 11.4 | — | — | — |
| 42 | 18.0 | — | 20.0 | — | — | — |
| 61 | — | — | 5.1 | — | 0 | — |
| 64 | 5.1 | — | 18.0 | — | — | — |
| 87 | 9.1 | — | 0 | — | — | — |

Addition of selected compounds of the formula I through III, 24 hours prior to the addition of ceramide, to cultured CGNs provided protection against apoptosis, with 10 to 20% of the cells being saved at 1–10 μM drug concentrations.

EXAMPLE 115

Glutamate Killing of CGNs

CGNs were harvested from day 8/9 post-natal CD1 mice, plated on Poly-D-Lycine coated plates and incubated for 6 days at 37° C. under 5% $CO_2$. Cells were pretreated with drug 24 hours prior to glutamate (100 uM) and drug addition. Cells were assayed 16 hours after final drug treatments using cell TITER96 (Promega), as shown in TABLE 9.

TABLE 9

| | % CGN Survival at Various Concentrations | | | | | |
|---|---|---|---|---|---|---|
| Example | 10 μM | 3 μM | 1 μM | 300 nM | 100 nM | 30 nM |
| K252a | — | — | — | 4.3 (250 nM) | — | — |
| CEP 1347 | — | — | 7.0 | 50.0 (250 nM) | 0 | — |
| 24 | 22.3 | — | 17.0 | — | 0 | — |
| 64 | 32.5 | — | 4.0 | — | 0 | — |
| 87 | — | — | 11.5 | — | 0 | — |

Addition of selected compounds of the formula I through III, either at the time of glutamate addition or 24 hours prior to the addition of ceramide, to cultured CGNs provided protection against neuronal cell death, with up to 20% of the cells being saved at 1–10 μM drug concentrations.

EXAMPLE 116

Cisplatin Killing of CGNs

CGNs were harvested from day 8/9 post-natal CD1 mice, plated on Poly-D-Lycine coated plates and incubated for 6 days at 37° C. under 5% $CO_2$. The cells were treated with media containing drug and cisplatin (25 mg/mL). Cells were assayed 48 hours after final drug treatments using cell TITER96 (Promega), as shown in TABLE 10.

TABLE 10

| Example | $IC_{50}$ (μM) |
|---|---|
| CEP 1347 | 30% at 1 μM |
| 1 | 10 |
| 2 | 10 |
| 3 | 10 |
| 5 | 10 |
| 24 | 3 |
| 34 | 10 |
| 35 | 0.1 |
| 36 | 0.1 |
| 42 | 3 |
| 47 | 10 |
| 48 | 10 |
| 51 | 1 |
| 52 | 3 |
| 64 | 3 |

Addition of selected compounds of the formula I through III, 24 hours prior to the addition of cisplatin (25 μg/mL), to cultured CGNs protected against neuronal apoptosis. Compounds 35 and 36 displayed $IC_{50}$ of 100 nM (80% survival at 300 nM) against cisplatin induced apoptosis in CGNs. Several other compounds of the formula I through III displayed $IC_{50}$ values in the range of 3–40 mM, with upwards of 80% neuronal survival. CEP 1347 displayed limited protection (>30%) at 1 μM.

EXAMPLE 117

Cisplatin Killing of Cortical Neurons

Cortical neurons were harvested from day E18 female Sprague-Dawley rats, plated on Poly-L-Lycine coated plates and incubated for 14 days at 37° C. under 5% $CO_2$. The cells pre-treated with with media containing drug (10 μM) for 24 hours, followed by cisplatin (35 mg/mL). Cells were assayed 16–24 hours after final drug treatments using cell TITER96 (Promega), as shown in TABLE 11.

TABLE 11

| Example | % Protection at 10 μM |
|---|---|
| 35 | 11 |
| 36 | 9 |
| 51 | 23 |
| 53 | 41 |
| CEP 1347 | 32 |
| | at 0.3 μM |

Compound 52 protected cultured cortical neurons protecting 50% of the neurons at concentrations of 10 μM.

EXAMPLE 118

NGF Withdrawal Killing of SCG Neurons

SCG neurons were harvested from day 1 post natal Sprague-Dawley rats, plated on collagen coated plates and incubated for 5 days in the presence of 50 ng/mL NGF at 37° C. under 5% $CO_2$. The cells were washed with NGF free media, 4 times at 1 hour intervals, at which time drug was added. Cells were assayed 48 hours after final drug treatments using cell TITER96 (Promega), as shown in TABLE 12.

TABLE 12

| Example | $IC_{50}$ (μM) |
| --- | --- |
| 1 | 20 |
| 33 | 10 |
| 42 | 20 |
| 47 | 10 |
| 67 | 10 |
| 97 | 10 |
| 91 | 20 |
| 109 | 10 |

Compounds of the formula I through III protect SCG neurons against NGF withdrawal when applied at concentration of 10–20 μM.

EXAMPLE 119

Etoposide Killing of SHSY-5Y

SHSY-5Y cells were grown in growth media. Cells are placed at 50,000 cells per 96 well. Four days later the cells were treated with drug for 48 hours prior to etoposide (32 uM) treatment. On day 6 media was changed to that containing etoposide and drug for 4 hours, at which point the media was changed to media containing drug only. Cells are allowed to survive overnight and then assessed for viability with metabolic activity measured (WST-1-Beohringer Mannheime), as shown in TABLE 13.

TABLE 13

| | % CGN Survival at Various Concentrations | | | | | |
| --- | --- | --- | --- | --- | --- | --- |
| Example | 10 μM | 3 μM | 1 μM | 300 nM | 100 nM | 30 nM |
| K252a | — | — | 13.9 | — | — | — |
| CEP 1347 | — | — | 12.5 | — | — | — |
| 1 | 12.5 | — | 0 | — | — | — |
| 69 | — | — | 5.6 | — | — | — |
| 70 | 7.6 | — | — | — | — | — |
| 71 | 26.4 | — | — | — | — | — |
| 73 | toxic | — | — | — | — | — |
| 99 | 4.7 | — | — | — | — | — |
| 121 | — | — | 5.5 | — | — | — |

SHSY-5Y cells are members of a neuroblastoma cell line. When SHSY-5Ys were pretreated for 24 hours with selected compounds of the formula I through III, followed by etoposide, little or no protection was observed.

EXAMPLE 120

LAN5 HAIP1 Down Regulators

LAN5 cells were grown in growth media. Cells were plated at cells 50,000 per well in 96 cells per 96 wells. Five days latter drug was added and the cells were liced 24 hours latter using RLT buffer. The licate was processed for RNA extraction and RNA levels were measured on TAQUMEN, as shown in TABLE 14.

TABLE 14

| Example | Fold Induction |
| --- | --- |
| control | 1.0 |
| K252a | 0.51 |
| 56 | 0.31 |
| 57 | 0.45 |
| 58 | 0.55 |
| 59 | 0.40 |
| 60 | 0.13 |
| 61 | 0.16 |
| 62 | 0.18 |
| 63 | 0.22 |
| 70 | 0.21 |
| 87 | 0.37 |

Cancer cells became sensitized to apoptosis by the down-regulation of the IAPs. The use of small molecules for the down-regulation of the LAPs represents a novel approach to cancer chemotherapy.

Further Synthesis Routes and Examples 121 to 175

N-substituted indoyl-3-glyoxylate B121 was prepared by the alkylation of intermediate B1 with (3-bromopropoxy)-tert-butyldimethylsilane using NaH in DMF. Condensation of glyoxylate B121 and acetamide C1 using 3.0 equiv of 1.0 M potassium tert-butoxide in THF, followed by quenching the reaction with concentrated HCl afforded 121 in good yields.

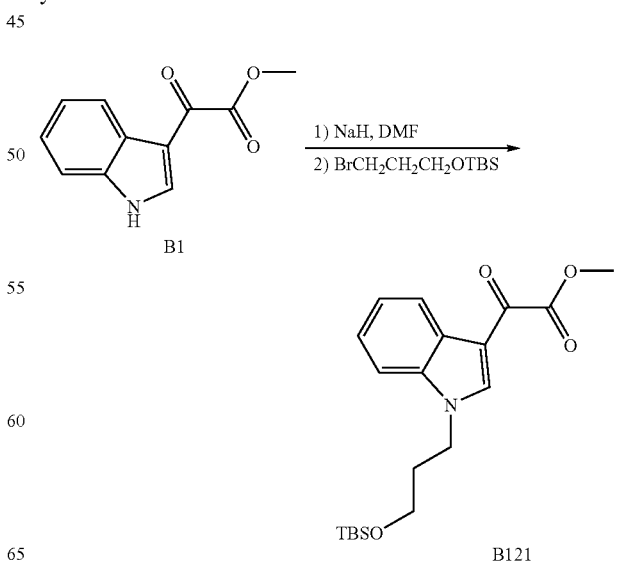

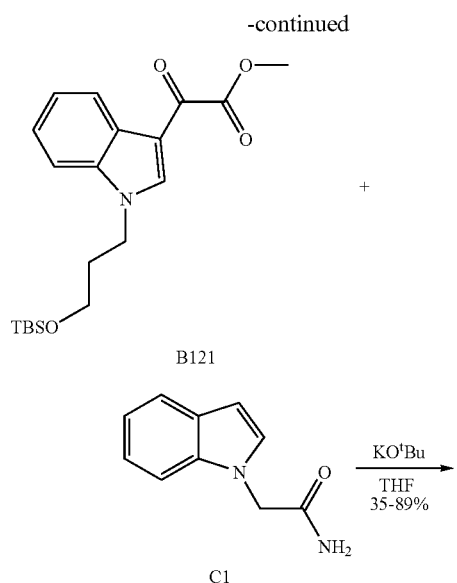
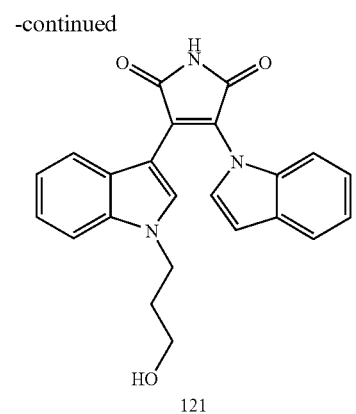
As before, cyclization using a Lewis acid such as TMSOTf provided compound 122, and oxidation with DDQ provided compound 123.
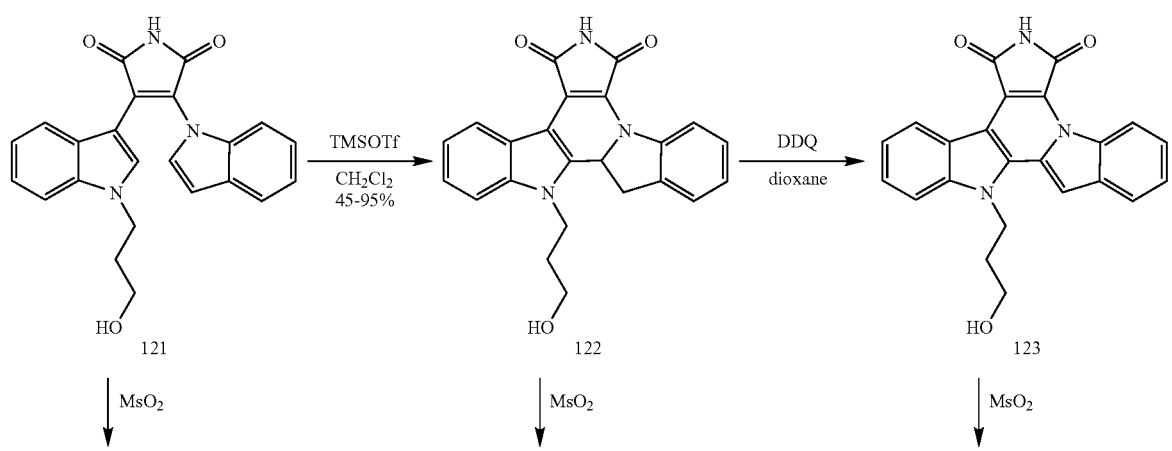
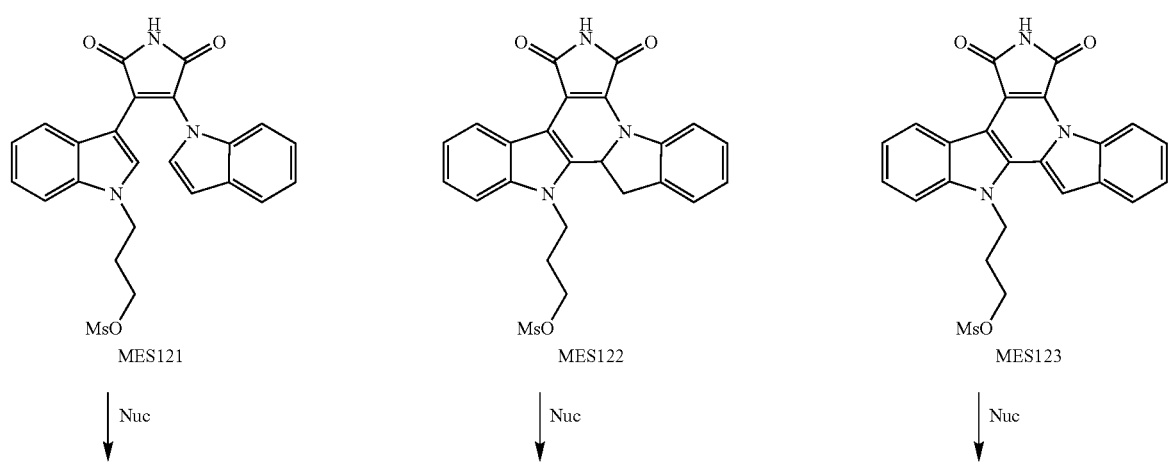

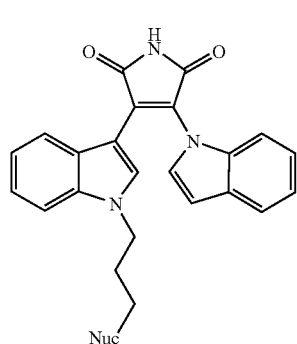

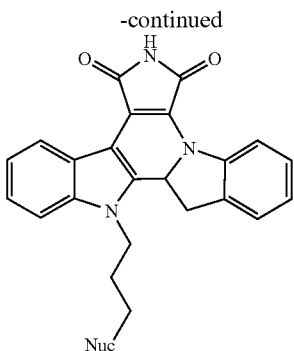

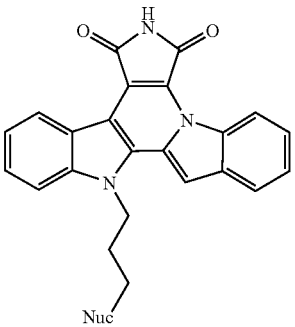

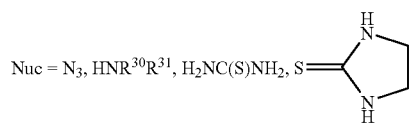

Nuc = N$_3$, HNR$^{30}$R$^{31}$, H$_2$NC(S)NH$_2$,

Treatment with methanesufonic anhydride yields the corresponding mesylates. The mesylate intermediates such as MES121, MES122, and MES123 may be displaced with a variety of nucleophiles such as, but not limited to, azide, mono- and disubstituted amines, thiourea, and 2-imidazolidone, to provide compound such as compound 133, 143, and 156.

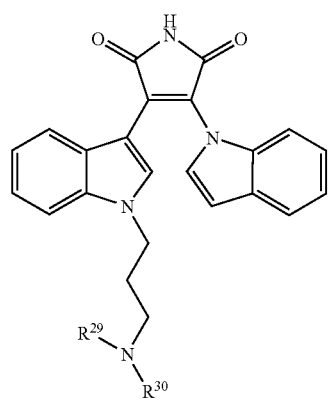

133; R$^{29}$ = R$^{30}$ = CH$_3$

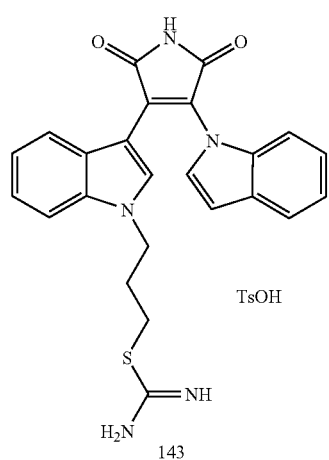

143

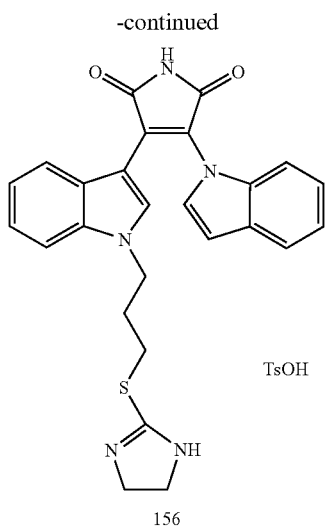

156

Staudinger reduction of the azide 161 with triphenylphosphine/water yields the primary amines 162 as shown below.

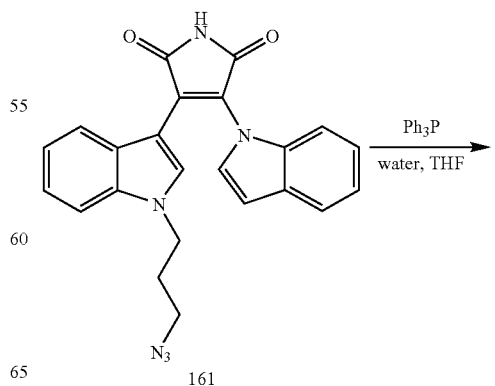

161

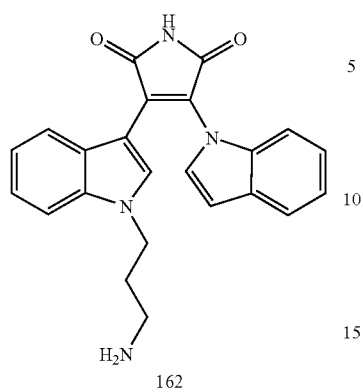

162

The following compounds were prepared, and particulars of functional groups are provided in TABLE 15.

TABLE 15

Exemplary Compounds

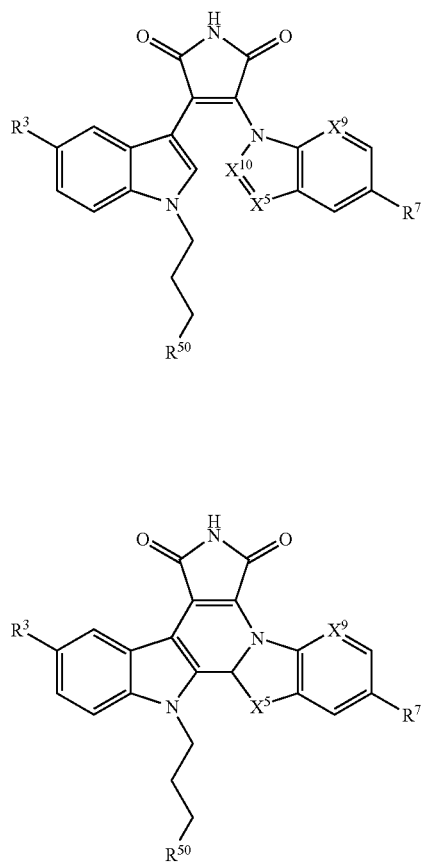

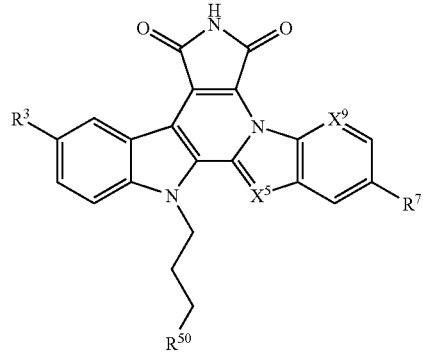

| Example | Template | $R^3$ | $R^{50}$ | $R^7$ | $X^{10}$ | $X^5$ | $X^9$ |
|---|---|---|---|---|---|---|---|
| 121 | A | H | —OH | H | CH | CH | CH |
| 122 | B | H | —OH | H | — | CH | CH |
| 123 | C | H | —OH | H | — | CH | CH |
| 124 | A | BnO | —OH | H | CH | CH | CH |
| 125 | A | H | —OH | H | CH | CMe | CH |
| 126 | A | H | —OH | BnO | CH | CH | CH |
| 127 | A | H | —OH | H | CMe | CH | CH |
| 128 | A | H | —OH | H | CH | N | CH |
| 129 | A | BnO | —OH | H | CH | CMe | CH |
| 130 | A | H | —OH | H | CH | CH | N |
| 131 | A | BnO | —OH | H | CMe | CN | CH |
| 132 | A | H | —OH | F | CH | CH | CH |
| 133 | A | H | —N(CH₃)₂ | H | CH | CH | CH |
| 134 | B | H | —N(CH₃)₂ | H | — | CH | CH |
| 135 | C | H | —N(CH₃)₂ | H | — | CH | CH |
| 136 | A | BnO | —N(CH₃)₂ | H | CH | CH | CH |
| 137 | A | H | —N(CH₃)₂ | H | CH | CMe | CH |
| 138 | A | H | —N(CH₃)₂ | BnO | CH | CH | CH |
| 139 | A | H | —N(CH₃)₂ | H | CMe | CH | CH |
| 140 | A | H | —N(CH₃)₂ | H | CH | N | CH |
| 141 | A | BnO | —N(CH₃)₂ | H | CH | CMe | CH |
| 142 | A | H | —N(CH₃)₂ | H | CH | CH | N |
| 143 | A | H | —SC(N=H)NH₂ | H | CH | CH | CH |
| 144 | B | H | —SC(N=H)NH₂ | H | — | CH | CH |
| 145 | C | H | —SC(N=H)NH₂ | H | — | CH | CH |
| 146 | A | H | —SC(N=H)NH₂ | H | CH | CMe | CH |
| 147 | A | H | —SC(N=H)NH₂ | BnO | CH | CH | CH |
| 148 | A | BnO | —SC(N=H)NH₂ | H | CH | CH | CH |
| 149 | A | BnO | —SC(N=H)NH₂ | H | CH | CMe | CH |
| 150 | A | BnO | —SC(N=H)NH₂ | H | CMe | CH | CH |
| 151 | A | H | —SC(N=H)NH₂ | H | CMe | CH | CH |
| 152 | A | H | —SC(N=H)NH₂ | H | CH | CH | N |
| 153 | A | MeO | —SC(N=H)NH₂ | H | CH | CH | CH |
| 154 | A | F | —SC(N=H)NH₂ | H | CH | CH | CH |
| 155 | A | H | —SC(N=H)NH₂ | F | CH | CH | CH |
| 156 | A | H | —Z | H | CH | CH | CH |
| 157 | B | H | —Z | H | — | CH | CH |
| 158 | C | H | —Z | H | — | CH | CH |
| 159 | A | H | —SC(N=H)NH₂ | H | CH₂ | CH₂ | CH |
| 160 | A | OCH₂SPh | —SC(N=H)NH₂ | H | CH | CH | CH |
| 161 | A | H | —N₃ | H | H | H | H |
| 162 | A | H | —NH₂ | H | H | H | H |

Z=

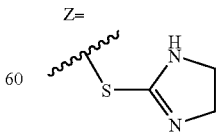

The dimethlyamino compounds were submitted as the free base, whereas the thioamidino and Z compounds were submitted as the methanesulfonic acid salts.

The introduction of a 3-hydroxypropyl moiety at the C3 position of the right hand "reverse-indole" was accomplished in the following manner. Methyl 3-indolepropionate was reduced with DIBAL to the corresponding alcohol, silylated with TBDMSCl and converted to acetamide C163 in the usual manner with NaH and iodoacetamide.

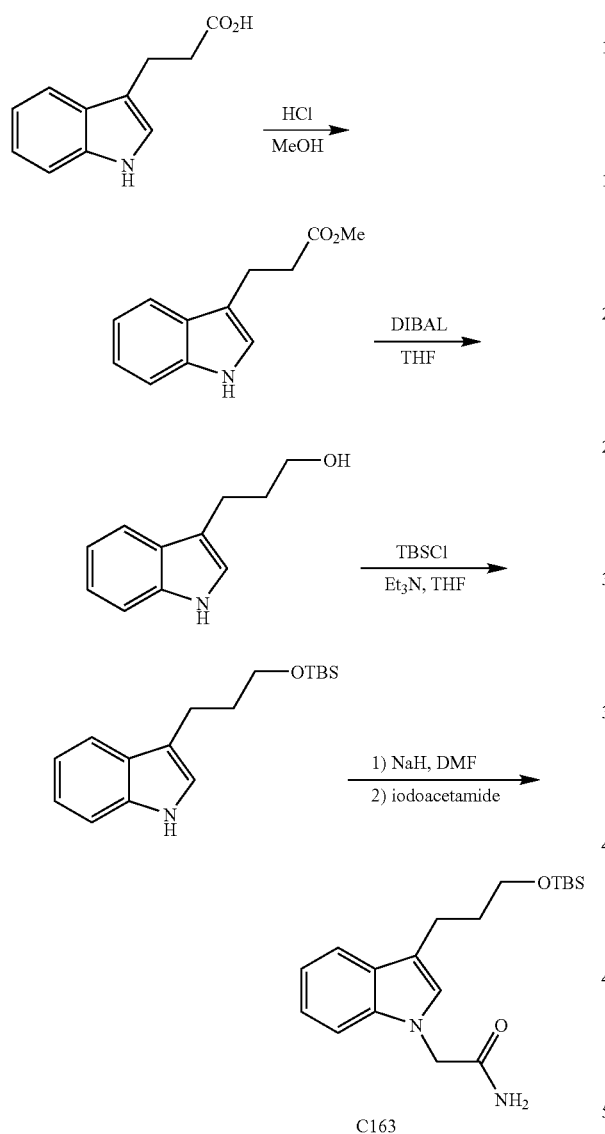

Base mediated cyclization of B1 and C163 using KO$^t$Bu in THF provided compound 163.

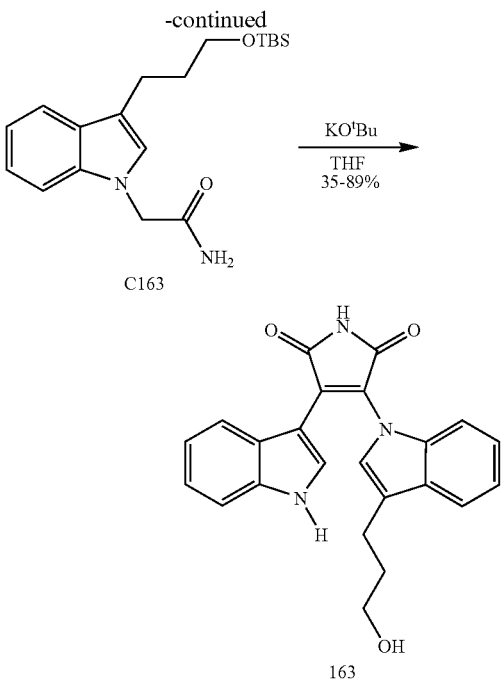

As before, functionalization of compounds 163 and 164 with methanesulfonic anhydride provided intemediates MES163 and MES164. Displacement of the mesylate with various nucleophiles yields a variety of substited derivatives.

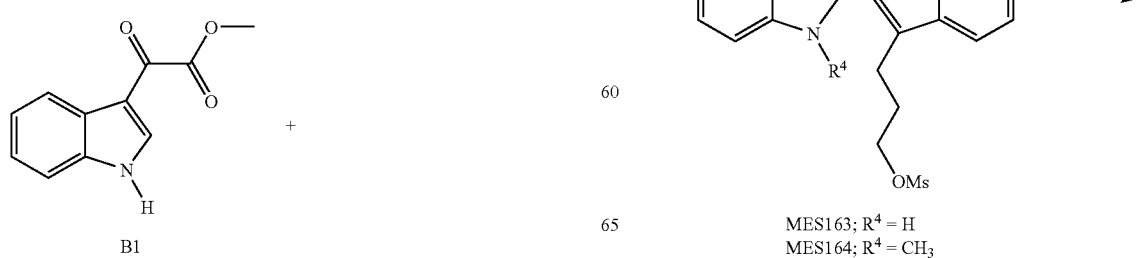

-continued

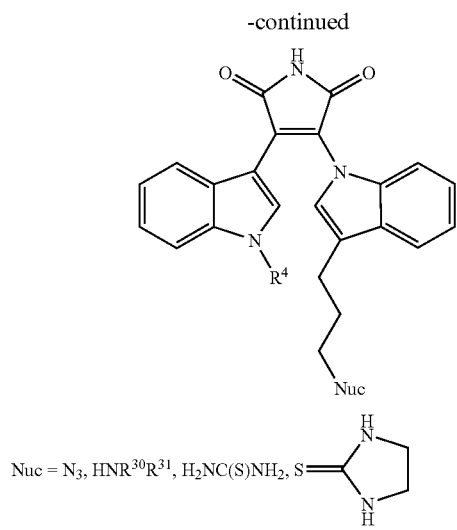

Nuc = N₃, HNR³⁰R³¹, H₂NC(S)NH₂, S–[imidazolidine-2-thione]

These compounds are summarized below, and examples are provided in TABLE 16.

TABLE 16

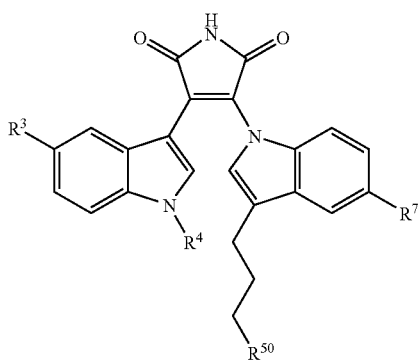

Exemplary Compounds

| Example | $R^3$ | $R^{50}$ | $R^7$ | $R^4$ |
|---|---|---|---|---|
| 163 | H | OH | H | H |
| 164 | H | OH | H | Me |
| 165 | BnO | OH | H | H |
| 166 | H | SC(N=H)NH₂ | H | H |
| 167 | H | SC(N=H)NH₂ | H | Me |
| 168 | BnO | SC(N=H)NH₂ | H | Me |
| 169 | H | N(CH₃)₂ | H | Me |
| 170 | H | Z | H | Me |
| 171 | H | N₃ | H | Me |
| 172 | H | NH₂ | H | Me |

The dimethlyamino compounds were submitted as the free base, whereas the thioamidino and Z compounds were submitted as the methanesulfonic acid salts.

The lactam derivative of compound 122 was prepared as follows. Silylation of compound 122 with TBDPSCl was followed by carbonyl reduction with NaBH₄ to provide a 4:1 mixture of isomers 174 and 175. Compound 174 was further reduced with PhSeH/TsOH and deprotected with HCl to provide compound 176.

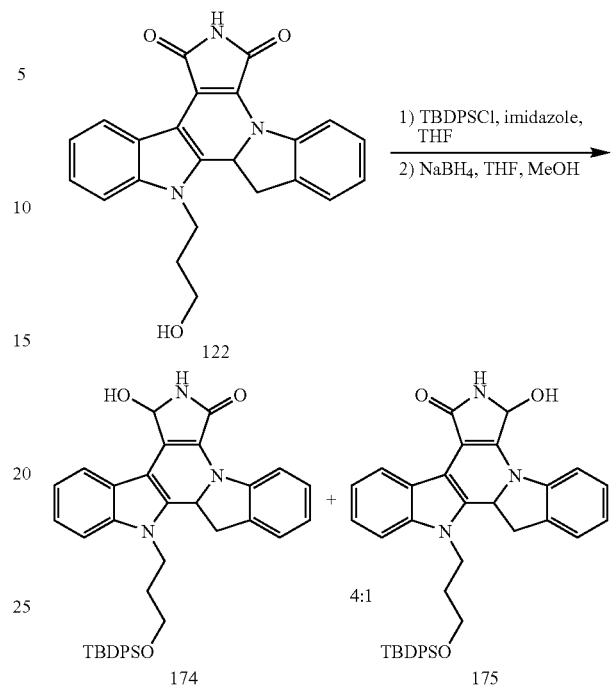

Anti-Cancer Activity

Select compounds were tested for their ability to kill various cancer cell lines. Additionally, we investigated the ability of these compounds to sensitize cancer cell lines to apoptosis in the presence of death ligands.

Prostate cancer is often resistant to traditional chemotherapies. DU145 is representative prostated cancer cell line. DU145cells were cultured in the presence of various concentrations of compound 136. As seen from TABLE 17 and FIG. 1, compound 136 kills 100% of the cells at 10 μM, after 7 days, with an $IC_{50}$ between 5 and 10 μM.

TABLE 17

Killing of DU145 prostate cancer cells with compound 136

| Conc. | % Survival | Std error |
|---|---|---|
| 40 um | 1.17 | 0.3226 |
| 20 um | −1.00 | 0.2725 |

TABLE 17-continued

Killing of DU145 prostate cancer cells with compound 136

| Conc. | | % Survival | Std error |
|---|---|---|---|
| 10 | um | −1.64 | 0.2684 |
| 5 | um | 66.75 | 0.7606 |
| 2.5 | um | 81.81 | 3.9807 |
| 1.25 | um | 99.61 | 2.7063 |
| 0.625 | um | 97.00 | 3.6379 |
| 0.312 | um | 102.71 | 1.7201 |

One mechanism of cellular apoptosis is regulated through extra-cellular ligand/receptor interactions. The death receptors of the tumor necrosis factor receptor (TNFR) family include TNFR1, FAS (CD95), DR3/WSL, and the TRAIL/APO-2L receptors (TRAIL-R1/DR1, TRAIL-R2/DR5). The binding of the death receptors by their respective ligands, TNF or lymphotoxin, Fas-ligand/Fas-L, DR3 or TRAIL/APO-2L, respectively, signals for the activation of their respective apoptotic mechanisms. Several cancer cell lines have become resistant to TNFR related apoptosis.

Jurkats are a T-cell derived lymphoma cell line which expresses both FAS receptor and Fas-L. These cells, however, are only mildly sensitive to Fas-L/anti-Fas induced apoptosis. Select compounds were tested for their ability to kill Jurkats. Additionally, we investigated the ability of select compounds to sensitize the Jurkats to anti-Fas mediated apoptosis.

Figure 2:
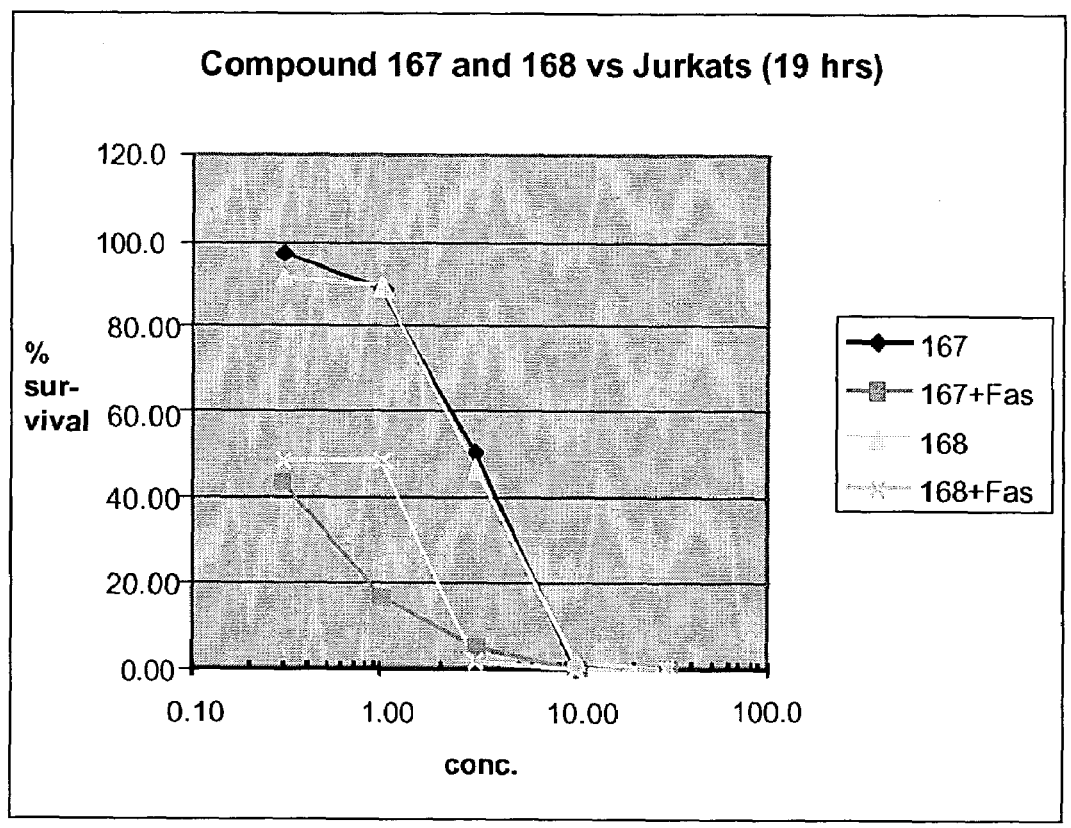
FIG. 2 depicts the killing of Jurkats with compounds 167 and 168 (described in Examples 167 and 168) with and without anti-Fas over 19 hours. Survival is plotted against concentration.

As shown in TABLE 18, select compounds of this class kill Jurkats at concentrations of 3–10 μM. anti-Fas (5 ng/mL) kills 48% of the cells after 19 hours. When cultured in the pressure of compound and anti-Fas (5 ng/mL) increased levels of apoptosis were observed at lower compound concentrations. This 2–3 fold shift in the dose response represents a synergistic effect of compound and anti-Fas, suggesting that compound may be augmenting the FAS mediated death pathway. FIG. 2 depicts the killing of cultured Jurkats with compounds 167 and 168 (+/−anti-Fas), and firther data are provided in TABLE 18.

TABLE 18

Killing of cultured Jurkats with and without anti-Fas

| | | Survival % | |
|---|---|---|---|
| Example | Dose | Without Anti-Fas | With Anti-Fas |
| 145 | 10 | 11 | — |
| | 3 | 92.44 | 34.9 |
| 146 | 10 | 0 | — |
| | 3 | >90 | 19.7 |
| 147 | 10 | 0 | — |
| | 3 | >90 | 19.7 |
| 148 | 10 | 0 | 19.7 |
| | 3 | >90 | |
| 149 | 10 | 0 | — |
| | 3 | >90 | 2.00 |
| 150 | 10 | 0 | — |
| | 3 | >90 | 4.49 |
| 159 | 10 | 17.38 | — |
| | 3 | >90 | 9.48 |
| 167 | 30 | 0 | 0 |
| | 10 | 0 | 0 |
| | 3 | 50.3 | 4.9 |
| | 1 | 88.3 | 16.7 |
| | 0.3 | 97.7 | 43.3 |
| 168 | 30 | 0 | 0 |
| | 10 | 1.2 | 0 |
| | 3 | 46.1 | 1 |
| | 1 | 89.3 | 48.6 |
| | 0.3 | 90.7 | 49.0 |

Neurite Extension Induced by Compounds 27 and 176

Figure 3:
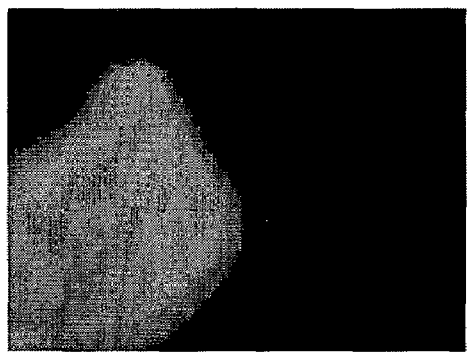
FIG. 3 depicts the neuritic enxtensions induced by compound 27 (3 μM) in rat spinal cord ex-plants.
Figure 3:
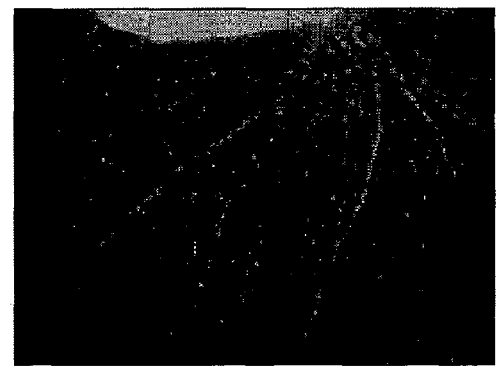

The inability of neurites to regenerate or overcome stimuli which inhibit or prevent the formation of normal neuritic extensions and connections is characteristic of the conditions found in spinal cord and related injuries, AD and the like. Select compounds of this invention promote the formation of neuritic extension in spinal cord ex-plants which have been cultured on growth inhibitory substrates. For example, compounds 27 and 176 both induce the formation of neuritic extensions from rat spinal cord ex-plants at concentrations of 3 μM (see FIG. 3).

Compounds of this class may be useful in the treatment of spinal cord injury or related diseases where neurons have lost the ability to overcome stimuli which prevent the formation of neuritic extensions and connections.

Experimental Procedures

EXAMPLE 121

Step1

Intermediate B1 (5.24 g, 25.9 mmol) was added to a suspension of NaH (1.13 g, 28.39 mmol) in DMF (100 mL), cooled to 0° C. After 1 h (3-bromopropoxy)-tert-butyldimetylsilane (6.40 g, 26.0 mmol) was added and the resultant mixture was stirred for 12 h at RT. A saturated aqueous solution of ammonium chloride and ethyl acetate were added, the organic layer was separated, washed with brine, dried over $MgSO_4$, filtered, and concentrated under reduced pressure. Purification by silica gel chromatography, eluting with 1:1 ethyl acetate/hexane, afforded intermediate B121 as a yellow solid.

Step2

Intermediates B121 (5.24 g, 13.97 mmol) and intermediate C1 (1.21 g, 6.98 mmol) were dissolved in THF (100 mL) and treated with a 1.0M THF solution of $^t$BuOK (21.0 mL, 21.0 mmol). The resulting suspension was stirred for 12 h at RT. The reaction was quenched by the addition of concentrated HCl (5 mL) and diluted with ethyl acetate. Water was added and the organic layer was separated and washed with aqueous $NaHCO_3$ and brine, dried over $MgSO_4$, filtered, and concentrated under reduced pressure. Purification by silica gel chromatography, eluting with 1:1 ethyl acetate/hexane, afforded compound 121 as an orange solid. $^1$H NMR (200MHz, DMSO-d$^6$) δ 8.06 (s, 1H), 7.53–7.56 (m, 2H), 7.41 (d, J=8.3 Hz, 1H), 6.73–6.98 (m, 5H), 6.49 (t, J=7.6 Hz, 1H), 6.02 (d, J=8.0 Hz, 1H), 4.66 (t, J=4.9 Hz, 1H), 4.31 (t, J=6.6 Hz, 2H), 3.36 (J=5.6 Hz, 2H), 1.91–1.83 (m, 2H).

Compound 122 to 132 were prepared as per compound 121 using the corresponding intermediates B and C.

EXAMPLE 124

$^1$H NMR (200 MHz, DMSO-d6) δ 8.11 (s, 1H), 7.57 (d, J=8.0 Hz, 1H), 7.47 (d, J=2.0 Hz, 1H), 7.35–7.26 (m, 4H), 7.17–7.10 (m, 3H), 7.05–6.92 (m, 2H), 6.72 (J=4.0 Hz, 1H), 6.64 (d, J=8.0 Hz, 1H), 5.55 (s, 1H), 4.65 (t, J=4.0 Hz, 1H), 4.29 (t, J=6.0 Hz, 2H), 4.01 (s, 2H), 3.38–3.31 (m, 2H), 1.87 (t, J=6.0 Hz, 1H); $^{13}$C NMR (50 MHz, DMSO-d$^6$) δ 195.4, 193.6, 177.6, 161.4, 160.4, 158.8, 155.5, 153.6, 152.7, 152.0, 151.7, 151.1, 149.5, 146.6, 145.3, 144.9, 137.7, 136.4, 135.7, 129.3, 127.4, 127.1, 93.2, 81.9, 67.6, 57.0.

EXAMPLE 125

$^1$H NMR (200 MHz, DMSO-d$^6$) δ 7.99 (s, 1H), 7.49–7.34 (m, 3H), 6.99–6.92 (m, 2H), 6.85–6.75 (m, 2H), 6.51 (t, J=8.0 Hz, 1H), 6.12 (d, J=8.0 Hz, 1H), 4.64 (t, J=6.0 Hz, 1H), 4.30 (t, J=6.0 Hz, 1H), 3.38–3.30 (m, 2H), 2.28 (s, 3H), 1.85(t, J=6.0 Hz, 2H); $^{13}$C NMR (50 MHz, DMSO-d$^6$) δ 195.4, 193.7, 160.3, 160.1, 157.8, 153.2, 151.0, 150.4, 150.1, 148.9, 146.5, 146.4, 144.7, 144.5, 143.1, 138.2, 136.2, 134.7, 81.9, 67.3, 56.9, 33.7.

EXAMPLE 126

$^1$H NMR (200 MHz, DMSO-d$^6$) δ 8.01 (s, 1H), 7.49–7.24 (m, 8H), 7.12–6.79 (m, 3H), 6.64–6.49 (m, 2H), 6.08 (d, J=8.0 Hz, 1H), 4.99 (s, 2H), 4.64 (t, J=6.0 Hz, 1H), 4.30 (t, J=8.0 Hz, 1H), 3.37–3.30 (m, 2H), 1.92–1.85 (m, 2H). $^{13}$C NMR (50 MHz, DMSO-d$^6$) δ 195.3, 193.6, 177.8, 161.8, 160.2, 158.1, 155.0, 153.7, 153.2, 152.7, 152.0, 150.8, 150.3, 146.6, 144.8, 144.4, 136.9, 136.6, 134.8, 129.5, 128.5, 128.3, 127.3, 94.1, 81.9, 67.3, 56.9.

EXAMPLE 127

$^1$H NMR (200 MHz, DMSO-d$^6$) δ 8.21 (s, 1H), 7.46–7.41 (m, 2H), 7.02–6.85 (m, 4H), 6.54–6.45 (m, 2H), 5.92 (d, J=8.0 Hz, 1H), 4.63 (t, J=6.0 Hz, 1H), 4.30 (t, J=8.0 Hz, 2H), 3.36–3.27 (m, 2H), 2.21 (s, 3H), 1.90–1.79 (m, 2H); $^{13}$C NMR (50 MHz, DMSO-d$^6$) δ 195.8, 194.4, 162.8, 162.3, 161.3, 160.1, 156.6, 153.4, 150.7, 148.3, 147.6, 146.3, 146.1, 145.5, 145.3, 144.6, 135.9, 135.7, 128.7, 127.9, 82.5, 68.1, 57.5, 37.6.

EXAMPLE 128

1H NMR (200 MHz, DMSO-d$^6$) δ 8.39 (s, 1H), 8.11 (s, 1H), 7.67 (d, J=8.0 Hz, 1H), 7.46 (d, J=8.0 Hz, 1H), 7.20–7.10 (m, 1H), 7.04–6.98 (m, 3H), 6.54 (t, J=8.0 Hz, 1H), 6.06 (d, J=8.0 Hz, 1H), 4.64 (t, J=6.0 Hz, 1H), 4.32 (t, J=6.0 Hz, 2H), 3.37–3.30 (m, 2H), 1.90–1.86 (m, 2H); $^{13}$C NMR (50 MHz, DMSO-d$^6$) δ 195.7, 193.9, 168.9, 167.7, 161.1, 159.7, 158.2, 152.7, 150.6, 148.3, 147.8, 147.6, 145.8, 144.8, 144.7, 136.9, 135.8, 127.6, 82.6, 68.2, 57.6.

EXAMPLE 129

$^1$H NMR (200 MHz, DMSO-d$^6$) δ 8.10 (s, 1H), 7.54–7.28 (m, 6H), 7.19–7.14 (m, 2H), 7.03–6.85 (m, 3H), 6.60 (dd, J=8.0, 2.0 Hz, 1H), 5.57 (d, J=2.0 Hz, 1H), 4.64 (t, J=4.0 Hz, 1H), 4.28 (t, J=6.0 Hz, 2H), 4.06 (s, 2H), 3.40–3.30 (m, 2H), 2.21 (d, J=2.0 Hz, 3H), 1.87 (t, J=6.0 Hz, 1H).

EXAMPLE 130

$^1$H NMR (200 MHz, DMSO-d$^6$) δ 8.15 (s, 1H), 7.98 (d, J=8.0 Hz, 1H), 7.93 (d, J=4.0 Hz, 1H), 7.63 (d, J=4.0 Hz, 1H), 7.40 (d, J=8.0 Hz, 1H), 7.05–6.92 (m, 2H), 6.74 (d, J=4.0 Hz, 1H), 6.45 (t, J=8.0 Hz, 1H), 5.86 (d, J=8.0 Hz, 1H), 4.64 (t, J=2.0 Hz, 1H), 4.29 (t, J=6.0 Hz, 2H), 3.35–3.31 (m, 2H), 1.96–1.81 (m, 2H); $^{13}$C NMR (50 MHz, DMSO-d$^6$) δ 196.0, 194.2, 173.2, 168.3, 161.2, 159.5, 154.5, 154.1, 150.9, 149.2, 147.3, 145.6, 145.4, 144.9, 142.0, 135.6, 128.7, 127.9, 82.6, 68.1, 57.6.

EXAMPLE 131

$^1$H NMR (200 MHz, DMSO-d$^6$) δ 8.24 (s, 1H), 7.47–7.13 (m, 7H), 7.01–6.97 (m, 3H), 6.68 (dd, J=8.0, 2.0 Hz, 1H), 6.43 (s, 1H), 5.55 (d, J=2.0 Hz, 1H), 4.62 (t, J=6.0 Hz, 1H), 4.29 (t, J=8.0 Hz, 2H), 3.97 (d, J=10.0 Hz, 1H), 3.85 (d, J=10.0 Hz, 1H), 3.37–3.29 (m, 2H), 2.11 (s, 3H), 1.96–1.81 (m, 2H).

EXAMPLE 132

$^1$H NMR (200 MHz, DMSO-d$^6$) δ 8.06 (s, 1H), 7.60 (d, J=2.40 Hz, 1H), 7.41 (d, J=8.0 Hz, 1H), 7.31 (dd, J=9.6, 2.4 Hz, 1H), 7.00–6.86 (m, 2H), 6.72–6.48 (m, 2H), 6.50 (t, J=8.0 Hz, 1H), 5.97 (d, J=8.0 Hz, 1H), 4.63 (t, J=4.0 Hz, 1H), 4.31 (t, J=6.0 Hz, 2H), 1.36–3.29 (m, 2H), 1.96–1.83 (m, 2H). $^{13}$C NMR (50 MHz, DMSO-d$^6$) δ 195.9, 194.3, 161.1, 159.1, 157.2, 155.7, 153.9, 153.7, 150.9, 147.4, 145.6, 144.9, 138.6, 135.1, 135.3, 134.7, 130.8, 130.4, 130.2, 127.9, 82.7, 68.0, 57.6.

EXAMPLE 133

Step one:

A solution of compound 121 (250 mg, 0.65 mmol) in THF (10 mL) was reacted with pyridine (157 µL, 1.94 mmol) and methanesulfonic anhydride (136 mg, 0.78 mmol) and stirred for 12 h at RT. Saturated aqueous ammonium chloride was added, the organic layer was separated, the aqueous phase was extracted with ethyl acetate, the combined organic extracts were washed with brine, dried over MgSO$_4$, filtered, and concentrated under reduced pressure. Purification by flash chromatography (silica gel, ethyl acetate) afforded the intermediate MES121 as an orange solid.

Step two:

Dimethylamine (2.8 mL, 5.6 mmol, 2.0 M in THF) was added to a solution of intermediate MES 121 (150 mg, 0.32 mmol) in THF (5 mL) and the reaction was stirred for 4 days at RT. Saturated aqueous ammonium chloride (20 mL) and ethyl acetate were added, the layers were separated, the aqueous layer-was extracted with ethyl acetate, the combined organic extracts were washed with brine, dried over MgSO$_4$, filtered, and concentrated under reduced pressure. Purification by flash chromatography (silica gel, ethylacetate) afforded the expected compound as an orange solid.

$^1$H NMR (200 MHz, DMSO-d$^6$) δ 8.03 (s, 1H), 7.57–7.52 (m, 2H), 7.41 (d, J=8.3 Hz, 1H), 6.99–6.73 (m, 5H), 6.52–6.47 (m, 1H), 6.04 (d, J=8.1 Hz, 1H), 4.28 (t, J=6.5 Hz, 2H), 2.11 (s, 6H), 2.07 (t, J=6.5 Hz, 2H), 1.88–1.79 (m, 2H).

Compound 134 to 142 were prepared as per compound 133 using the corresponding alcohol.

EXAMPLE 134

¹H NMR (200 MHz, DMSO-d⁶) δ 7.99 (s, 1H), 7.53 (d, J=7.7 Hz, 1H), 7.26–7.15 (m, 3H), 7.01–6.95 (m, 1H), 6.80–6.74 (m, 2H), 5.08 (d, J=10.3 Hz, 1H), 4.29 (t, J=6.5 Hz, 2H), 3.90 (d, J=16.4 Hz, 1H), 3.62 (dd, J=16.4,10.3 Hz, 1H), 2.10 (s, 6H), 2.14–2.08 (m, 2H). 1.88–1.81 (m, 2H).

EXAMPLE 135

¹H NMR (200 MHz, DMSO-d⁶) δ 8.06 (s, 1H), 7.65 (d, J=7.4 Hz, 1H), 7.53–7.33 (m, 4H), 7.25–7.17 (m, 1H), 7.09–7.03 (m, 2H), 4.26 (t, J=6.6 Hz, 2H), 2.10 (s, 6H), 2.12–2.05 (m, 2H), 1.91–1.80 (m, 2H); ¹³C NMR (50 MHz, DMSO-d⁶) δ 194.8, 192.5, 162.8, 162.3, 161.0, 154.1, 153.9, 151.5, 149.3, 149.1, 148.0, 146.8, 146.1, 144.1, 142.0, 140.1, 134.1, 133.9, 128.5, 79.9, 69.0, 68.1, 51.9.

EXAMPLE 136

¹H NMR (200 MHz, DMSO-d⁶) δ 8.10 (s, 1H), 7.57 (d, J=4.0 Hz, 1H), 7.49 (d, J=4.0 Hz, 1H), 7.37–7.27 (m, 2H), 7.17–6.93 (m, 3H), 6.72 (d, J=2.0 Hz, 1H), 6.63 (d, J=8.0 Hz, 1H), 5.56 (s, 1H), 4.30–4.20 (m, 2H), 4.05 (s, 2H), 2.14 (s, 6H), 2.13–2.02 (m, 2H), 1.85–1.75 (m, 2H); ¹³C NMR (50 MHz, DMSO-d⁶) δ 195.7, 193.9, 161.4, 160.4, 158.8, 155.5, 153.6, 152.7, 152.0, 151.7, 151.0, 150.8, 149.7, 146.5, 145.3, 144.9, 137.7, 136.3, 135.7, 129.3, 127.4, 127.1, 93.3, 79.9, 69.4, 68.4, 51.6.

EXAMPLE 137

¹H NMR (200 Mhz, DMSO-d⁶) δ 7.95 (s, 1H), 7.49–7.34 (m, 3H), 6.99–6.91 (m, 2H), 6.81–6.72 (m, 2H), 6.51 (t, J=8.0 Hz, 1H), 6.15 (d, J=8.0 Hz, 1H), 4.25 (t, J=6.0 Hz, 2H), 2.28 (s, 3H), 2.09 (s, 3H), 2.08–2.03 (m, 2H), 1.86–1.76 (m, 2H); ¹³C NMR (50 Mhz, DMSO-d⁶) δ 195.4, 193.7, 160.3, 160.0, 157.9, 153.2, 151.1, 150.4, 150.1, 148.9, 148.7, 146.5, 146.3, 144.7, 144.5, 143.1, 138.2, 136.1, 134.7, 127.6, 79.9, 69.4, 68.1, 51.6, 33.7.

EXAMPLE 138

¹H NMR (200 MHz, DMSO-d⁶) δ 7.97 (s, 1H), 7.49–7.30 (m, 1H), 7.12 (s, 1H), 6.98 (t, J=8.0 Hz, 1H), 6.80 (d, J=10.0 Hz, 1H), 6.64–6.46 (m, 3H), 6.11 (d, J=8.0 Hz, 1H), 4.99 (s, 2H), 4.30–4.25 (m, 2H), 2.09 (s, 6H), 2.08–2.01 (m, 6H), 1.85–1.78 (m, 2H); ¹³C NMR (50 MHz, DMSO-d⁶) δ 196.1, 194.3, 178.5, 162.5, 161.0, 158.8, 155.6, 154.4, 153.9, 153.4, 152.7, 151.5, 150.9, 149.9, 147.3, 145.5, 145.1, 137.6, 137.3, 135.4, 130.2, 129.2, 128.9, 127.9.

EXAMPLE 139

¹H NMR (200 MHz, DMSO-d⁶) δ 8.16 (s, 1H), 7.45–7.41 (m, 2H), 7.03–6.81 (m, 4H), 6.55–6.45 (m, 2H), 5.97 (d, J=8.0 Hz, 1H), 4.26 (t, J=6.0 Hz, 2H), 2.21 (s, 3H), 2.08 (s, 6H), 2.08–1.99 (m, 2H), 1.96–1.85 (m, 2H); ¹³C NMR (200 MHz, DMSO-d⁶) δ 195.9, 194.4, 162.8, 162.2, 161.3, 160.2, 156.6, 153.4, 150.7, 148.5, 147.6, 146.2, 146.0, 145.5, 145.3, 144.6, 135.9, 135.6, 128.6, 127.9, 80.5, 70.0, 68.9, 52.1, 37.6.

EXAMPLE 140

¹H NMR (200 MHz, DMSO-d⁶) δ 8.41 (s, 1H), 8.08 (s, 1H), 7.67 (d, J=8.0 Hz, 1H), 7.46 (d, J=8.0 Hz, 1H), 7.16–6.96 (m, 4H), 6.54 (t, J=8.0 Hz, 1H), 6.10 (d, J=8.0 Hz, 1H), 4.28 (t, J=6.0 Hz, 1H), 2.10 (s, 6H), 2.08–2.01 (m, 2H), 1.88–1.75 (m, 2H); ¹³C NMR (50 MHz, DMSO d⁶) δ 195.6, 193.8, 168.8, 167.7, 161.2, 159.7, 158.1, 152.8, 150.6, 148.2, 147.8, 147.6, 145.8, 144.8, 136.9, 135.8, 127.5, 80.5, 70.0, 68.9, 52.2.

EXAMPLE 141

¹H NMR (200 MHz, DMSO-d⁶) δ 8.08 (s, 1H), 7.48 (d, J=8.0 Hz, 1H), 7.37-7.28 (m, 5H), 7.20–7.16 (m, 2H), 7.02–6.90 (m, 3H), 6.59 (dd, J=8.0, 2.0 Hz, 1H), 5.57 (d, J=2.0 Hz, 1H), 4.25 (t, J=8.0 Hz, 2H), 4.07 (s, 2H), 2.21 (s, 3H), 2.10 (s, 3H), 2.09–1.99 (m, 2H), 1.88–1.80 (m, 2H); ¹³C NMR (50 MHz, DMSO-d⁶) δ 196.1, 194.5, 178.1, 162.1, 159.3, 155.9, 153.7, 153.5, 152.8, 152.6, 151.5, 151.2, 150.3, 147.2, 145.5, 143.7, 138.7, 138.3, 136.8, 136.4, 127.9, 127.7, 93.8, 80.5, 70.1, 68.9, 52.3, 34.4.

EXAMPLE 142

¹H NMR (200 MHz, DMSO-d⁶) δ 8.12 (s, 1H), 7.98 (d, J=10.0 Hz, 1H), 7.91 (d, J=6.0 Hz, 1H), 7.64 (d, J=4.0 Hz; 1H), 7.40 (d, J=8.0 Hz, 1H), 7.05–6.92 (m, 2H), 6.74 (d, J=4.0 Hz, 1H), 6.45 (t, J=8.0 Hz, 1H), 5.89 (d, J=8.0 Hz, 1H), 4.25 (t, J=8.0 Hz, 1H), 2.09 (s, 6H), 2.09–2.01 (m, 2H), 1.85–1.78 (m, 2H); ¹³C NMR (DMSO d⁶) δ 196.1, 194.3, 173.2, 168.3, 161.2, 159.6, 154.5, 153.9, 150.9, 149.2, 147.3, 145.6, 145.4, 144.9, 142.0, 135.6, 128.7, 127.9, 80.5, 70.0, 68.8, 52.2.

EXAMPLE 143

Intermediate MES121 (464 mg, 1 mmol) and thiourea (114 mg, 1.5 mmol) in ethanol (10 mL) was heated to reflux for 18 h. The solvent was removed in vacuo and the residue was purified by recrystallization from ethyl acetate to provide compound 143 as an orange solid.

¹H NMR (200 MHz, D,MSO-d⁶) δ 7.95 (s, 1H), 7.47–7.53 (m, 2H), 7.39 (d, J=4.0 Hz, 1H), 7.01–6.70 (m, 5H), 6.50 (t, J=8.0 Hz, 1H), 6.06 (d, J=8.0 Hz, 1H), 4.38-4.21 (m, 2H), 3.05–2.88 (m, 2H), 2.37 (s, 3H), 2.18–1.98 (m, 2H).

Compound 144 to 155 and 159, 160 were prepared as per compound 143 using the corresponding mesylate.

EXAMPLE 144

¹H NMR (200 MHz, DMSO-d⁶) δ 9.16 (s, 3H), 8.01 (s, 1H), 7.57 (d, J=4.0 Hz, 1H), 7.27–7.19 (m, 3H), 6.98 (t, J=8.0 Hz, 1H), 6.80–6.74 (m, 2H), 5.10 (d, J=8.0 Hz, 1H), 4.42–4.25 (m, 2H), 4.01–3.82 (m, 1H), 3.55–3.45 (m, 1H), 3.05–3.03 (m, 2H), 2.32 (s, 3H), 2.18–2.02 (m, 2H).

EXAMPLE 145

¹H NMR (200 MHz, DMSO-d⁶) δ 8.11 (s, 1H), 7.70 (d, J=6.0 Hz, 1H), 7.47-7.28 (m, 4H), 7.24 (d, J=8.0 Hz, 1H), 7.08–7.05 (m, 2H), 3.17–3.03 (m, 2H), 2.32 (s, 3H), 2.18–2.10 (m, 2H).

EXAMPLE 146

¹H NMR (200 MHz, DMSO-d⁶) δ 9.07 (s, 3H), 7.94 (s, 1H), 7.49–7.33 (m, 3H), 7.02–6.93 (m, 2H), 6.81–6.76 (m,

2H), 6.54. (t, J=8.0 Hz, 1H), 6.21 (d, J=8.0 Hz, 1H), 4.38–4.22 (m, 2H), 3.10–2.98 (m, 2H), 2.34 (s, 3H), 2.27 (s, 3H), 2.10–2.02 (m, 2H).

EXAMPLE 147

$^1$H NMR (200 MHz, DMSO-d$^6$) δ 9.05 (s, 3H), 8.02 (s, 1H), 7.49–7.27 (m, 7H), 7.13 (d, J=2.0 Hz, 1H), 7.01 (t, J=8.0 Hz, 1H), 6.83 (d, J=10.0 Hz, 1H), 6.64–6.48 (m, 3H), 6.10 (d, J=10.0 Hz, 1H), 4.99 (s, 2H), 4.40–4.25 (m, 2H), 3.05 (t, J=6.0 Hz, 2H), 2.31 (s, 3H), 2.15–2.01 (m, 2H).

EXAMPLE 148

$^1$H NMR (200 MHz, DMSO-d$^6$) δ 9.05 (s, 3H), 8.10 (s, 1H), 7.57 (d, J=4.0 Hz, 1H), 7.47 (d, J=2.0 Hz, 1H), 7.38–7.27 (m, 5H), 7.15–7.12 (m, 3H), 7.06–6.91 (m, 3H), 6.72 (d, J=2.0 Hz, 1H), 6.65 (d, J=10.0 Hz, 1H), 5.58 (s, 1H), 4.38–4.28 (m, 2H), 4.02 (s, 2H), 3.07 (t, J=6.0 Hz, 2H), 2.32 (s, 3H), 2.10–2.02 (m, 2H).

EXAMPLE 149

$^1$H NMR (200 MHz, DMSO-d$^6$) δ 9.06 (s, 3H), 8.10 (s, 1H), 7.50 (d, J=8.0 Hz, 1H), 7.36–7.28 (m, 4H), 7.19–7.15 (m, 2H), 7.03–6.86 (m, 3H), 6.61 (dd, J=10.0, 2.0 Hz, 1H), 5.61 (d, J=2.0 Hz, 1H), 4.35–4.25 (m, 2H), 4.08 (s, 2H), 3.06 (t, J=6.0 Hz, 2H), 2.33 (s, 3H), 2.22 (s, 3H), 2.18–2.02 (m, 2H).

EXAMPLE 150

$^1$H NMR (200 MHz, DMSO-d$^6$) δ 9.03 (s, 3H), 8.25 (s, 1H), 7.45–7.30 (m, 5H), 7.20–7.13 (m, 3H), 7.01–6.96 (m, 3H), 6.71 (d, J=8.0 Hz, 1H), 6.44 (s, 1H), 5.58 (s, 1H), 4.36–4.30 (m, 2H), 4.00 (d, J=12.0 Hz, 1H), 3.87 (d, J=12.0 Hz, 1H), 3.09–3.02 (m, 2H), 2.31 (s, 3H), 2.12 (s, 3H), 2.12–2.02 (m, 2H).

EXAMPLE 151

$^1$H NMR (200 MHz, DMSO-d$^6$) δ 9.06 (s, 3H), 8.18 (s, 1H), 7.48–7.43 (m, 2H), 7.05–6.80 (m, 4H), 6.58–6.46 (m, 2H), 6.00 (d, J=8.0 Hz, 1H), 4.38–4.25 (m, 2H), 3.15–2.98 (m, 2H), 2.34 (s, 3H), 2.22 (s, 3H), 2.08–1.99 (m, 2H).

EXAMPLE 152

$^1$H NMR (200 MHz, DMSO-d$^6$) δ 9.03 (s, 3H), 8.15 (s, 1H), 7.63 (d, J=4.0 Hz, 1H), 7.44 (d, J=8.0 Hz, 1H), 7.04–6.97 (m, 2H), 6.74 (d, J=2.0 Hz, 1H), 6.46 (t, J=8.0 Hz, 1H), 5.90 (d, J=8.0 Hz, 1H), 4.35–4.30 (m, 2H), 3.10–3.02 (m, 2H), 2.31 (s, 3H), 2.10–2.02 (m,2H).

EXAMPLE 153

$^1$H NMR (200 MHz, DMSO-d$^6$) δ 8.07 (s, 1H), 7.55 (d, J=8.0 Hz, 1H), 7.49 (d, J=4.0 Hz, 1H), 7.33 (d, J=8.0 Hz, 1H), 7.08–6.88 (m, 4H), 6.68 (d, J=2.0 Hz, 1H), 6.56 (d, J=7.0 Hz, 1H), 5.52 (s, 1H), 4.35–4.30 (m, 2H), 3.10–3.01 (m, 2H), 2.92 (s, 2H), 2.33 (s,3H), 2.10–2.00 (m, 2H).

EXAMPLE 154

$^1$H NMR (200 MHz, DMSO-d$^6$) δ 9.03 (s, 3H), 8.05 (s, 1H), 7.54–7.44 (m, 3H), 6.96–6.76 (m, 5H), 5.68 (d, J=8.0 Hz, 1H), 4.38–4.23 (m, 2H), 3.15–2.98 (m, 2H), 2.31 (s, 3H), 2.08–1.98 (m, 2H).

EXAMPLE 155

$^1$H NMR (200 MHz, DMSO-d$^6$) δ 9.08 (s, 3H), 8.05 (s, 1H), 7.60 (d, J=4.0 Hz, 1H), 7.45 (d, J=8.0 Hz, 1H), 7.32 (d, J=8.0 Hz, 1H), 7.00–6.90 (m, 2H), 6.73-6.50 (m, 3H), 6.02 (d, J=8.0 Hz, 1H), 4.42–4.25 (m, 2H), 3.15–2.99 (m, 2H), 2.34 (s, 3H), 2.07–1.99 (m, 2H).

EXAMPLE 156

A mixture of intermediate MES 121 (464 mg, 1 mmol) and imidazolidinone (123 mg, 1.2 mmol) in ethanol (10 mL) was heated to reflux for 18 h. The solvent was removed in vacuo and the residue was purified by recrystallisation from ethyl acetate.

$^1$H NMR (200 MHz, DMSO-d$^6$) δ 8.02 (s, 1H), 7.55–7.42 (m, 3H), 7.03–6.71 (m, 5H), 6.52 (t, J=8.0 Hz, 1H), 6.08 (d, J=8.0 Hz, 1H), 4.42–4.28 (m, 2H), 3.84 (s, 4H), 3.18–3.06 (m, 2H), 2.9 (s, 3H), 2.20–2.10 (m, 2H).

Compound 157 and 158 were prepared as per compound 156 using the corresponding mesylate.

EXAMPLE 157

$^1$H NMR (200 MHz, DMSO-d$^6$) δ 8.02 (s, 1H), 7.57 (d, J=4.0 Hz, 1H), 7.27-7.19 (m, 3H), 6.98 (t, J=8.0 Hz, 1H), 6.80–6.74 (m, 2H), 5.10 (d, J=8.0 Hz, 1H), 4.44–4.25 (m, 2H), 4.01–3.85 (m, 1H), 3.82 (s, 4H), 3.75–3.65 (m, 1H), 3.10–3.03 (m, 2H), 2.2–210 (m, 2H).

EXAMPLE 158

$^1$H NMR (200 MHz, DMSO-d$^6$) δ 8.12 (s, 1H), 7.70 (d, J=8.0 Hz, 1H), 7.48-7.29 (m, 5H), 7.25 (t, J=8.0 Hz, 1H), 7.09–7.05 (m, 2H), 4.40–4.25 (m, 2H), 3.82 (s, 4H), 3.15 (t, J=6.0 Hz, 2H), 2.30 (s, 3H), 2.20–2.10 (m, 2H).

EXAMPLE 161

A mixture of intermediate MES121 (928 g, 2 mmol) and sodium azide (260 mg, 4.0 mmol) in DMF (10 mL) was heated to reflux for 3 h. Water was added and the product was isolated by filtration to provide compound 161 as an orange solid.

$^1$H NMR (200 MHz, DMSO-d$^6$) δ 8.00 (s, 1H), 7.60–7.52 (m, 2H), 7.41 (d, J=10.0 Hz, 1H), 7.00–6.72 (m, 5H), 6.51 (t, J=8.0 Hz, 1H), 6.10 (d, J=8.0 Hz, 1H), 4.31 (t, J=6.0 Hz, 1H), 3.25 (t, J=8.0 Hz, 1H), 2.00–1.92 (m, 2H); $^{13}$C NMR (50 MHz, DMSO-d$^6$) δ 195.9, 194.3, 160.9, 160.5, 158.6, 153.8, 153.3, 151.5, 150.9, 150.5, 147.4, 147.0, 145.8, 145.7, 145.1, 136.8, 135.4, 130.3, 128.3, 72.9, 68.3, 53.6.

EXAMPLE 162

To a solution of compound 161 (670 mg, 1.63 mmol) in THF (10 mL) was added triphenylphosphine (469 mg, 1.79 mmol). The resulting solution was stirred for 2 h at RT and then water was added (55 μL, 3.06 mmol). After stirring for 12 h at RT the solvent was removed in vacuo and the compound was purified by recrystallization from ethyl acetate to provide compound 162 as an orange solid $^1$H NMR (200 MHz, DMSO-d$^6$) δ 8.03 (s, 2H), 7.60–7.44 (m, 4H), 6.98–6.71 (m, 5H), 6.48 (t, J=8.0 Hz, 1H), 6.00 9d, J=8.0 Hz, 1H), 4.42–3.96 (m, 2H), 2.75-2.68 (m, 2H), 2.10–2.01 (m, 2H).

EXAMPLE 163

Step One:

3-Indolepropionic acid (5 g) was dissolved in MeOH (50 mL) and treated with conc. HCl (5 mL). The solution was stirred overnight before the solvent was removed under reduced pressure to provide methyl 3-indolepropionate in quantitative yield. Crude methyl 3-indolepropionate (4.70 g, 23.2 mmol) was dissolved in THF (50 mL), cooled to 0° C., and treated with DIBAL-H (69.5 mL, 69.5 mmol). The reaction mixture was stirred for 2 h at 0° C. and then quenched by the slow addition of a saturated aqueous solution of ammonium chloride and extracted with ethyl acetate, the combined organic extracts were washed with brine, dried over MgSO$_4$, filtered, and concentrated under reduced pressure. Purification by silica gel chromatography, eluting with 1:1 ethyl acetate/hexane, afforded the 3-(3-hydroxypropyl)indole as a yellow solid. $^1$H NMR (200 MHz, DMSO-d$^6$) δ 7.48 (d, J=8.0 Hz, 1H), 7.23 (d, J=8.0 Hz, 1H), 7.15–6.92 (m, 4H), 4.40 (t, J=6.0 Hz, 1H), 3.55 (t, J=6.0 Hz, 2H), 2.80 (t, J=8.0 Hz, 2H), 1.92–1.76 (m, 2H).

Step Two:

To a solution of 3-(3-hydroxypropyl)indole (1.75 g, 10 mmol) in dichloromethane were sequentially added imidazole (748 mg, 11 mmol) and TBSCl (1.66 g, 11 mmol). The resultant mixture was stirred for 3 h at RT. A saturated aqueous solution of NaHCO$_3$ was added, the organic layer was separated, the aqueous phase was extracted with ethyl acetate. The combined extracts were washed with brine, dried over MgSO$_4$, filtered, and concentrated under reduced pressure. Purification by silica gel chromatography, eluting with 1:4 ethyl acetate/hexane, afforded 3-(3-(tert-butyldimethylsiloxy)propyl)indole as a yellow solid. $^1$H NMR (200 MHz, DMSO-d$^6$) δ 7.45 (d, J=8.0 Hz, 1H), 7.22 (d, J=8.0 Hz, 1H), 7.15–6.92 (m, 4H), 3.65 (t, J=6.0 Hz, 2H), 2.70 (t, J=8.0 Hz, 2H), 1.92–1.76 (m, 2H), 0.86 (s, 9H), 0.01 (s, 6H).

Step Three:

3-(3-(tert-Butyldimethylsiloxy)propyl)indole (2.60 g, 8.99 mmol) was added to a cooled suspension of NaH (395 mg, 9.89 mmol) in DMF (30 mL). After stirring for 1 h at 0° C., iodoacetamide (1.83 g, 9.89 mmol) was added and the resultant mixture was stirred at RT for 12 h. The DMF was removed in vacuo and the residue dissolved in ethyl acetate, water was added, the organic phase was separated and washed with brine, dried over MgSO$_4$, filtered, and concentrated under reduced pressure. Purification by silica gel chromatography, eluting with 1:4 ethyl acetate/hexane, afforded intermediate C161 as a yellow solid. $^1$H NMR (200 MHz, DMSO-d$^6$) δ 7.48 (dd, J=8.0, 1.0 Hz, 1H), 7.26 (s, 1H), 7.24 (d, J=8.0 Hz, 1H), 7.18 (s, 1H), 7.12–6.97 (m, 3H), 4.68 (s, 2H), 3.64 (t, J=6.0 Hz, 2H), 2.69 (t, J=8.0 Hz, 2H), 1.90–1.74 (m, 2H), 0.89 (s, 9H), 0.01 (s, 6H).

Step Four:

tert-BuOK (8.6 mL, 1.0 M in 8.6 mmol) was added to a suspension of intermediate C163 (1.16 g, 5.73 mmol) and intermediate B1 (990 mg, 2.86 mmol) and the resulting mixture was stirred at RT for 12 h. The reaction was quenched by the addition of concentrated HCl (5 mL) and diluted with ethyl acetate. Water was added, the organic layer was separated and washed with aqueous NaHCO$_3$ and brine, dried over MgSO$_4$, filtered, and concentrated under reduced pressure. Purification by silica gel chromatography, eluting with 1:4 ethyl acetate/hexane, afforded compound 163 as an orange solid.

$^1$H NMR (200 MHz, DMSO-d$^6$) δ 7.98 (s, 1H), 7.51 (d, J=8.0 Hz, 1H), 7.30 (s, 1H), 7.28 (d, J=6.0 Hz, 1H), 6.96–6.79 (m, 4H), 6.44 (t, J=8.0 Hz, 1H), 6.03 (d, J=8.0 Hz, 1H), 4.44 (t, J=4.0 Hz, 1H), 3.50–3.40 (m, 2H), 2.78–2.70 (m, 2H), 1.82–1.70 (m, 2H).

EXAMPLE 164

Compound 164 was prepared as per compound 161 using methyl 3-(N-methylindole)glyoxylate in the place of intermediate B1 to provide a yellow solid.

$^1$H NMR (200 MHz, DMSO-d$^6$) δ 8.01 (s, 1H), 7.52 (d, J=7.6 Hz, 1H), 7.36-7.31 (m, 2H), 7.00–6.82 (m, 4H), 6.46 (t, J=8.0 Hz, 1H), 5.93 (d, J=8.0 Hz, 1H), 4.45 (t, J=6.0 Hz, 1H), 3.84 (s, 3H), 3.49–3.43 (m, 2H), 2.74 (t, J=6.0 Hz, 2H), 1.82–1.70 (m, 2H).

EXAMPLE 166

Step One:

A solution of compound 163 (574 mg, 1.49 mmol) in THF (10 mL) was reacted with pyridine (361 µL, 4.47 mmol) and methanesulfonic anhydride (311 mg, 1.78 mmol) and stirred for 12 h at RT. Saturated aqueous ammonium chloride was added, the organic layer was separated, the aqueous phase was extracted with ethyl acetate, the combined organic extracts were washed with brine, dried over MgSO$_4$, filtered, and concentrated under reduced pressure. Purification by flash chromatography (silica gel, ethyl acetate) afforded the intermediate MES163 as an orange solid.

$^1$H NMR (DMSO-d$^6$) δ 8.09 (s, 1H), 7.54 (d, J=8.0 Hz, 1H), 7.35 (d, J=6.0 Hz, 1H), 7.34 (s, 1H), 7.00–6.84 (m, 4H), 6.48 (t, J=6.0 Hz, 1H), 5.93 (d, J=8.0 Hz, 1H), 4.20 (t, J=6.0 Hz, 1H), 3.85 (s, 3H), 3.14 (s, 3H), 2.80 (t, J=8.0 Hz, 2H), 2.05–1.94 (m, 2H).

Intermediate MES163 (477 mg, 1 mmol) and thiourea (114 mg, 1.5 nmmol) in ethanol (10 mL) was heated to reflux for 18 h. The solvent was removed in vacuo and the residue was purified by recrystallization from ethyl acetate to provide compound 166.

$^1$H NMR (200 MHz, DMSO-d$^6$) δ 9.03 (s, 3H), 8.00 (d, J=8.0 Hz, 1H), 7.52 (d, J=8.0 Hz, 1H), 7.31 (s, 1H), 7.29 (d, J=6.0 Hz, 1H), 7.05–6.85 (m, 4H), 6.41 (t, J=6.0 Hz, 1H), 5.98 (d, J=8.0 Hz, 1H), 3.41 (s, 3H), 3.15–3.10 (m, 2H), 2.90–2.80 (m, 2H), 2.02–1.92 (m,2H).

EXAMPLE 167

Compound 167 was prepared as per compound 166 using intermediate MES164 and thiourea. $^1$H NMR (200 MHz, DMSO-d$^6$) δ 9.04 (s, 3H), 8.10 (s, 1H), 7.53 (d, J=8.0 Hz, 1H), 7.36 (d, J=8.0 Hz, 1H), 7.31 (s, 1H), 6.98–6.85 (m, 4H), 6.44 (t, J=8.0 Hz, 1H), 5.90 (d, J=8.0 Hz, 1H), 3.86 (s, 3H), 3.15–3.05 (m, 2H), 2.25–2.15 (m, 2H), 2.32 (s, 3H), 2.02–1.90 (m, 2H).

EXAMPLE 169

Dimethylamine (20 mL, 40 mmol, 2.0 M in THF) was added to a solution of intermediate MES 164 (954 mg, 2 mmol) in THF and the reaction was stirred for 4 days at RT. Saturated aqueous ammonium chloride (20 mL) and ethyl acetate were added, the layers were separated, the aqueous layer was extracted with ethyl acetate, the combined organic extracts were washed with brine, dried over MgSO4, filtered, and concentrated under reduced pressure. Purification by flash chromatography (silica gel, ethylacetate) afforded the expected compound as an orange solid.

$^1$H NMR (200 MHz, DMSO-d$^6$) δ 8.09 (s, 1H), 7.50 (d, J=6.0 Hz, 1H), 7.34 (d, J=8.0 Hz, 1H), 7.26 (s, 1H), 7.02–6.78 (m, 4H), 6.45 (t, J=8.0 Hz, 1H), 5.93 (d, J=8.0 Hz, 1H), 3.85 (s, 3H), 2.69 (t, J=8.0 Hz, 2H), 2.19 (t, J=8.0 Hz, 2H), 2.08 (s, 6H), 1.75–1.65 (m, 2H).

EXAMPLE 170

A mixture of intermediate MES 164 (477 mg, 1 mmol) and imidazolidinone (123 mg, 1.2 mmol) in ethanol (10 mL) was heated to reflux for 18 h. The solvent was removed in vacuo and the residue was purified by recrystallisation from ethyl acetate.

$^1$H NMR (200 MHz, DMSO-d$^6$) δ 8.09 (s, 1H), 7.53 (d, J=8.0 Hz, 1H), 7.38-7.29 (m, 2H), 7.03–6.82 (m, 4H), 6.44 (t, J=8.0 Hz, 1H), 5.89 (d, J=8.0 Hz, 1H), 3.84 (s, 4H), 3.42 (s, 3H), 3.20–3.10 (m, 2H), 2.85–2.72 (m, 2H), 2.30 (s, 3H), 2.08–1.84 (m, 2H).

EXAMPLE 171

A mixture of intermediate MES164 (1.30 g, 2.72 mmol) and sodium azide (354 mg, 5.45 mmol) in DMF (10 mL) was heated to reflux for 3 h. Water was added and the product was isolated by filtration to provide an orange solid.
$^1$H NMR (200 MHz, DMSO-d$^6$) 8.09 (s, 1H), 7.52 (d, J=6.0 Hz, 1H), 7.36 (d, J=8.0 Hz, 1H), 7.28 (s, 1H), 7.01-6.83 (m, 4H), 6.45 (t, J=8.0 Hz, 1H), 5.92 (d, J=8.0 Hz, 1H), 3.85 (s, 3H), 3.27 (t, J=6.0 Hz, 2H), 2.76 (t, J=6.0 Hz, 2H), 1.96–1.77 (m, 2H).

EXAMPLE 172

To a solution of compound 171 (650 mg, 1.53 mmol) in THF (10 mL) was added triphenylphosphine. The resulting solution was stirred for 2 h at RT and then water was added (55 μL, 3.06 mmol). After stirring for 12 h at RT, The solvent was removed in vacuo and the compound was purified by cristallisation in ethyl acetate to provide compound 172 as an orange solid. $^1$H NMR (200 MHz, DMSO-d$^6$) δ 8.06 (s, 1H), 7.53 (d, J=8.0 Hz, 1H), 7.34 (s, 2H), 6.98–6.83 (m, 4H), 6.50–6.43 (m, 1H), 5.88 (d, J=8.0 Hz, 1H), 3.82 (s, 3H), 2.84–2.76 (m, 4H), 1.98–1.89 (m, 2H).

EXAMPLE 174

To a solution of compound 122 (2.10 g, 5.45 mmol) in THF (30 mL) were sequentially added imidazole (371 mg, 5.45 mmol) and tert-butylchlorodiphenylsilane (1.42 mL, 5.45 mmol) and the solution was stirred for 12 h at RT. A saturated aqueous solution of ammonium chloride ant ethyl acetate were added, the aqueous layer was separated and extracted with ethyl acetate, the combined organic extracts were washed with brine, dried over MgSO$_4$ and concentrated under reduced pressure. To a solution of crude protected alcohol (3.00 g, 4.81 mmol) in chloroform (30 mL) and methanol (60 mL) cooled to 0° C. was added NaBH$_4$ (3.64 g, 96.3 mmol) and the reaction mixture was stirred for 1 h at 0° C. and then quenched by slow addition of a saturated aqueous ammonium chloride. Ethyl acetate was added, the organic layer was separated, the aqueous phase was extracted with ethyl acetate, the combined organic extracts were washed with brine, dried over MgSO$_4$, filtered, and concentrated under reduced pressure. Purification by silica gel chromatography, eluting with 2:1 ethyl acetate/hexane, afforded the major isomer, compound 174 as a yellow solid. Major isomer: $^1$H NMR (200 MHz, DMSO-d$^6$) δ 8.00 (s, 1H), 7.91 (s, 1H), 7.70 (d, J=8.0 Hz, 1H), 7.62–7.51 (m, 4H), 7.42–7.24 (m, 8H), 7.14–6.99 (m, 3H), 6.82 (t, J=6.0 Hz, 1H), 6.64 (d, J=8.0 Hz, 1H), 5.45 (d, J=9.4 Hz, 1H), 5.15 (dd, J=10.4, 5.2 Hz, 1H), 4.38-4.30 (m, 2H), 3.86 (dd, J=16.8,6.0 Hz, 1H), 3.65–3.55 (m, 3H), 2.05–1.95 (m, 2H), 1.00 (s, 9H); $^{13}$C NMR (50 MHz, DMSO-d$^6$) δ 195.8, 175.6, 169.4, 159.8, 159.4, 157.4, 157.1, 154.3, 154.1, 152.3, 151.1, 150.3, 149.1, 148.9, 145.9, 144.9, 139.2, 138.5, 134.2, 133.4, 132.5, 102.9, 90.5, 84.7, 66.6, 57.1, 53.9, 51.0, 43.0.

EXAMPLE 176

To a solution of compound 174 (1.40 g, 2.24 mmol) in dichloromethane (40 mL) were sequentially added phenylselenol (1.68 mL, 15.7 mmol) and PTSA (cat) and the reaction was stirred for 2 h at RT and concentrated under reduced pressure. Purification by silica gel chromatography, eluting with ethyl acetate, afforded the TBDP silyl ether of compound 176 as a beige solid.

$^1$H NMR (200 MHz, DMSO-d$^6$) δ 7.94 (s, 1H), 7.81 (s, 1H), 7.59–7.43 (m, 3H), 7.40–7.29 (m, 7H), 7.27 (d, J=6.0 Hz, 1H), 7.16–7.05 (m, 4H), 6.84 (t, J=6.0 Hz, 5.28 (t, J=8.0 Hz, 1H), 4.96 (d, J=16.0 Hz, 1H), 4.37–4.30 (m, 2H), 3.93–3.72 (m, 3H), 3.57–3.45 (m, 2H), 2.03–1.95 (m, 2H), 1.00 (s, 9H); $^{13}$C NMR (50 MHz, DMSO-d$^6$) δ 197.4, 174.9, 169.4, 159.9, 159.5, 157.5, 154.2, 152.3, 151.9, 149.7, 149.4, 148.4, 145.8, 145.1, 138.9, 135.7, 134.0, 133.3, 132.9, 89.9, 84.9, 69.2, 66.7, 57.0, 55.2, 51.0, 43.0.

The above silyl ether (220 mg, 0.35 mmol) was dissolved in 20 mL of 5% HCl and was stirred for 1 h at RT. NaHCO$_3$ was added, the reaction was concentrated under reduced pressure. Brine and ethyl acetate were added, the organic layer was separated dried over MgSO$_4$, filtered, and concentrated under reduced pressure. Purification by silica gel chromatography, eluting with ethyl acetate, afforded compound 176 as a beige solid.

$^1$H NMR (200 MHz, DMSO-d$^6$) δ 7.91 (s, 1H), 7.80 (s, 1H), 7.44 (d, J=8.0 Hz, 1H), 7.27 (d, J=8.0 Hz, 1H), 7.18–7.00 (m, 4H), 6.84 (t, J=6.0 Hz, 1H), 5.28 (t, J=10.2 Hz, 1H), 4.95 (d, J=17.6 Hz, 1H), 4.60 (t, J=5.2 Hz, 1H), 4.26 (t, J=6.6 Hz, 1H), 3.87 (d, J=17.6 Hz, 1H), 3.83–3.70 (m, 2H), 3.38–3.31 (m, 2H), 1.96–1.84 (m, 2H). $^{13}$C NMR (50 MHz, DMSO-d$^6$) δ 197.4, 174.9, 169.4, 159.8, 157.5, 154.2, 151.9, 149.4, 148.5, 145.8, 145.1, 138.9, 135.7, 134.2, 133.1, 132.7, 89.8, 82.1, 69.2, 66.9, 57.5, 55.1.

EXAMPLE 173

Anticancer Effectiveness on Prostate Tumor Cells

Human prostate DUI45 cells were cultured in 96 well dishes. Cells were treated with various concentrations of test compounds for 7 days. Media was then removed and replaced with fresh media containing Alamar Blue. The cells were incubated for a further 4 hours and Alamar blue and conversion was assessed by fluorescence. Compound effectiveness was determined by assessing the reduction in Alamar blue bioconversion following 7 day treatment.

EXAMPLE 174

Sensitization of Fas Mediated Killing in Jurkat Cell Line

Human lymphoma jurkat cells were cultured in suspension in 24 well plates. Jurkat cell were treated with test compounds either alone or in the presence of suboptimal doses of anti-Fas antibody. After 18 hours of treatment cell death was assessed by Facs. Cells were incubated with propidium iodide and the percentage of cells that incorporated the stain was counted by Facs.

EXAMPLE 175

Spinal Cord Explant Experiments

Spinal cords from P1 rat pups were isolated for neurite extension analysis. Lumbar cord was separated in two along the spinal canal. 350 uM lateral sections were obtained with a McIlwain tissue chopper. Slices were cultured in poly L-lysine coated 24 well plates in Neurobasal media supplemented with B27, penicillin, streptomycin, and glutamate. Test compounds were added to the media and neurite extension out of the explant onto the poly L-coated plastic was assessed after 7 days in culture. Neurites were visualized either by phase contrast microscopy or by beta 3 tubulin immunofluorescence.

The invention claimed is:

1. A pharmaceutically active pyrrolo-β-carboline derivative represented by formula (I):

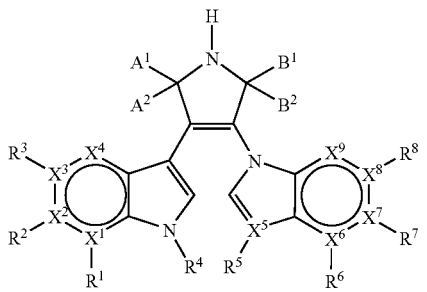

I or a pharmaceutically acceptable salt thereof wherein:
$A^1$ is H or lower alkyl, $A^2$ is H or $OR^{20}$ having S or R stereochemistry, wherein $R^{20}$ represents H or lower alkyl; or $A^1$ and $A^2$ are combined to represent oxygen;
$B^1$ is H or lower alkyl, and $B^2$ is H or $OR^{20}$ having S or R stereochemistry; or $B^1$ and $B^2$ are combined to represent oxygen;
$X^1$–$X^3$ are independently C or N;
$X^4$ is CH or N, wherein not more than two of $X^1$–$X^4$ is N;
$X^5$ represents N or C;
$X^6$–$X^8$ are independently C or N;
$X^9$ is CH or N, wherein not more than two of $X^6$–$X^9$ is N;
$R^1$–$R^3$ and $R^6$–$R^8$ represent a lone pair or O when each respective $X^1$–$X^3$ and $X^6$–$X^8$ is N; and
when $X^1$–$X^3$ or $X^6$–$X^8$ is C, each respective $R^1$–$R^3$ and $R^6$–$R^8$ is independently selected from the group consisting of:
a) H, lower alkyl, lower substituted alkyl, higher alkyl, halogen, azido, cyano, nitro, or $NR^{21}R^{22}$, wherein $R^{21}$ represents H or lower alkyl, and $R^{22}$ represents H, lower alkyl, acyl, formyl, lower alkylcarbonyl, substituted lower alkylcarbonyl, carbonyl, arylcarbonyl, substituted arylcarbonyl, heterocycle, heteroarylcarbonyl, substituted heteroarylcarbonyl, lower alkylaminocarbonyl, arylaminocarbonyl, or substituted arylaminocarbonyl;
b) $OR^{23}$, wherein $R^{23}$ is H, acyl, carbonyl, lower alkylcarbonyl, substituted lower alkylcarbonyl, arylcarbonyl, or substituted arylcarbonyl;
c) $SR^{23}$;

d) $O(CH_2)_j$—$R^{24}$, $O(CH_2)_j$—O—$R^{24}$, or $O(CH_2)_j$—S—$R^{24}$, wherein j is an integer from 1 to 8, and $R^{24}$ is selected from the group consisting of H, lower alkyl, substituted lower alkyl, aryl, substituted aryl, heteroaryl, or substituted heteroaryl;
e) $S(CH_2)_j R^{24}$, $S(CH_2)_j$—O—$R^{24}$, or $S(CH_2)_j$—S—$R^{24}$;
f) C≡C—$R^{25}$, C≡C—$OR^{25}$, or C—$CO_2R^{25}$, wherein $R^{25}$ is H, lower alkyl, substituted alkyl, aryl substituted aryl, heteroaryl, or substituted heteroaryl;
g) CH=CH—$R^{25}$, CH=CH—$OR^{25}$, or CH=CH—$CO_2R^{25}$, having a stereochemistry of E or Z;
h) C≡C—$NR^{25}R^{26}$ or C≡CCONR$^{25}R^{26}$, wherein $R^{26}$ is defined as $R^{25}$, and $R^{25}$ and $R^{26}$ are selected independently;
i) CH=CH—$NR^{25}R^{26}$ or CH=CHCONR$^{25}R^{26}$, having a stereochemistry of E or Z, wherein $R^{25}$ and $R^{26}$ are defined as in h);
j) $(CH_2)_k R^{25}$, $(CH_2)_k$—$COOR^{25}$, or $(CH_2)_k$—$OR^{25}$, wherein k is an integer from 2 to 6;
k) $(CH_2)_k NR^{26}R^{28}$, $(CH_2)_k CONR^{25}R^{26}$, wherein $R^{25}$ and $R^{26}$ are selected independently; and
l) $CH_2XR^{27}$, wherein X is O or S and $R^{27}$ is H, lowed alkyl or substituted lower alkyl, aryl, substituted aryl, heteroaryl, substituted heteroaryl;
$R^4$ is selected from the group consisting of:
m) H, lower alkyl, substituted lower alkyl, carbonyl, lower alkylcarbonyl, substituted lower alkylcarbonyl, arylcarbonyl, substituted arylcarbonyl, heterocycle, heteroarylcarbonyl, or substituted heteroarylcarbonyl;
n) $(CH_2)_k R^{28}$, $(CH_2)_k$—$COOR^{28}$, wherein k is an integer from 1 to 6, and $R^{28}$ is defined as H, lower alkyl, aryl, substituted aryl, heteroaryl, or substituted heteroaryl;
o) $(CH_2)_m XR^{29}$ wherein m is an integer from 1 to 8, X is either O or S, and $R^{29}$ is H, lower alkyl, substituted lower alkyl, acyl, carbonyl, lower alkylcarbonyl, arylcarbonyl, substituted arylcarbonyl, aryl, substituted aryl, $CH_2$-substituted aryl, heteroaryl, heterocycle, $CH_2$-substituted heterocycle, or an α- or β-antipoid sugar moiety;
p) $(CH_2)_m NR^{30}R^{31}$ wherein m is an integer from 1 to 8, and $R^{30}$ and $R^{31}$ are independently defined as $R^{29}$ above, or wherein $R^{30}$ and $R^{31}$ together are part of a heteroalkyl, substituted heteroalkyl, heteroaryl, or substituted heteroaryl ring system; with the proviso that when m is 3, $R^{30}$ and $R^{31}$ are not H;
q) $(CH_2)_m XCONHR^{32}$ wherein m is an integer from 1 to 8, X is either O, S, or NH, and $R^{32}$ is defined as $R^{29}$;
r) $CH_2CH(OR^{33})CH_2OR^{34}$, wherein each $R^{33}$ and $R^{34}$ are independently defined as H, lower alkyl, substituted lower alkyl, acyl, lower alkylaminocarbonyl, arylaminocarbonyl, substituted arylaminocarbonyl, aryl, $CH_2$-substituted aryl, heterocycle, or $CH_2$-substituted heterocycle;
s) $CO(CH_2)_n R^{35}$, wherein n is an integer from 1 to 8, and $R^{35}$ is selected from the group consisting of H, halogen, aryl, substituted aryl, heterocycle, unsubstituted heterocycle, $COR^{36}$, wherein $R^{36}$ is selected from the group consisting of H, lower alkyl, substituted lower alkyl, acyl, carbamoyl, lower alkylaminocarbonyl, arylaminocarbonyl, substituted arylaminocarbonyl, aryl, $CH_2$-substituted aryl, heterocycle, and $CH_2$-substituted heterocycle, and $CONR^{37}R^{38}$, wherein $R^{37}$ and $R^{38}$ are independently selected from R$^{29}$, or R$^{37}$ and R$^{38}$ together comprise a heteroalkyl, substituted heteroalkyl, heteroaryl, or substituted heteroaryl ring system;

t) CO(CH$_2$)$_n$XR$^{39}$, wherein n is an integer from 1 to 8, X is selected from O and S, and R$^{39}$ is defined as R$^{36}$;

u) CONH—R$^{100}$, wherein R$^{100}$ is alkyl, substituted alkyl, aryl, substituted aryl, heteroaryl, or substituted heteroaryl;

v) COCR$^{40}$R$^{41}$R$^{42}$, wherein R$^{40}$ is H or lower alkyl, and where R$^{41}$ and R$^{42}$ together comprise a substituted alkyl or substituted heteroalkyl ring system;

w) SO$_2$R$^{43}$, wherein R$^{43}$ is selected from the group consisting of hydroxyl, aryl, substituted aryl, heteroaryl, substituted heteroaryl, (CH$_2$)$_p$H, (CH$_2$)$_p$OH, and (CH$_2$)$_p$R$^{44}$, wherein p is an integer from 1 to 8, and R$^{44}$ is either OR$^{45}$, wherein R$^{45}$, is defined as R$^{29}$, or NR$^{46}$R$^{47}$, wherein R$^{46}$ and R$^{47}$ are independently defined as R$^{29}$;

x) a sugar comprising from 1 to 5 α- or β-antipoid sugar moieties, or a combination of substituted α- or β-antipoid sugar moieties;

y) a polypeptide chain of between 1 and 10 amino acids, comprising protected or unprotected D or L-amino acids, being attached to carbazole nitrogen at the carboxy terminus of the polypeptide chain;

yy)

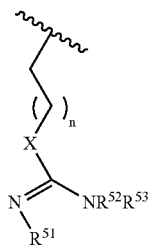

wherein X═O, S, or NH, and R$^{51}$ is H, R$^{52}$ and R$^{53}$ are independently chosen from the group consisting of H, alkyl, substituted alkyl, aryl, substituted aryl, heteroaryl, substituted heteroaryl, or R$^{51}$ and R$^{52}$ are combined to form a heteroalkyl, substituted heteroalkyl, heteroaryl, or substituted heteroaryl ring system; and R$^5$ is selected from the group consisting of z), aa) and bb):

z) a lone pair when X$^5$ is C or N;

aa) when X$^5$ is C, a substitution pattern according to any one of a) through y); and bb)

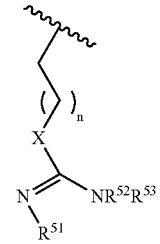

wherein X═O, S, or NH, and R$^{51}$ is H, R$^{52}$ and R$^{53}$ are independently chosen from the group consisting of H, alkyl, substituted alkyl, aryl, substituted aryl, heteroaryl, substituted heteroaryl, or R$^{51}$ and R$^{52}$ are combined to form a heteroalkyl, substituted heteroalkyl, heteroaryl, or substituted heteroaryl ring system;

wherein in formula I, when A$^1$ and A$^2$, and B$^1$ and B$^2$, respectively, combine to form oxygen, when R$^1$–R$^3$ and R$^5$–R$^8$ are H, and when R$^4$ is H or CH$_3$, then at least one of X$^1$–X$^9$ represents a ring member other than carbon; and with the proviso that 3-(1-benzimidazolyl)-4-(3-indolyl)-1H-pyrrole-2,5-dione is excluded.

2. The pharmaceutically active pyrrolo-β-carboline derivative of claim 1 wherein X$^5$ is N.

3. A compound according to claim 1 having a structure according to formula IV:

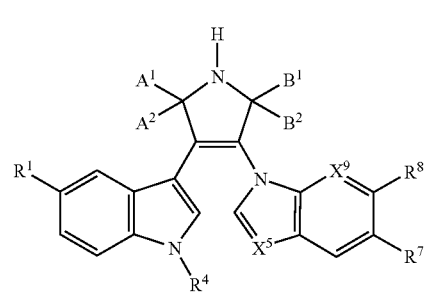

IV having functional groups according to compounds 1 to 23:

| Compound | A$^1$/A$^2$ | B$^1$/B$^2$ | R$^1$ | R$^4$ | R$^7$ | R$^8$ | X$^5$ | X$^9$ |
|---|---|---|---|---|---|---|---|---|
| 2 | O | O | MeO | H | H | H | CH | CH |
| 3 | O | O | H | H | MeO | H | CH | CH |
| 4 | O | O | MeO | H | MeO | H | CH | CH |
| 5 | O | O | BnO | H | H | H | CH | CH |
| 6 | O | O | BnO | CH$_2$CH$_2$OH | H | H | CH | CH |
| 7 | O | O | BnO | CH$_2$CH$_2$OH | MeO | H | CH | CH |
| 8 | O | O | BnO | CH$_2$CH$_2$OH | H | MeO | CH | CH |
| 9 | O | O | BnO | H | H | MeO | CH | CH |
| 10 | O | O | H | CH$_2$CH$_2$OH | H | H | CH | CH |
| 11 | O | O | BnO | H | BnO | H | CH | CH |
| 12 | O | O | H | H | BnO | H | CH | CH |
| 13 | O | O | Br | H | H | H | CH | CH |
| 14 | O | O | I | H | H | H | CH | CH |
| 15 | O | O | PhC≡C | H | H | H | CH | CH |
| 16 | O | O | PhCH$_2$CH$_2$ | H | H | H | CH | CH |

-continued

| Compound | A¹/A² | B¹/B² | R¹ | R⁴ | R⁷ | R⁸ | X⁵ | X⁹ |
|---|---|---|---|---|---|---|---|---|
| 18 | O | O | H | $CO_2^tBu$ | H | H | N | CH |
| 19 | O | O | H | $COCH_3$ | H | H | N | CH |
| 20 | O | O | H | CON(H)Ph | H | H | N | CH |
| 21 | O | O | BnO | H | H | H | N | CH |
| 22 | O | O | H | H | H | H | CH | N |
| 23 | O | O | H | $CO_2^tBu$ | H | H | CH | N | or a pharmaceutically acceptable salt thereof.

4. A pharmaceutical composition comprising a pharmaceutically effective amount of a pharmaceutically active pyrrolo-β-carboline derivative according to claim 1 in combination with a pharmaceutically acceptable carrier.

5. A method of treatment of prostate cancer or lymphoma, said method comprising administration of an effective amount of a compound according to claim 1 to a patient in need thereof.

6. A compound of Formula A, selected from the group consisting of:

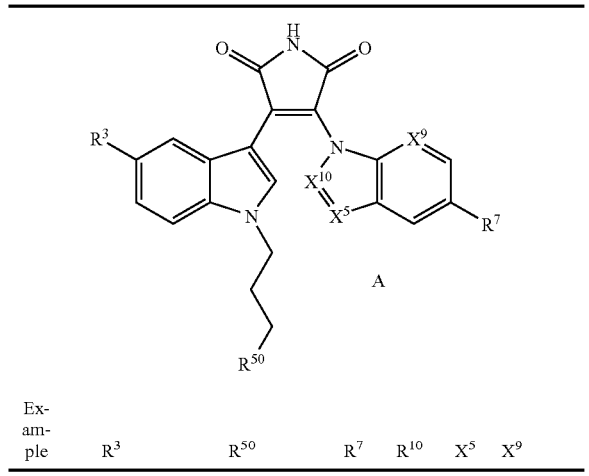

A

| Example | R³ | R⁵⁰ | R⁷ | R¹⁰ | X⁵ | X⁹ |
|---|---|---|---|---|---|---|
| 121 | H | —OH | H | CH | CH | CH ; |
| 124 | BnO | —OH | H | CH | CH | CH ; |
| 125 | H | —OH | H | CH | CMe | CH ; |
| 126 | H | —OH | BnO | CH | CH | CH ; |
| 127 | H | —OH | H | CMe | CH | CH ; |
| 128 | H | —OH | H | CH | N | CH ; |
| 129 | BnO | —OH | H | CH | CMe | CH ; |
| 130 | H | —OH | H | CH | CH | N ; |
| 131 | BnO | —OH | H | CMe | CN | CH ; |
| 132 | H | —OH | F | CH | CH | CH ; |
| 133 | H | —N(CH₃)₂ | H | CH | CH | CH ; |
| 136 | BnO | —N(CH₃)₂ | H | CH | CH | CH ; |
| 137 | H | —N(CH₃)₂ | H | CH | CMe | CH ; |
| 138 | H | —N(CH₃)₂ | BnO | CH | CH | CH ; |
| 139 | H | —N(CH₃)₂ | H | CMe | CH | CH ; |
| 140 | H | —N(CH₃)₂ | H | CH | N | CH ; |
| 141 | BnO | —N(CH₃)₂ | H | CH | CMe | CH ; |
| 142 | H | —N(CH₃)₂ | H | CH | CH | N ; |
| 143 | H | —SC(N=H)NH₂ | H | CH | CH | CH ; |
| 146 | H | —SC(N=H)NH₂ | H | CH | CMe | CH ; |
| 147 | H | —SC(N=H)NH₂ | BnO | CH | CH | CH ; |
| 148 | BnO | —SC(N=H)NH₂ | H | CH | CH | CH ; |
| 149 | BnO | —SC(N=H)NH₂ | H | CH | CMe | CH ; |
| 150 | BnO | —SC(N=H)NH₂ | H | CMe | CH | CH ; |
| 151 | H | —SC(N=H)NH₂ | H | CMe | CH | CH ; |
| 152 | H | —SC(N=H)NH₂ | H | CH | CH | N ; |
| 153 | MeO | —SC(N=H)NH₂ | H | CH | CH | CH ; |
| 154 | F | —SC(N=H)NH₂ | H | CH | CH | CH ; |
| 155 | H | —SC(N=H)NH₂ | F | CH | CH | CH ; |

| Example | R³ | R⁵⁰ | R⁷ | R¹⁰ | X⁵ | X⁹ |
|---|---|---|---|---|---|---|
| 156 | H | (thioimidazoline group) | H | CH | CH | CH ; |
| 159 | H | —SC(N=H)NH₂ | H | CH₂ | CH₂ | CH ; |
| 160 | OCH₂SPh | —SC(N=H)NH₂ | H | CH | CH | CH ; |
| 161 | H | —N₃ | H | H | H | H ; and |
| 162 | H | —NH₂ | H | H | H | H . |

7. A compound of the following formula selected from the group consisting of:

| Example | R³ | R⁵⁰ | R⁷ | R⁴ ; |
|---|---|---|---|---|
| 163 | H | OH | H | H ; |
| 164 | H | OH | H | Me ; |
| 165 | BnO | OH | H | H ; |
| 166 | H | SC(N=H)NH₂ | H | H ; |

-continued

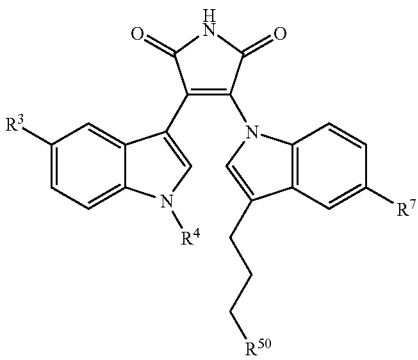

| Example | R³ | R⁵⁰ | R⁷ | R⁴ | ; |
|---|---|---|---|---|---|
| 167 | H | SC(N=H)NH₂ | H | Me | ; |
| 168 | BnO | SC(N=H)NH₂ | H | Me | ; |
| 169 | H | N(CH₃)₂ | H | Me | ; |
| 170 | H | Z | H | Me | ; |
| 171 | H | N₃ | H | Me | ; and |
| 172 | H | NH₂ | H | Me | . |

8. A method for preparation of a 3-(indol-3-yl)-4-(1N-indolyl)-1H-pyrrole-2,5-dione comprising the steps of:
  a) reacting indole with oxalyl chonde in a solvent to form a hydrochloride salt;
  b) treating said hydrochloride salt with NaOMe in alcohol to form a methyl 3-indoiglyoxylate;
  c) reacting indole With a strong base in a polar solvent;
  d) reacting the product of step c) with haloacetarnide to form an α-acetamide intermediate; and
  e) treating the products of steps b) and d) with excess base to form a 3-(indol-3-yl)-4-(1N-indolyl) -1H-pyrrole-2,5-dione.

9. A method for preparation of a 3-(indol-3-yl)-(1N-indolyl)-1H-pyrrole-2,5-dione comprising the steps of:
  a) reacting indole with Oxalyl choride in a solvent to form a hydrochloride salt;
  b) treating said hydrochloride salt with aqueous ammonia to form an acetamide intermediate,
  c) reacting indole with a base;
  d) reacting the product of step c) with haloacetate; and
  e) adding an equivalent of the product of step b) to the product of step d) and treating with excess base to form a 3-(indol-3-yl)-4-(1N-indolyl)-1H-pyrrole-2-dione.

* * * * *